U S 0 0 6 1 2 7 4 2 2 A

US006127422A

United States Patent [19]

Colacino et al.

[11] Patent Number: 6,127,422

[45] Date of Patent: Oct. 3, 2000

[54] ANTI-VIRAL METHOD

[75] Inventors: Joseph M. Colacino, Indianapolis; William J. Hornback, Fishers; Scott C. Mauldin; John E. Munroe, both of Indianapolis; Joseph C. Tang, Carmel, all of Ind.

[73] Assignee: Eli Lilly and Company, Indianapolis, Ind.

[21] Appl. No.: 09/214,536

[22] PCT Filed: May 2, 1997

[86] PCT No.: PCT/US97/07525

§ 371 Date: Jan. 6, 1999

§ 102(e) Date: Jan. 6, 1999

[87] PCT Pub. No.: WO97/41849

PCT Pub. Date: Nov. 13, 1997

Related U.S. Application Data

[60] Provisional application No. 60/016,906, May 6, 1996.

[51] Int. Cl.[7] .................. A61K 31/19; A61K 31/195; A61K 31/135; A61K 31/12; A61K 31/425

[52] U.S. Cl. .................. 514/569; 514/561; 514/563; 514/646; 514/656; 514/676; 514/679; 514/685; 514/365; 514/369; 514/370; 514/372; 514/374; 514/376; 514/377; 514/378; 514/388; 514/461; 514/451

[58] Field of Search .................. 514/569, 561, 514/563, 646, 656, 676, 679, 685, 365, 369, 370, 372, 374, 376, 377, 378, 388, 461, 451

[56] References Cited

U.S. PATENT DOCUMENTS

| | | | |
|---|---|---|---|
| 2,703,809 | 3/1955 | Ritchie | 260/469 |
| 2,744,100 | 5/1956 | Subluskey | 260/97 |
| 2,744,102 | 5/1956 | Subluskey | 260/99 |
| 2,750,382 | 12/1956 | Bible et al. | 260/247.2 |
| 2,750,405 | 6/1956 | Ritchie et al. | 260/473 |
| 2,750,407 | 6/1956 | Ritchie | 260/473 |
| 2,753,357 | 7/1956 | Bible, et al. | 260/343.3 |
| 2,759,014 | 8/1956 | Bible | 260/473 |
| 2,767,162 | 10/1956 | Picha | 260/103 |
| 2,854,474 | 9/1958 | Bible | 260/468.5 |
| 2,862,955 | 12/1958 | Hoehn | 260/468.5 |
| 2,947,778 | 8/1960 | Bible | 260/468.5 |
| 3,014,957 | 12/1961 | Hoehn | 260/465 |
| 3,038,930 | 6/1962 | Bible | 260/488 |
| 3,668,223 | 6/1972 | Jones | 260/343.2 |
| 4,252,804 | 2/1981 | Joullie et al. | 424/248.54 |
| 4,333,941 | 6/1982 | Baratz et al. | 424/267 |
| 5,015,644 | 5/1991 | Roth et al. | 514/247 |
| 5,276,053 | 1/1994 | Johnson | 514/437 |
| 5,321,044 | 6/1994 | Peters et al. | 514/510 |

FOREIGN PATENT DOCUMENTS

| | | | |
|---|---|---|---|
| 0 540 143 A2 | 8/1992 | European Pat. Off. | A61K 31/17 |
| 0 806 203 A2 | 5/1997 | European Pat. Off. | A61K 31/015 |
| WO 97 41822 | 11/1997 | WIPO | A61K 31/435 |
| WO 97 41860 | 11/1997 | WIPO | A61K 31/535 |
| WO 97 41861 | 11/1997 | WIPO | A61K 31/535 |
| WO 97 42145 | 11/1997 | WIPO | C07C 5/27 |
| WO 97 42155 | 11/1997 | WIPO | C07C 69/753 |
| WO 97 42156 | 11/1997 | WIPO | C07C 69/76 |

OTHER PUBLICATIONS

UEDA, et al.: "The Leaf Oil and Resin Acid Components of Lacebark Pine, *Pinus bungeana* Zucc." Tottori Daigaku Kogakubu Kenkyu Hokiku, vol. 20, No. 1, 1989 Japan, pp. 87–96.

Turner, et al., J. Chem. Soc. C., 1971, vol. 3, 547–553.

Cambie, et al., Aust. J. Chem., 1974, vol. 27, No. 9, 2001–2016.

Tahara, et al., Chem. Pharm. Bull., 1976, vol. 24, No. 7, 1497–1501.

Standley, et al., J. Atmos. Chem., 1994, vol. 18, No. 1, 1–15.

Matsumoto, et al., Chem. Pharm. Bull., 1996, vol. 44, No. 3, 530–533.

Caplus Abstr., No. 99:212742, Burnell, et al., Can. J. Chem., 1983, vol. 61, No. 11, 2461–2465.

Burnell, et al., Synth. Commun., 1984, vol. 14, No. 13, 1229–1237.

Cambie, et al., Aust. J. Chem., 1990, vol. 43, No. 5, 883–893.

Matsumoto, et al., Chem. Pharm. Bull., 1993, vol. 41, No. 11, 1960–1964.

Chemical Abstracts, Abstract #2502; vol. 50, No. 4, Feb. 25, 1956, Michitoshi Ohta.

G. Defaye–Duchateau, "Oxydations dans la serie de l'acide dehydroabietique," 1964, Paris, 1469–1473.

Georges Dupont, et al., "Oxydation de l'acide abietique par l'acetate mercurique. Derives de l'acide dehydroabietique substitutes dans le cycle B," 1955, Paris, 708–715.

J. C. Sircar, et al., "Free–Radical Bromination of Methyl Abietate by N–Bromosuccinimide and Solvolysis of the Products,", vol. 35, No. 9, Sep., 1970, 3090–3093.

Chem. Abstr., vol. 112, No. 21, May 21, 1990, Abstract No. 198830, Sugai, et al.

Chem. Abstr., vol. 110, No. 9, Feb. 27, 1989, Abstract No. 75825, Nishi, et al.

Chem. Abstr., vol. 91, No. 23, Dec. 3, 1979, Abstract No. 193454, Pelletier, et al.

Chem. Abstr., vol. 81, No. 7, Aug. 19, 1974, Abstract No. 25842, Wirthlin, et al.

Chem. Abstr., vol. 121, No. 17, Oct. 24, 1994, Abstract No. 195010, Tagat, et al.

(List continued on next page.)

*Primary Examiner*—Russell Travers
*Attorney, Agent, or Firm*—Arlene K. Musser

[57] ABSTRACT

A method of inhibiting an envelope virus selected from the group consisting of influenza bovine diarrheal, hepatitis C and tick borne encephalitis virus that udergoes hemagglutinin-mediated fusion with a host cell is disclosed which comprises administering to a virus-infected cell, a cell susceptible of infection or a mammal in need thereof, an effective amount of a compound as defined by Formula I in the specification.

8 Claims, No Drawings

OTHER PUBLICATIONS

Chem. Abstr., vol. 120, No. 11, Mar. 14, 1994, Abstract No. 134850, Selwood, et al.

Chem. Abstr., vol. 61, No. 5, Aug. 31, 1964, Abstract No. 5699f, Tahara, et al.

Helvetica Chemica Acta., vol. 57, No. 2, Mar. 13, 1974, Basel Ch., 351–368.

Tetrahedron, vol. 21, No. 8, Aug. 1965, Oxford GB, 2133–2154.

Cruz Frederico G., et al., Phytochemistry, vol. 31, No. 8, 1992, pp. 2793–2796.

Chem. Abstr., vol. 110, No. 21, Nov. 20, 1989, Abstract No., 195166, Node, et al.

Chem. Abstr., vol. 88, No. 25, Jun. 19, 1978, Abstract No. 191065, Ichinohe.

Chem. Abstr., vol. 83, No. 11, Sep. 15, 1975, Abstract No. 97643, Ichinohe.

Chem. Abstr., vol. 81, No. 5, Aug. 5, 1974, Abstract No. 25842, Wirthlin, et al.

Database Crossfire, Beilstein Informationssysteme, GMBH. Frankfort DE, Beilstein registry No. 4824891, XP002060909, Richard C. Cambie, et al., Australian Journal of Chemistry, vol. 44, No. 11, 1991, pp. 1553–1573.

Database Crossfire, Beilstein Informationssysteme, GMBH. Frankfurt DE, Beilstein registry No. 2179057, XP002060813, Richard C. Cambie, et al., Australian Journal of Chemistry, vol. 27, 1974, pp. 2413–2419.

Database Crossfire, Beilstein Informationssysteme, GMBH. Frankfurt DE, Beilstein registry No. 2887142, XP002060814, Richard C. Cambie, et al., Australian Journal of Chemistry, vol. 25, 1972, pp. 974–980.

Database Crossfire, Beilstein Informationssysteme, GMBH. Frankfurt DE, Beilstein registry No. 2920097, XP002060815, Richard C. Cambie, et al., Australian Journal of Chemistry, vol. 27, 1974, pp. 2001–2011.

Comptes Rendus De l'academie Bulgare des sciences, vol. 48, No. 11–12, 1995.

ANTI-VIRAL METHOD

This application is a continuation of Provisional Application Ser. No. 60/016,906 filed May 6, 1996 which is a 371 of PCT/US97/07525 filed May 2, 1997.

Influenza viruses cause an infectious disease for which there is no adequate therapeutic agent. The disadvantages of existing treatments include the onset of clinical resistance within thirty six hours and the ineffectiveness of the agents against influenza B. Killed influenza virus vaccines have been available for over sixty years. However, these vaccines have not lessened the morbidity, mortality or severe financial loss caused by this disease. It follows that an agent which treats or prevents an influenza infection or is effective at preventing the clinical symptoms associated with an influenza infection will result in a significant benefit to society.

Currently, the only compounds approved for the therapeutic and prophylactic treatment of influenza infections are the adamantanes: amantadine and rimantadine. These compounds inhibit influenza A by inhibiting the function of the M2 ion channel activity of the virus. Amantadine is a potent in vitro inhibitor of influenza A virus as demonstrated by standard antiviral assays such as the plaque reduction assay. Amantadine is effective in reducing the duration of fever and other systemic complaints including but not limited to myalgia (muscular ache) and fatigue when administered to individuals infected with influenza A within forty-eight hours of the onset of clinical symptoms. It has also been observed that amantadine results in a one hundred-fold decrease of virus titer in the nasal washes of human volunteers infected with wild-type influenza virus which correlates with a dramatic decrease in fever score. Thus, in vitro influenza inhibition is predictive of useful in vivo effects, i.e. a reduction of the clinical symptoms associated with the influenza infection.

The present invention derives from the fact that influenza is an enveloped virus which dictates that the virus envelope must be fused with the endosomal membrane of the host cell in order to initiate the process of introducing its genetic information into the cell. Because this process is common to all enveloped viruses, it is an attractive target for antiviral chemotherapy. Examples of envelope viruses which are inhibited according to the present invention include influenza, bovine diarrheal, hepatitis C, tick borne encephalitis and the like. The fusion domain of the envelope glycoprotein of influenza, hemagglutinin (HA) has been well characterized. See, White J. M., Annu. Rev. Physiol. vol. 52, pages 675–697 (1990) which is herein incorporated by reference.

Influenza virus HA provides at least two distinct functions: 1) recognition of the host cell receptor, i.e., sialic acid residues on glycoconjugates, and 2) fusion of the viral envelope with the endosomal membrane. Both functions are essential for the propagation of influenza virus in vitro and in vivo. During viral maturation, monomeric HA is inserted into a lipid bilayer, post-translationally modified and oligomerized into a trimer of identical subunits (trimeric HA). The infectivity of the progeny virus is contingent upon a site-specific cleavage of HA by host cell protease(s). This cleavage results in the formation of two polypeptide chains, HA1 and HA2, which remain associated by non-covalent interactions as well as by an intermolecular and intramolecular disulfide bonds.

It has been established that influenza HA has two functionally relevant conformations. One conformation (Form A) exists as a metastable structure at neutral pH and mediates receptor recognition. Following receptor mediated binding to the host cell, the virus is transported to the endosomal compartment where it encounters an acidic environment. The low pH triggers a dramatic structural rearrangement of HA (Form A) which results in the formation of the other, more stable conformation of HA (Form B).

Form B of HA is required for fusion of the virus envelope with the endosomal membrane. It is the structural rearrangement from Form A to Form B of HA that allows the fusion domain of HA to directly interact with the endosomal membrane enabling the release of viral genetic information into the host cell cytoplasm. These considerations lend themselves to the development of a strategy for antiviral intervention based on the abrogation of HA-mediated fusion of virus-host membranes.

The present invention relates to methods for using the compounds disclosed in the application for the treatment or prevention of viral infection and the resultant symptoms. These compounds, their pharmaceutically acceptable salts and the pharmaceutical compositions can be used alone or in combination with other antivirals, immunomodulators, antibiotics or vaccines.

The present invention relates to a method of treating or preventing a virus infection where the virus is an envelope virus that undergoes hemagglutinin-mediated fusion with the host cell which comprises administering to a virus infected cell, a cell susceptible of infection or a mammal in need thereof an effective amount of a compound of formula I:

wherein:

R is hydrogen or R and $R^6$ combine to form a bond;

$R^0$ and $R^1$ are independently hydrogen, hydroxy, $C_1$–$C_6$ alkyl, $C_1$–$C_6$ alkoxy, hydroxy($C_1$–$C_6$ alkyl), sulfhydryl, sulfamyl, —$SO_2$—Cl, —S—C(O)—N($CH_3$)$_2$, amino, $C_1$–$C_4$ alkylamino, di($C_1$–$C_4$ alkyl)amino, $C_1$–$C_4$ alkylsulfonylamino, di($C_1$–$C_4$ alkylsulfonyl)amino —$X^0$—O—C(O)—$C_1$–$C_4$ alkyl, —O—$(X^1)_i$—$X^2$, —C(O)—$X^3$, —N—C(O)—$R^2$ or —O——$R^3$;

$X^0$ is a bond or divalent($C_1$–$C_6$ alkyl);

$X^1$ is an amino acid;

$X^2$ is hydrogen or an amino protecting group;

i is 1, 2 or 3;

$X^3$ is $C_1$–$C_6$ alkyl, $C_1$–$C_6$ alkoxy, halo($C_1$–$C_6$ alkyl), hydroxy($C_1$–$C_6$ alkyl) or phenyl;

$R^2$ is $C_1$–$C_4$ alkyl, $C_1$–$C_4$ alkoxy, halo($C_1$–$C_4$ alkyl), hydroxy($C_1$–$C_4$ alkyl), phenyl, p-methoxy-phenyl, p-fluoro-phenyl, naphthyl, pyridyl, piperidinyl, thiazolyl, oxazolyl, thienyl, furyl, tetrahydrofuryl or cyclohexyl;

$R^3$ is $C_1$–$C_6$ alkenyl, —$CH_2$—$R^{3a}$, —C(O)—$R^{3b}$, —C(S)—$R^{3c}$, —C($CH_3$)$_2$C(O)$NH_2$, phenyl or a group of the formula:

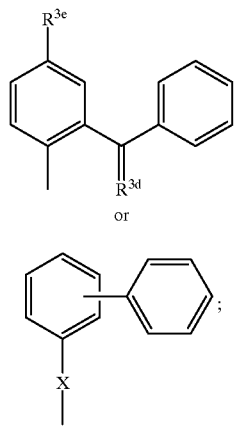

R³ᵃ is phenyl, p-fluorophenyl, pyridyl, pyrrolidinyl, piperidinyl, piperazinyl, morpholinyl, N—($C_1$–$C_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

R³ᵇ is pyrrolidinyl, piperidinyl, piperazinyl, morpholinyl, N—($C_1$–$C_4$ alkoxycarbonyl)piperidinyl, N-(trifluoromethyl)piperidinyl, benzyloxy, pyridylmethyloxy, $C_1$–$C_6$ alkoxy, halo($C_1$–$C_4$ alkoxy), amino, $C_1$–$C_4$ alkylamino or di($C_1$–$C_4$ alkyl)amino;

R³ᶜ is amino, $C_1$–$C_4$ alkylamino or di($C_1$–$C_4$ alkyl)amino;

R³ᵈ is oxygen, hydroximino, hydrazino or =CHZ;

Z is hydrogen, $C_1$–$C_4$ alkyl, halogen, di($C_1$–$C_4$ alkyl) amino, $C_1$–$C_4$ alkoxycarbonyl, carbamoyl($C_1$–$C_4$ alkyl), N-($C_1$–$C_4$ alkyl)carbamoyl or N,N-di($C_1$–$C_4$ alkyl) carbamoyl;

R³ᵉ is hydrogen, nitro or trifluoromethyl;

X is a bond or —(CH₂)—;

R⁴ is hydrogen, hydroxy, amino, $C_1$–$C_4$ alkylamino, di($C_1$–$C_4$ alkyl)amino, $C_1$–$C_4$ alkoxy, =O, —O—S (CH₃)₂ C(CH₃)₃, $C_2$–$C_6$ alkanoyloxy, N—($C_2$–$C_6$ alkanoyl)amino, =N—R⁵ or R⁴ and R⁶ combine to form a bond;

R⁵ is hydroxy, amino, $C_1$–$C_4$ alkylamino, di($C_1$–$C_4$ alkyl) amino, $C_1$–$C_4$ alkoxy, pyridylmethoxy, benzyloxy, piperazinyl, N-(methyl)piperazinyl or —O—CH₂—C(O)—R⁵ᵃ;

R⁵ᵃ is hydroxy or $C_1$–$C_4$ alkoxy;

R⁶ is hydrogen, halo, $C_1$–$C_4$ alkyl or =O;

R⁷ is hydrogen or $C_1$–$C_4$ alkyl;

R⁸ is hydroxy, halo, $C_1$–$C_6$ alkoxy, pyrrolidinyl, piperidinyl, piperazinyl, 4-methyl-piperazinyl, morpholinyl or —N(R⁹)—R¹⁰;

R⁹ is hydrogen or methyl;

R¹⁰ is -(divalent $C_1$–$C_6$ alkyl)—R¹⁰ᵃ;

R¹⁰ᵃ is pyridyl, with the proviso that R⁶ cannot combine with both R⁴ and R to form a bond;

or a pharmaceutically acceptable salt thereof.

All temperatures stated herein are in degrees Celsius (°C.). All units of measurement employed herein are in weight units except for liquids which are in volume units.

The term "halo" represents chloro, fluoro, bromo or iodo.

The term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl and the like. The term "$C_1$–$C_6$ alkyl" includes within its definition the term "$C_1$–$C_4$ alkyl."

The term "halo($C_1$–$C_6$)alkyl" represents a straight or branched alkyl chain having from one to six carbon atoms with 1, 2 or 3 halogen atoms attached to it. Typical halo ($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

The term "hydroxy($C_1$–$C_6$)alkyl" represents a straight or branched alkyl chain having from one to six carbon atoms with an hydroxy group attached to it. Typical hydroxy ($C_1$–$C_6$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl, hydroxypentyl and the like.

The term "$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

The term "di($C_1$–$C_4$)alkylamino" represents a straight or branched dialkylamino chain having two alkyl chains, each having independently from one to four carbon atoms attached to a common amino group. Typical di($C_1$–$C_4$) alkylamino groups include dimethylamino, ethylmethylamino, methylisopropyl-amino, t-butylisopropylamino, di-t-butylamino and the like.

The term "$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The term "$C_2$–$C_6$ alkenyl" represents a straight or branched alkenyl chain having from two to six carbon atoms. Typical $C_2$–$C_6$ alkenyl groups include ethenyl, propenyl, isopropenyl, buten-2-yl, t-butenyl, penten-1-yl, hexen-3-yl, 3-methylpentenyl and the like.

The term "$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "carbamoyl($C_1$–$C_4$)alkyl" represents a straight or branched alkyl chain having from one to four carbon atoms with a carbamoyl group attached to it. Typical carbamoyl($C_1$–$C_4$)alkyl groups include carbamoylmethyl, carbamoylethyl, carbamoylpropyl, carbamoylisopropyl, carbamoylbutyl and carbamoyl-t-butyl and the like.

The term "N-($C_1$–$C_4$)alkylcarbamoyl" represents a straight or branched alkyl chain having from one to four carbon atoms attached to the nitrogen atom of a carbamoyl moiety. Typical N-($C_1$–$C_4$)carbamoyl groups include N-methylcarbamoyl, N-ethylcarbamoyl, N-propylcarbamoyl, N-isopropylcarbamoyl, N-butylcarbamoyl, N-t-butylcarbamoyl and the like.

The term "N,N-di($C_1$–$C_4$ alkyl)carbamoyl" represents a straight or branched alkyl chain having a straight or branched $C_1$–$C_4$ alkyl chain attached to each of the nitrogen atoms on a carbamoyl moiety. Typical N-($C_1$–$C_4$) alkylcarbamoyl groups include N,N-dimethylcarbamoyl, N-ethyl-N-methylcarbamoyl, N-propyl-N-butylcarbamoyl, N,N-diisopropylcarbamoyl, N-methyl-N-butylcarbamoyl and the like.

The term "$C_1$–$C_4$ alkylsulfonylamino" represents a straight or branched alkyl group having from one to four carbon atoms attached to a sulfonylamino moiety. Typical $C_1$–$C_4$ alkylsulfonylamino groups include methylsulfonylamino, ethylsulfonylamino, propylsulfonylamino, isopropylsulfonyl-amino, butylsulfonylamino, isobutylsulfonylamino, sec-butylsulfonylamino, and t-butylsulfonylamino.

The term "di($C_1$–$C_4$ alkylsulfonyl)amino" represents two $C_1$–$C_4$ alkylsulfonyl moieties attached to an amino moiety. Typical di($C_1$–$C_4$ alkylsulfonyl)amino groups include methylmethylsulfonylamino, ethylmethylsulfonylamino, propylethylsulfonylamino, isopropylmethylsulfonylamino, t-butylethylsulfonylamino, butylbutylsulfonylamino and the like.

The term "$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

The term "$C_2$–$C_6$ alkanoyloxy" represents a straight or branched alkyl group having from one to five carbon atoms attached to a carbonyloxy moiety. Typical $C_2$–$C_6$ alkanoyloxy groups include ethanoyloxy, propanoyloxy, isopropanoyloxy, butanoyloxy, isobutanoyloxy, sec-butanoyloxy, t-butanoyloxy, pentanoyloxy and the like.

The term "$C_2$–$C_6$ alkanoylamino" represents a straight or branched alkyl group one to five carbon atoms attached to a carbonylamino moiety. Typical $C_2$–$C_6$ alkanoylamino groups include ethanoylamino, propanoylamino, isopropanoylamino, butanoyl-amino, isobutanoylamino, sec-butanoylamino, t-butanoylamino, pentanoylamino and the like.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reactions) on other positions of the intermediate molecule and can be selectively removed at the appropriate point without disrupting the remainder of the molecule including any other amino-protecting group(s).

Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(dibutylmethylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds used in the present invention have at least two asymmetric centers as denoted by the asterisks in the formula below:

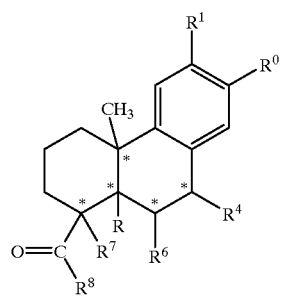

The following stereoisomers are preferred:

I-1

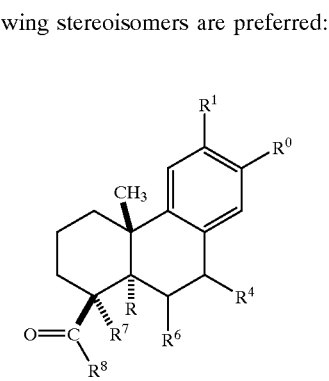

-continued

I-2

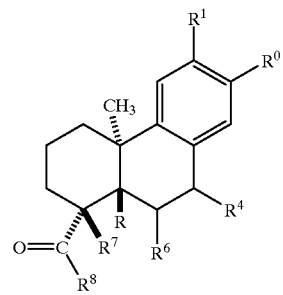

I-3

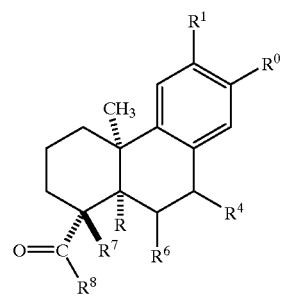

I-4

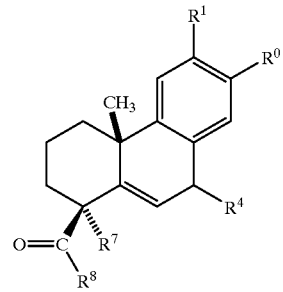

I-5

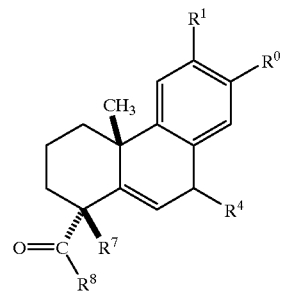

I-6

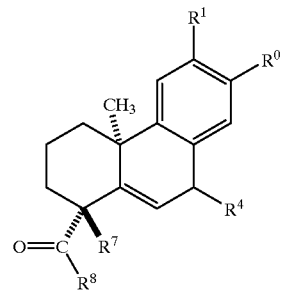

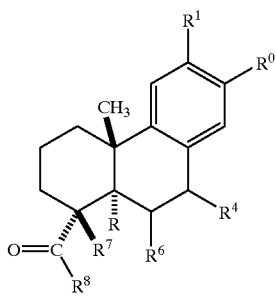

I-7

Preferred compounds used in the claimed method are those compounds of formula I where:

$R^0$ is hydrogen, hydroxy, $C_1$–$C_6$ alkyl, $C_1$–$C_6$ alkoxy, hydroxy($C_1$–$C_6$ alkyl), —$X^0$—O—C(O)—$C_1$–$C_4$ alkyl, —O—$(X^1)_i$—$X^2$, —C(O)—$X^3$ or —O—$R^3$;

$R^1$ is hydrogen, hydroxy, $C_1$–$C_6$ alkoxy, sulfhydryl, sulfamyl, —$SO_2$—Cl, amino, di($C_1$–$C_4$ alkylsulfonyl)amino —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group;

i is 1 or 2;

$X^3$ is $C_1$–$C_6$ alkyl;

$R^2$ is hydroxy($C_1$–$C_4$ alkyl);

$R^3$ is $C_1$–$C_6$ alkenyl, —$CH_2$—$R^{3a}$, —C(O)—$R^{3b}$, —C(S)—$R^{3c}$, —C($CH_3$)$_2$C(O)$NH_2$ or a group of the formula:

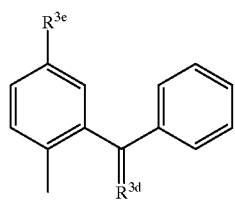

or

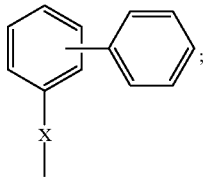

;

$R^{3a}$ is phenyl, p-fluorophenyl, pyridyl, piperidinyl, piperazinyl or morpholinyl;

$R^{3b}$ is piperidinyl, piperazinyl, morpholinyl, N-($C_1$–$C_4$ alkoxycarbonyl)piperidinyl, N-(trifluoromethyl)piperidinyl, halo($C_1$–$C_4$ alkoxy) or di($C_1$–$C_4$ alkyl)amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is hydrogen, hydroxy, amino, =O, $C_2$–$C_6$ alkanoyloxy, =N—$R^5$, —OSi($CH_3$)$_2$ or $R^4$ and $R^6$ combine to form a bond;

$R^5$ is hydroxy, amino, di($C_1$–$C_4$ alkyl)amino, $C_1$–$C_4$ alkoxy, pyridylmethoxy, N-(methyl)piperazinyl or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, methoxy, 4-methylpiperazinyl or —N($R^9$)—$R^{10}$;

$R^9$ is hydrogen;

$R^{10}$ is —$CH_2$—$R^{10a}$; and $R^{10a}$ is pyridyl;

or a pharmaceutically acceptable salt thereof.

Of these compounds, more preferred are those compounds of formula I where:

$R^0$ is hydrogen, hydroxy, $C_1$–$C_6$ alkoxy, —O—$(X_1)_i$—$X^2$, —$X^0$—O—C(O)—$C_1$–$C_4$ alkyl or —O—$R^3$;

$R^1$ is hydrogen, hydroxy, $C_1$–$C_6$ alkoxy or —O—$R^3$;

$X^0$ is a bond;

$X^1$ is an amino acid;

$X^2$ is hydrogen or an amino protecting group;

i is 1 or 2;

$R^3$ is $C_1$–$C_6$ alkenyl, —$CH_2$—$R^{3a}$ or —C(O)—$R^{3b}$;

$R^{3a}$ is p-fluorophenyl or pyridyl;

$R^{3b}$ is piperidinyl;

$R^4$ is hydrogen, hydroxy, =O or =N—$R^5$;

$R^5$ is hydroxy, dimethylamino or N-(methyl)piperazinyl;

$R^6$ is hydrogen, bromo or =O;

$R^7$ is methyl; and $R^8$ is methoxy;

or a pharmaceutically acceptable salt thereof.

Of these compounds, even more preferred are those compounds of formula I where:

R is hydrogen;

$R^0$ is hydrogen, hydroxy, $C_1$–$C_4$ alkoxy, —O—$(X^1)_i$—$X^2$, —O—C(O)methyl or —O—$R^3$;

$R^1$ is hydrogen, hydroxy, $C_1$–$C_4$ alkoxy or —O—$R^3$;

$X^1$ is glycine, alanine or valine;

$X^2$ is hydrogen, t-butoxycarbonyl or benzyloxycarbonyl;

$R^4$ is =O or =N—$R^5$;

$R^5$ is hydroxy;

$R^6$ is hydrogen;

or a pharmaceutically acceptable salt thereof.

The compounds of formula I may be prepared according to procedures known in the art. For example, the following Reaction Schemes may be used, alone or in combination to provide the desired compounds. Once a reaction is complete, the intermediate compound may be isolated by procedures well-known in the art; for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

The compounds of formula I where $R^4$ is =O or =N—R may be prepared according to the procedures shown below in Reaction Scheme I.

Reaction Scheme I
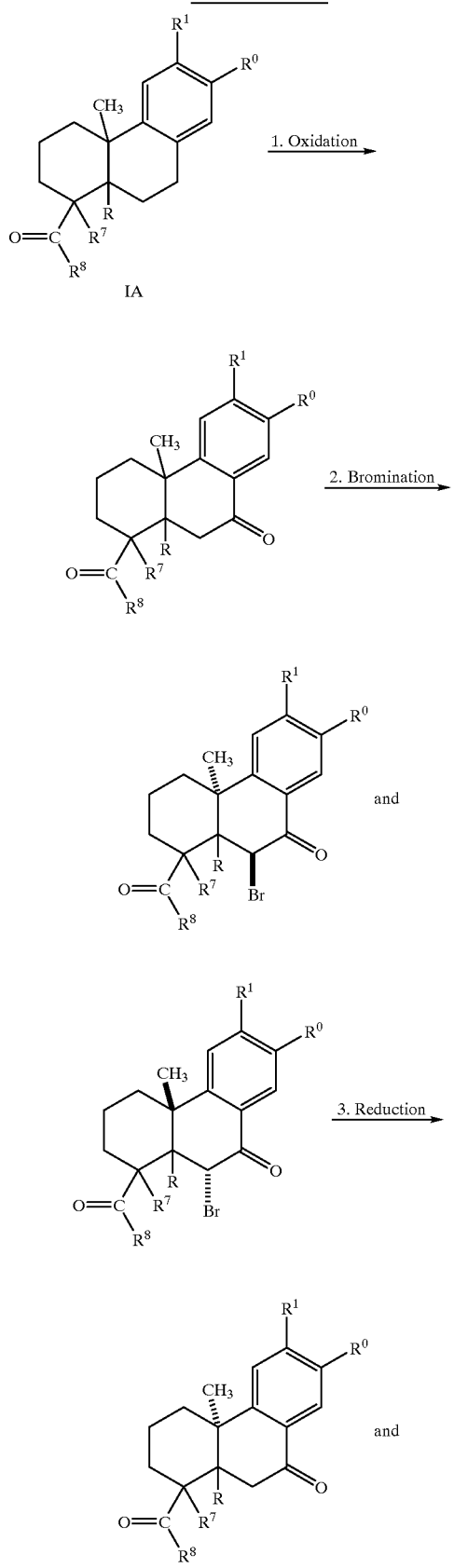
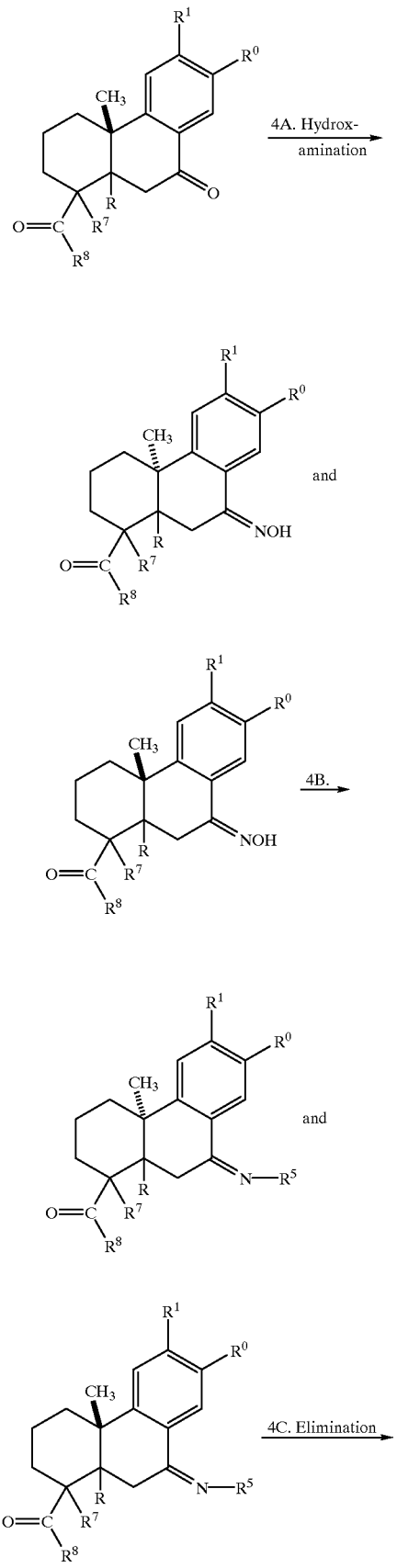

-continued

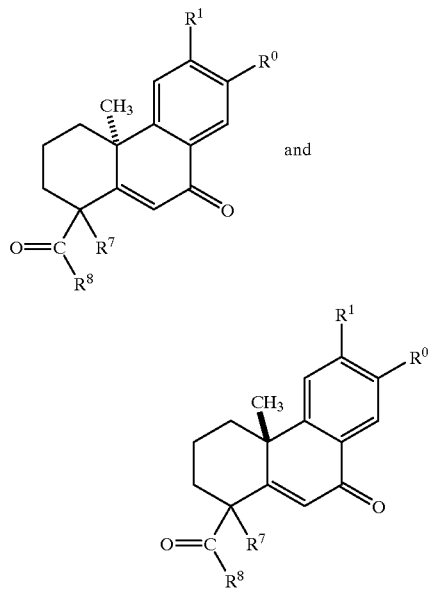

and where Reactions I.4A and 4B represent alternative reactions that follow Reaction 1.3 and Reaction I.4C is an alternative reaction following Reaction I.2.

Reaction scheme I is accomplished by carrying out reactions 1–4 in sequential order. Reaction I.1 is carried out by oxidizing a compound of formula IA, for example, by reaction with chromium trioxide in an acetic acid/water mixture, to provide the corresponding ketone. The chromium trioxide is generally employed in an amount ranging from equimolar proportions to about a 4 molar excess relative to the compound of formula IA, preferably in about a 2–4 molar excess. The acetic acid/water mixture is generally a 10:1 to a 2:1 mixture of acetic acid to water, preferably about 4:1. The reaction is generally substantially complete after about 1 to 10 hours when conducted at a temperature of from about 23° C. to about 60° C. The reaction is preferably conducted at a temperature of from about 23° C. to about 30° C. for about 5 to 10 hours.

In Reaction I.2, the ketone obtained from Reaction I.1 is reacted with bromine in a suitable solvent such as diethyl ether, tetrahydrofuran or dimethoxyethane, to provide a mixture of bromoketones which are then separated using standard separation techniques such as chromatography. These isomerically pure bromoketones are then used to prepare various isomerically pure compounds of formula I. The bromine is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 1 to 3 hours when conducted at a temperature of from about 23° C. to about 30° C. The reaction is preferably conducted at room temperature for about 1 to 1.5 hours.

Alternatively, the ketone obtained from Reaction I.1 is reacted with a silylating agent in the presence of a base in a suitable solvent such as methylene chloride, diethyl ether or tetrahydrofuran to provide the corresponding silylated enol ether. Preferred bases include 2,6-lutidine and collidine. A preferred silylating agent is t-butyldimethylsilyl trifluoromethanesulfonate. The silylating agent is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 30 minutes to 2 hours when conducted at a temperature of from about 0° C. to about 50° C. The reaction is preferably conducted at a temperature of from about 10° C. to about 25° C. for about 30 minutes to about 1 hour.

The silylated enol ether is then reacted with bromine substantially as described above with the exception that the reaction is carried out in the presence of acetic acid. Typical solvents suitable for use in this reaction include any organic solvent such as methylene chloride, diethyl ether or tetrahydrofuran. Solvent choice is not critical so long as the solvent employed is inert to the ongoing reaction and the reactants are sufficiently solubilized to effect the desired reaction.

In Reaction I.3, the bromoketone is reduced, for example by reaction with zinc dust and sodium acetate in glacial acetic acid, to provide the corresponding ketones. The zinc is generally employed in an amount ranging from about equimolar proportions to about a 4 molar excess relative to the ketone reactant, preferably in about a 1.5–3 molar excess. The sodium acetate is generally employed in an amount ranging from about 0.6 molar equivalents to about 1.2 molar equivalents relative to the ketone reactant. The reaction is generally substantially complete after about 1 to 10 hours when conducted at a temperature of from about 60° C. to the reflux temperature of the mixture. The reaction is preferably conducted at reflux temperature for about 1 to 2 hours.

Alternatively, hydroxylamine hydrochloride is reacted with sodium acetate in a suitable solvent such as ethanol. The sodium acetate is generally employed in an amount ranging from about 1.1 molar equivalents to about a 50 molar excess relative to the hydroxylamine. The reaction is generally substantially complete after about 1 to 72 hours when conducted at a temperature of from about 25° C. to about 80° C. The reaction is preferably conducted at a temperature in the range of from about 25° C. to about 30° C. for about 5 to 24 hours.

In Reaction I.4A, the ketone obtained from Reaction I.3 is reacted with hydroxylamine hydrochloride in a mixture of methanol, water and acetic acid to provide the desired oxime compound. The hydroxylamine hydrochloride is generally employed in an amount ranging from about equimolar proportions to about a 4 molar excess relative to the ketone reactant, preferably in about a 1.3–3 molar excess. The ratio of methanol to water to acetic acid is generally 10–20:1:0.1, preferably 15:1:0.1 (by volume?). The reaction is generally substantially complete after about 1 hour to about 2 days when conducted at a temperature of from about 40° C. to the reflux temperature of the mixture. The reaction is preferably conducted at reflux temperature for about 1 to 6 hours.

In Reaction I.4B, the ketone obtained from Reaction I.3 is reacted with an hydrazine hydrochloride such as 1-amino-4-methylpiperazine, 1,1-dimethylhydrazine or hydrazine in the presence of a base in an inert solvent at a temperature of from about 25° C. to 80° C. for 2 to 24 hours. Typical bases include sodium acetate, potassium hydroxide, triethylamine and the like. Suitable solvents include ethanol, isopropanol and dimethylformamide. Solvent choice is not critical so long as the solvent employed is inert to the ongoing reaction and the reactants are sufficiently solubilized to effect the desired reaction.

In Reaction I.4C, the compounds obtained from Reaction I.2 where R is hydrogen may be eliminated by reacting the bromo ketone reactant with a base such as sodium methoxide in methanol, sodium ethoxide in ethanol, or triethylamine to provide the unsaturated compounds of formula I where R and $R^6$ are combined to form a bond. The base is generally employed in about a 2–4 molar excess relative to the bromo ketone reactant, preferably in about a 3 molar excess. The reaction is generally substantially complete after about 3 to 9 hours when conducted at a temperature of from about 40° C. to the reflux temperature of the mixture. The reaction is preferably conducted at reflux temperature 3 to 5 hours.

The phenyl moiety of the compounds of formula I prepared above may be substituted according to Reaction Scheme II, as follows.

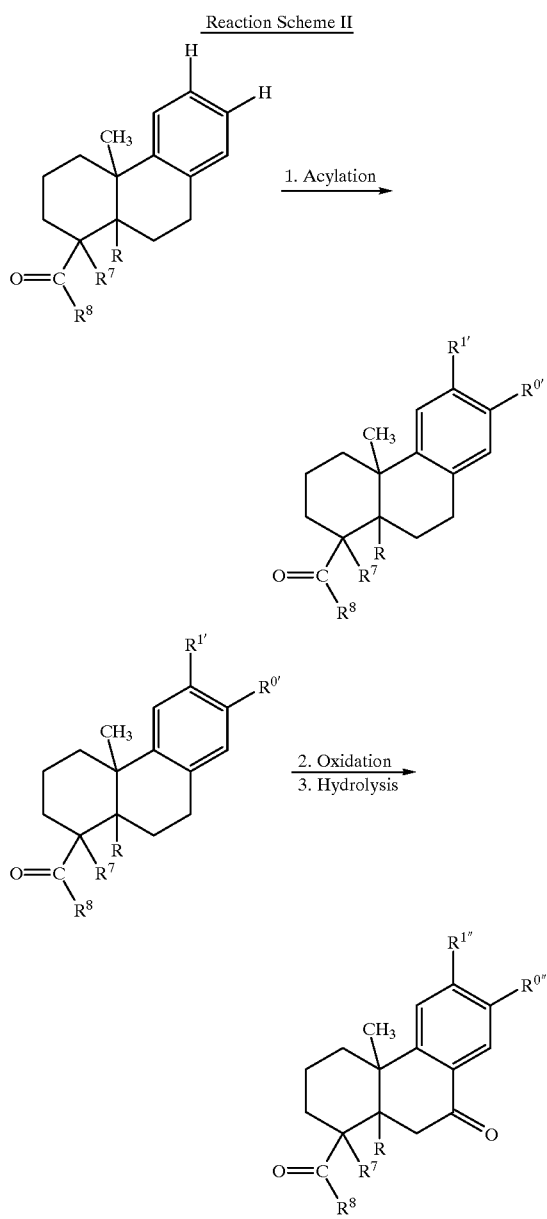

where $R^{0'}$ and $R^{1'}$ are independently hydrogen or —C(O)CH$_3$; and $R^{0''}$ and $R^{1''}$ are independently hydrogen or hydroxy.

In Reaction II.1, the compound of formula I where $R^0$ and $R^1$ are each hydrogen is subjected to a Friedel-Crafts acylation by reacting the compound of formula I with an acid halide, in the presence of a catalyst in an inert solvent such as carbon disulfide. The acid halide is generally employed in an amount ranging from about equimolar proportions to about a 1.5 molar excess relative to the compound of formula I, preferably in about a 1.1–1.3 molar excess. Preferred acid halides include acetyl chloride, acetyl bromide or the like. Preferred catalysts include aluminum trichloride, aluminum tribromide or the like. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 2 hours.

In Reaction II.2, the acylated compound of formula I obtained from Reaction II.1 is oxidized to provide the corresponding phenol in a two step reaction. First, the acyl moiety is reacted with a peracid in the presence of an acid catalyst in an inert solvent such as dimethoxyethane to provide the corresponding ester with is then reacted with sodium bicarbonate in an alcohol/water mixture to provide the desired phenol.

The peracid is generally employed in an amount ranging from about equimolar proportions to about a 2 molar excess relative to the acyl moiety, preferably in about a 1–1.3 molar excess. The amount of catalyst typically employed is in the range of 0.005–0.04 equivalents relative to the acyl moiety. A preferred peracid is metachloro-peroxybenzoic acid. A preferred catalyst is p-toluenesulfonic acid. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 3 hours.

The resultant ester is typically refluxed with a base in a methanol/water mixture for about 1 to 7 hours to provide the desired phenol compound. Preferred bases include sodium bicarbonate, sodium carbonate, sodium hydroxide or potassium hydroxide or the like. The base is generally employed in an excess, for example from about a 1 molar excess to about a 6 molar excess relative to the ester moiety, preferably in about a 2–5 molar excess The phenol compounds obtained from Reaction Scheme II may be used to prepare various substituted compounds of formula I, as described below.

For example, the hydroxy moiety may be alkylated by reacting the phenol compound with a suitable alkylating agent in the presence of a base in an inert solvent. Examples of bases include triethylamine, diisopropyl ethylamine, sodium hydride and potassium carbonate. Typical solvents include methylene chloride, tetrahydrofuran, dimethylformamide and the like. Solvent choice is not critical so long as the solvent employed is inert to the ongoing reaction and the reactants are sufficiently solubilized to effect the desired reaction. Suitable alkylating agents include iodomethane, allyl iodide, p-fluorophenyl bromide, 3-bromomethylpyridine and 2-fluorobenzophenone and the like. The reaction is generally substantially complete after about 1 to 20 hours when conducted at a temperature of from about 0° C. to 170° C. The reaction is preferably conducted at a temperature of from about 25° C. to about 80° C. for about 4 to 16 hours.

Alternatively, the hydroxy moiety may be alkylated by reacting the phenol with an alcohol in the presence of triphenylphosphine and a suitable activating agent in an inert solvent, such as tetrahydrofuran or ethylene glycol dimethyl ether. Examples of suitable activating agents include diethyl azodicarboxylate, dimethyl azodicarboxylate, diisopropyl azodicarboxylate and the like. Examples of alcohols include 3-pyridyl carbinol, N-t-butoxycarbonyl-3-piperidinemethanol and the like. The reaction is generally substantially complete after about 0.5 to 2 hours when conducted at a temperature of from about 0° C. to 85° C. The reaction is preferably conducted at a temperature of from about 25° C. to about 70° C. for about 30 minutes to 1 hour.

The hydroxy moiety may be converted to an ester or a carbonate by reacting the phenol with an acylating agent in the presence of a base in an inert solvent, such as methylene chloride, tetrahydrofuran or dimethylformamide. Typical bases include triethylamine, diisopropyl ethylamine, sodium hydride and the like. Typical acylating agents include N-(t-butoxycarbonyl)-4-chlorocarbonyl piperdine, 2,2,2-trichloroethyl chloroformate, N-(t-butoxycarbonyl)-hydroxybenzotriazole amino esters. The reaction is generally substantially complete after about 1 to 20 hours when conducted at a temperature of from about 0° C. to 60° C. The reaction is preferably conducted at a temperature of from about 10° C. to about 25° C. for about 1 to 5 hours.

The hydroxy moiety may be converted to the corresponding aniline in a three step reaction. First, the phenol is reacted with a suitably substituted amide such as 2-methyl-2-bromo-propanamide in the presence of a base such as sodium hydride or triethylamine in an inert solvent, such as dioxane or tetrahydrofuran at a temperature of 25° C. to 100° C. to provide the corresponding amido-ether. This amido-ether is then reacted with sodium hydride in an inert solvent such as dimethylformamide, 1,3-dimethyl-3,4,5,6-tetrahydro-2(1H)-pyrimidone or a mixture thereof at temperatures ranging from 25° C. to 145° C. to provide the rearranged amido-alcohol. Finally, the amido-alcohol is reacted with an acid, such as hydrochloric acid in dioxane at 50° C. to 100° C. to provide the desired aniline.

The aniline may be converted to the corresponding sulfonamide by reacting the aniline with a sulfonyl chloride such as methanesulfonyl chloride or isopropylsulfonyl chloride in the presence of a base, such as triethylamine, diisopropyl ethylamine or sodium hydride at a temperature of from about 0° C. to 50° C. in an inert solvent, such as methylene chloride, tetrahydrofuran or dimethylformamide.

The hydroxy moiety may be converted to a thiophenol in a three step reaction. First the phenol is reacted with a thio-carbamoyl (for example dimethylthiocarbamoyl chloride) in the presence of a base in suitable solvent, such as water or dimethylformamide at a temperature ranging from 25° C. to 50° C. for 1 to 3 hours to provide the oxo-thiocarbamate. Typical bases include potassium hydroxide, triethylamine and the like. The oxo-thiocarbamate is converted to the corresponding thio-oxocarbamate compound by isolating and heating the neat solid to its melting point. Finally, the thio-oxocarbamate is reacted with a base, such as potassium hydroxide or sodium hydroxide in an alcoholic solvent, such as methanol or ethanol at a temperature of 20° C. to 80° C. for 20 minutes to 1 hour to provide the corresponding thiophenol.

The thiophenol may be converted to the corresponding sulfonamides by reacting the thiophenol with an oxidizing agent (for example, potassium nitrate) in an inert solvent such as acetonitrile, followed by the addition of a chlorinating agent (for example, sulfuryl chloride) at temperatures ranging from 0° C. to 25° C. to provide a mixture of sulfonyl chlorides which are separable using standard chromatographic techniques. These sulfonyl chlorides may be converted to the desired sulfonamides by reaction with an appropriately substituted amine such as ammonium hydroxide, methylamine, isopropylamine or benzylamine at a temperature of from about 0° C. to 40° C. in an inert solvent such tetrahydrofuran.

The hydroxy moiety may be converted to the corresponding amino esters by reacting the phenol with an amino protected amino acid in the presence of a coupling reagent and a catalyst in an inert solvent such as diethyl ether, tetrahydrofuran or methylene chloride. Preferred amino protecting groups include t-butoxycarbonyl or benzyloxycarbonyl. The amino reactant is generally employed in equimolar proportions to a slight excess (1.3 equivalents) relative to the phenol reactant in the presence of an equimolar quantity to a slight excess (1.5 equivalents) of the coupling reagent. Typical coupling agents include dicyclohexylcarbodiimide (DCC), 1-(3-dimethylaminopropyl)-3-ethylcarbodiimide, benzotriazol-1-yloxy-tris(dimethylamino)phosphonium hexafluorophosphate (BOP), N,N'-diethylcarbodiimide, carbonyldiimidazole, bis(2-oxo-3-oxazolidinyl)phosphinic chloride (BOP-Cl) or N-ethoxycarbonyl-2-ethoxy-1,2-dihydroquinoline (EEDQ) and the like. Preferred coupling agents include DCC and BOP. Typical catalysts include DMAP and 4-pyrrolopyridine. The reaction is substantially complete in 1 to 10 hours when carried out at a temperature of from about −30° C. to about 35° C., preferably from about 0° C. to about 25° C.

The starting materials used in the procedures detailed above may be obtained commercially or prepared according to procedures known in the art. For example, methyl O-methylpodocarpate having the following stereochemistry may be obtained from Aldrich Chemical Company:

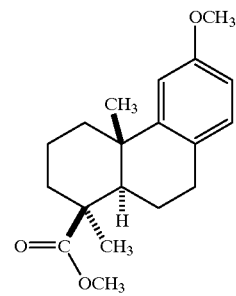

In addition, the compound(s) of formula IA, below may be prepared substantially in accordance with the procedure detailed in Ohta and Ohmuri, Chem. Pharm. Bull. (Tokyo), vol 5, page 91 (1957). The isomeric mix of compounds may be separated using standard separation techniques. Preferably, these isomers are obtained using the bromination methodology described above in Reaction Scheme I.

The compounds) of formula IA may also be used to prepare other isomers using the procedure detailed in Pelletier et al., Tetr. Lett. page 4179 (1971). For example, heating the compound(s) of formula IA in a high boiling point solvent such as triethylene glycol dimethylether (triglyme) results in a compound of formula IB as follows:

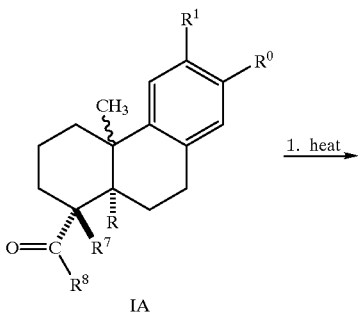

IA

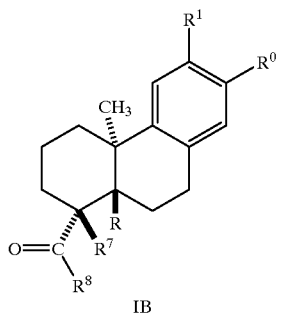

IB

The resultant mixture of isomers is then separated using standard procedures such as recrystallization or column chromatography or may be subjected to the bromination methodology described above in Reaction Scheme I.

The following Preparations and Examples further illustrate specific aspects of the present invention. It is to be understood, however, that these examples are included for illustrative purposes only and are not intended to limit the scope of the invention in any respect and should not be so construed.

PREPARATION 1

N-t-Butoxycarbonyl-4-carboxy-piperidine

To a solution of 1.0 g (7.74 mmol) of 4-carboxy-piperidine in 40 ml of a 1:1 water/dioxane mixture, was added 3.2 g (23.2 mmol) of potassium carbonate ($K_2CO_3$) followed by 2.1 ml (9.3 mmol) of di(t-butyl)dicarbonate ($BOC_2O$). After 2 hours, the mixture was diluted with methylene chloride ($CH_2Cl_2$). The resulting layers were separated and the organic layer was dried over sodium sulfate ($Na_2SO_4$), filtered and concentrated in vacuo. The crude material was recrystallized from a 3:1 hot EtOAc/hexanes (EtOAc/hexanes) mixture.

Yield: 1.52 g (86%).

PREPARATION 2

N-t-Butoxycarbonyl-3-hydroxymethyl-piperidine

To a mixture of 5.0 g (43.4 mmol) of 3-hydroxymethyl-piperidine in 200 ml of $CH_2Cl_2$, was added 6.05 ml (43.4 mmol) of triethylamine ($Et_3N$), followed by 9.8 ml (43.4 mmol) of ($BOC_2O$). The reaction mixture was stirred for 1 hour at room temperature and then washed with 75 ml of a 0.1N hydrochloric acid solution (HCl), dried over $Na_2SO_4$, filtered and then concentrated in vacuo.

Yield: 7.1 g (76%).

PREPARATION 3

2-Bromo-2-methyl-propanamide

To a cold (0° C.) solution of 11 ml (89 mmol) of 2-bromo-2-methyl-propionyl bromide in 25 ml of hexane, was added 24 ml of concentrated ammonium hydroxide ($NH_4OH$), slowly. The reaction mixture was stirred for 20 minutes resulting in the formation of a white precipitate. This precipitate was isolated by filtration, washed three times with water ($H_2O$) and then dried in vacuo to provide 9.1 g of a white solid which was redissolved in 600 ml of hot chloroform ($CHCl_3$) and filtered immediately. The filtrate was combined with 2100 ml of hexane and cooled overnight.

Yield: 6.1 g of crystals (41%).

EXAMPLE 1

A. Methyl O-methyl podocarpate

The compound is prepared from podocarpic acid according to the method of Shaw, JOC, vol. 39, p. 1968, (1974), herein incorporated by reference.

$^1$H NMR (300 MHz, $CDCl_3$) : δ6.98 (d, J=8Hz, 1H); 6.83 (d, J=4Hz, 1H); 6.70 (dd, J=4,8HZ, 1H); 3.78 (s, 3H); 3.67 (s, 3H); 2.80 (m, 2H); 2.25 (m, 3H); 2.0 (m, 2H); 1.6 (m, 2H); 1.42 (m, 1H); 1.30 (s, 3H); 1.12 (m, 1H) and 1.05 (s, 3H).

MS: m/e 288 (M+').

B.

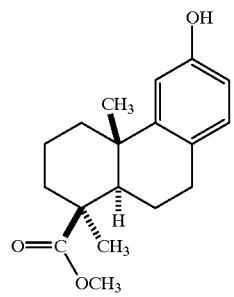

To a solution of 2.0 g (6.62 mmol) of the compound of Example 1A in 10 ml of 1,1,2 trichloroethane, was added 1.0 ml (7.0 mmol) of iodotrimethylsilane. The reaction mixture was heated to 70° C., reacted for 10 minutes, cooled, diluted with 150 ml of a 3:1 hexane/diethyl ether (hexane/$Et_2O$) mixture and then washed with a saturated sodium bicarbonate solution ($NaHCO_3$), dried over $Na_2SO_4$, filtered and concentrated in vacuo.

Yield: 1.51 g of a light tan solid (83%).

$^1$H NMR (300 MHz, $CDCl_3$): δ6.9 (d, J=8Hz, 1H); 6.72 (d, J=4Hz, 1H); 6.58 (dd, J=4,8Hz, 1H); 4.55 (s, 1H); 3.63 (s, 3H); 2.75 (m, 2H); 2.20 (m, 3H); 1.95 (m, 2H); 1.57 (m, 2H); 1.4 (m, 1H); 1.25 (s, 3H); 1.08 (m, 1H) and 1.01 (s, 3H).

MS: m/e 274 (M+).

C.

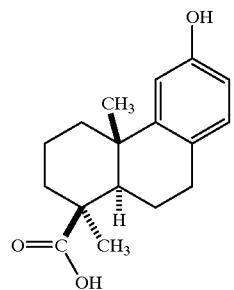

The compound was prepared substantially in accordance with the procedure detailed in Example 1B, using 1.0 g (3.31 mmol) of the compound of Example 1A, 1.0 ml (7.0 mmol) of iodotrimethylsilane and 5 ml of 1,1,2-trichloroethane, with the exception that the saturated NaHCO₃ wash was acidified to pH 2. The desired compound was then extracted with CH₂Cl₂, and the extracts were dried over Na₂SO₄, filtered and then concentrated in vacuo to provide 100 mg of a white solid (11%).

¹H NMR (300 MHz, CDCl₃): δ6.93 (d, J=8Hz, 1H); 6.73 (d, J=4Hz, 1H); 6.6 (dd, J=4,8Hz, 1H); 2.78 (m, 2H); 2.22 (m, 3H); 2.03 (m, 2H); 1.58 (m, 2H); 1.40 (m, 1H); 1.35 (s, 3H); 1.15 (s, 3H) and 1.10 (m, 1H).

Note: 780 mg of the compound of Example 1B was recovered.

EXAMPLE 2

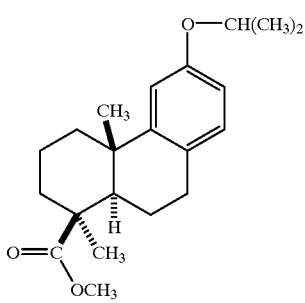

To a solution of 100 mg (0.35 mmol) of the compound of Example 1B in 2 ml of dimethylformamide (DMF), was added 62 mg (0.45 mmol) of K₂CO₃, followed by 42 µl (0.45 mmol) of isopropyl bromide. The reaction mixture was stirred for 2 hours at room temperature and then combined with an additional 180 mg (1.3 mmol) of K₂CO₃ and 130 µl (1.38 mmol) of isopropyl bromide. This mixture was stirred for 24 hours and then diluted with a 1:1 hexane/Et₂O mixture. The resultant layers were separated and the organic layer was washed sequentially with H₂O and 0.1N HCl, dried over Na₂SO₄, filtered and then concentrated in vacuo to provide an oily residue which was purified using flash chromatography (SiO₂, eluent of 5% EtOAc in hexane).

Yield: 51 mg.

¹H NMR (300 MHz, CDCl₃): δ6.95 (d, J=8HZ, 1H); 6.8 (d, J=4Hz, 1H); 6.65 (dd, J=4,8Hz, 1H); 4.47 (m, 1H); 3.64 (s, 3H); 2.78 (m, 2H); 2.22 (m, 3H); 1.97 (m, 2H); 1.58 (m, 2H); 1.40 (m, 1H); 1.32 (d, J=6Hz, 3H); 1.28 (d, J=6Hz, 3H); 1.10 (m, 1H) and 1.07 (s, 3H).

The compounds described in Examples 3–5 were prepared substantially in accordance with the procedure detailed in Example 2, using the shown starting materials.

EXAMPLE 3

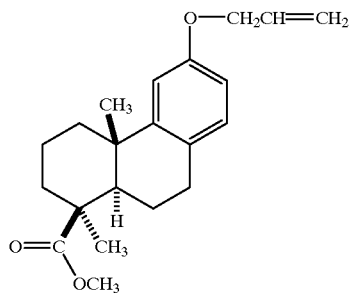

100 mg (0.35 mmol) of the compound of Example 1B, 242 mg (1.75 mmol) of K₂CO₃ and 169 µl (1.40 mmol) of allylbromide in 2 ml of DMF.

Yield: 75 mg (65%).

¹H NMR (300 MHZ, CDCl₃): δ6.97 (d, J=8HZ, 1H); 6.83 (d, J=4HZ, 1H); 6.68 (dd, J=4, 8Hz, 1H); 6.07 (m, 1H); 5.35 (m, 2H); 4.50 (m, 2H); 3.68 (s, 3H); 2.78 (m, 2H); 2.23 (m, 3H); 1.98 (m, 2H); 1.58 (m, 2H); 1.40 (m, 1H); 1.28 (S. 3H); 1.10 (m, 1H) and 1.03 (s, 3H).

EXAMPLE 4

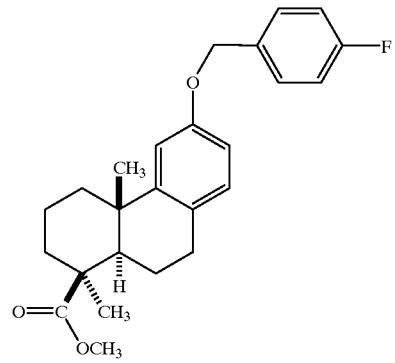

100 mg (0.35 mmol) of the compound of Example 1B, 93 mg (0.67 mmol) of K₂CO₃ and 81 µl (0.68 mmol) of 4-fluorobenzyl chloride in 2 ml of DMF.

Yield: 87 mg (63%).

¹H NMR (300 MHz, CDCl₃): δ7.4 (m, 2H); 7.08 (m, 2H); 6.98 (d, J=8HZ, 1H); 6.88 (d, J=4Hz, 1H); 6.74 (dd, J=4, 8Hz, 1H); 4.98 (s, 2H); 3.68 (s, 3H); 2.78 (m, 2H); 2.23 (m, 3H); 1.96 (m, 2H); 1.58 (m, 2H); 1.40 (m, 1H); 1.28 (s, 3H); 1.10 (m, 1H) and 1.03 (s, 3H).

EXAMPLE 5

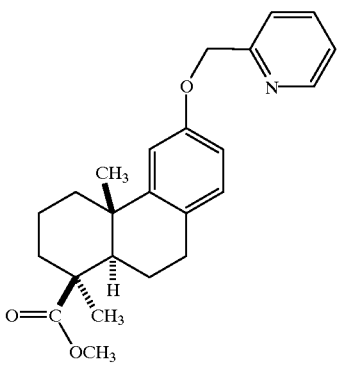

100 mg (0.35 mmol) of the compound of Example 1B, 180 mg (1.30 mmol) of $K_2CO_3$ and 107 mg (0.65 mmol) of 2-picolyl chloride hydrochloride in 2 ml of DMF.

Yield: 35 mg (26%).

$^1$H NMR (300 MHz, CDCl$_3$): δ8.58 (d, J=6Hz, 1H); 7.70 (m, 1H); 7.52 (d, J=6Hz, 1H); 7.20 (m, 1H); 6.95 (d, J=8Hz, 1H); 6.89 (d, J=4Hz, 1H); 6.74 (dd, J=4,8Hz, 1H); 5.18 (s, 2H); 3.64 (s, 3H); 2.77 (m, 2H); 2.20 (m, 3H); 1.97 (m, 2H); 1.55 (m, 2H); 1.27 (s, 3H); 1.08 (m, 1H) and 1.0 (s, 3H).

EXAMPLE 6

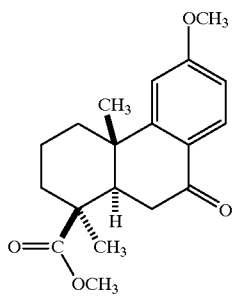

A solution of 6.58 g (65.04 mmol) of chromium trioxide in 70 ml of a 4:1 acetic acid (AcOH)/H$_2$O mixture was added to a mixture of 7.0 g (23.15 mmol) of the compound in Example 1A in 70 ml of AcOH. The reaction mixture was stirred for 18 hours resulting in the precipitation of a solid. This solid was isolated by filtration, washed with H$_2$O, dried in vacuo, redissolved in 75 ml of hot isopropanol (iPrOH) and filtered hot. The filtrate was combined with 225 ml of H$_2$O and cooled to 5° C. for 16 hours to provide crystals which were isolated by filtration, washed with H$_2$O and dried in vacuo at 45° C.

Yield: 6.31 g (86%).

$^1$H NMR (300 MHz, CDCl$_3$): δ8.04 (d, J=8Hz, 1H); 6.88 (d, J=4Hz, 1H); 6.82 (dd, J=8,4Hz, 1H); 3.87 (s, 3H); 3.72 (s, 3H); 3.18 (m, 1H); 2.95 (m, 1H); 2.33 (m, 2H); 2.05 (m, 2H); 1.72 (m, 1H); 1.55 (m, 1H); 1.25 (s, 3H); 1.16 (m, 1H) and 1.11 (s, 3H).

MS: m/e 316 (M+).

Elemental Analysis for C$_{19}$H$_{24}$O$_4$:

Calcd: C, 72.13; H, 7.65;
Found: C, 72.15; H, 7.79.

EXAMPLE 7

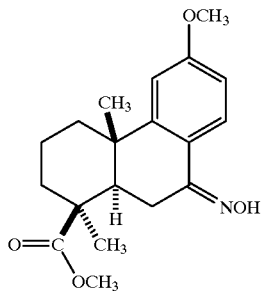

To a solution of 316 mg (1.0 mmol) of the compound of Example 6 in 3.0 ml of absolute ethanol (EtOH), was added 80 mg (1.15 mmol) or hydroxylamine hydrochloride followed by 94 mg (1.15 mmol) of sodium acetate (NaOAc). The reaction mixture was stirred for 65 hours at room temperature and then concentrated in vacuo to provide a solid which was partitioned between Et$_2$O and H$_2$O. The resultant layers were separated and the organic layer was dried over Na$_2$SO$_4$, filtered and concentrated in vacuo to provide a solid. This solid was redissolved in 0.5 ml of Et$_2$O and 8 ml of hot hexane and then cooled to 0° C. resulting in the formation of crystals.

Yield: 282 mg (85%).

$^1$H NMR (300 MHz, CDCl$_3$): δ8.0 (s, 1H); 7.88 (d, J=8Hz, 1H); 6.88 (d, J=4Hz, 1H); 6.78 (dd, J=4,8Hz, 1H); 3.82 (s, 3H); 3.74 (s, 3H); 3.45 (m, 1H); 3.07 (m, 1H); 2.30 (m, 2H); 2.02 (m, 1H); 1.72 (m, 2H); 1.57 (m, 1H); 1.35 (s, 3H); 1.13 (m, 1H) and 1.0 (s, 3H).

MS: m/e 331 (M+).

Elemental Analysis for C$_{19}$H$_{25}$NO$_4$:

Calcd: C, 68.86; H. 7.60; N, 4.23;
Found: C, 69.12; H, 7.69; N, 4.21.

EXAMPLE 8

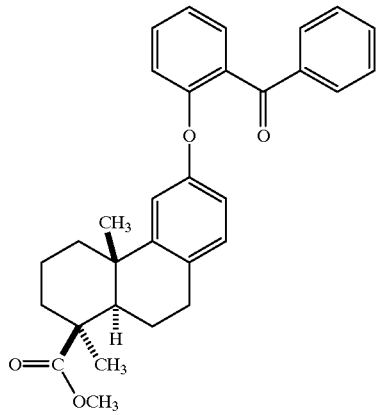

To a hot (100° C.) solution of 426 mg (1.48 mmol) of the compound in Example 1B in 3.0 ml of collidine, was added 0.45 ml (2.66 mmol) of 2-fluorobenzophenone, 415 mg (3.0 mmol) of K$_2$CO$_3$ and 444 mg (5.58 mmol) of copper (II) oxide (CuO). The reaction mixture was then heated to 171° C. and reacted for 16 hours. After cooling, the mixture was diluted with 50 ml of Et$_2$O, washed with 20 ml of 1N HCl, dried over Na$_2$SO$_4$, filtered and then concentrated in vacuo to provide a brown oil. This oil was purified using radial chromatography (4000 micron plate, gradient eluent of 75–100% $CH_2Cl_2$ in hexane).

Yield: 352 mg (51%).

$^1$H NMR (300MHz, $CDCl_3$): δ7.82 (d, J=6Hz, 2H); 7.45 (m, 5H); 7.18 (m, 1H); 6.90 (m, 2H); 6.75 (m, 1H); 6.58 (m, 1H); 3.67 (s, 3H); 2.77 (m, 2H); 2.20 (m, 2H); 1.95 (m, 3H); 1.60 (m, 1H); 1.47 (m, 1H); 1.35 (m, 1H); 1.27 (s, 3H); 1.02 (m, 1H) and 0.95 (s, 3H).

MS: m/e 469 (M+).

Elemental Analysis for $C_{31}H_{32}O_4$:

Calcd: C, 79.46; H, 6.88;
Found: C, 79.53; H, 7.06.

EXAMPLE 9

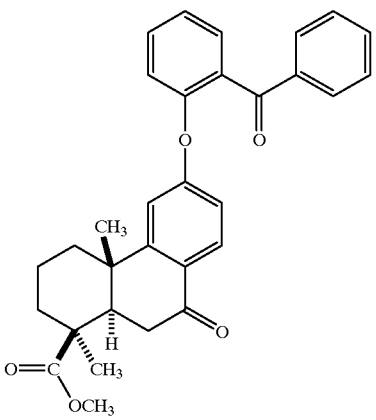

The compound was prepared substantially in accordance with the procedure detailed in Example 6, using 260 mg (0.56 mmol) of the compound of Example 8, 158 mg (1.56 mmol) of chromium trioxide in a 3.05 ml AcOH/0.34 ml $H_2O$ mixture.

Yield: 231 mg (86%).

$^1$H NMR (300 MHz, $CDCl_3$): δ7.90 (d, J=8Hz, 1H); 7.75 (m, 2H); 7.55 (m, 3H); 7.35 (m, 3H); 7.10 (d, J=8Hz, 1H); 6.72 (d, J=4Hz, 1H); 6.62 (dd, J=4,8Hz, 1H); 3.70 (s, 3H); 3.15 (m, 1H); 2.93 (m, 1H); 2.30 (m, 1H); 2.0 (m, 3H); 1.63 (m, 1H); 1.38 (m, 1H); 1.23 (s, 3H); 1.10 (m, 1H) and 1.0 (s, 3H).

MS: m/e 483 (M+).

Elemental Analysis for $C_{31}H_{30}O_5$:

Calcd: C, 77.16; H, 6.27;
Found: C, 76.96; H, 6.29.

EXAMPLE 10

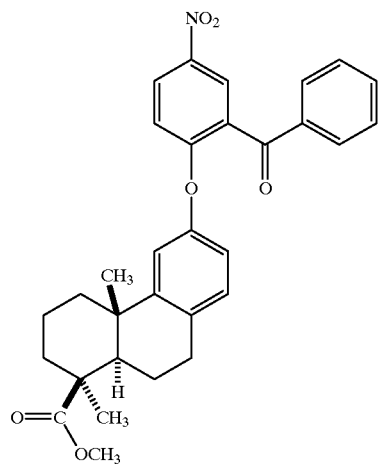

The compound was obtained from the Bader chemical collection, Aldrich Chemical Company.

$^1$H NMR (300 MHz, $CDCl_3$): δ8.38 (d, J=4Hz, 1H) ; 8.23 (dd, J=4,8Hz, 1H); 7.87 (d, J=6Hz, 2H); 7.60 (m, 1H); 7.48 (t, J=6Hz, 2H); 7.03 (d, J=8Hz, 1H); 6.85 (m, 2H); 6.68 (dd, J=4, 8Hz, 1H); 3.64 (s, 3H); 2.80 (m, 2H); 2.22 (m, 2H); 1.98 (m, 3H); 1.55 (m, 2H); 1.33 (m, 1H); 1.26 (s, 3H); 1.07 (m, 1H) and 0.97 (s, 3H).

MS: m/e 513 (M+).:
Elemental Analysis for $C_{31}H_{31}NO_6$:
Calcd: C, 72.50; H, 6.08; N, 2.73
Found: C, 72.40; H, 6.11; N, 2.66.

EXAMPLE 11

A.

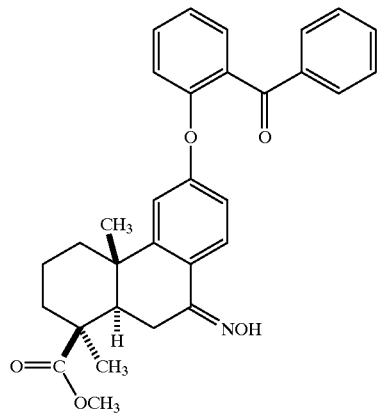

The compound was prepared substantially in accordance with the procedure detailed in Example 7, using 150 mg (0.311 mmol) of the compound of Example 9, 22 mg (0.311 mmol) of hydroxylamine hydrochloride and 26 mg (0.311 mmol) of NaOAc in 3.0 ml of EtOH. The crude material was purified using radial chromatography (2000 micron plate, eluent of 5% EtOAc in $CH_2Cl_2$).

Yield: 138 mg (89%).

$^1$H NMR (300 MHZ, $CDCl_3$): δ7.78 (m, 3H); 7.45 (m, 5H); 7.25 (mn, 1H); 7.0 (d, J=8Hz, 1H); 6.75 (d, J=4Hz, 1H); 6.62 (dd, J=4,8Hz, 1H); 3.70 (s, 3H); 3.4 (m, 1H); 3.02

(m, 1H); 2.25 (m, 1H); 1.98 (m, 2H); 1.63 (m, 2H); 1.37 (m, 1H); 1.30 (s, 3H); 1.08 (m, 1H) and 0.92 (s, 3H).

MS: m/e 497 (M+).

B.

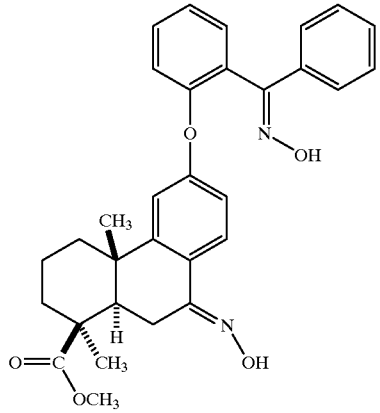

The compound was isolated from the reaction mixture described in Example 11A.

Yield: 5 mg.

¹H NMR (300 MHz, CDCl₃): δ7.65 (d, J=8Hz, 1H); 7.50 (m, 2H); 7.30 (m, 6H); 7.02 (d, J=8Hz, 1H); 6.90 (d, J=4Hz, 1H); 6.78 (dd, J=4,8Hz, 1H); 3.69 (s, 3H); 3.4 (m, 1H); 3.02 (m, 1H); 2.2 (m, 2H); 1.95 (m, 1H); 1.63 (m, 2H); 1.42 (m, 1H); 1.30 (s, 3H); 1.08 (m, 1H) and 0.95 (s, 3H).

MS: m/e 512 (M+).

C.

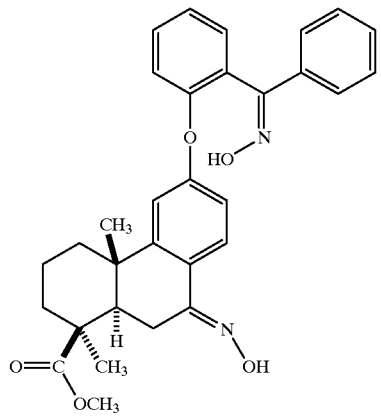

The compound was isolated from the reaction mixture described in Example 11A.

Yield: 4 mg

¹H NMR (300 MHz, CDCl₃): δ7.68 (t, J=8Hz, 1H); 7.50 (m, 1H); 7.30 (m, 5H); 6.85 (m, 3H); 6.58 (d, J=4Hz, 1H); 6.44 (dd, J=4,8Hz, 1H); 3.68 (s, 3H); 3.38 (m, 1H); 3.0 (m, 1H); 2.24 (m, 1H); 2.0 (m, 2H); 1.63 (m, 2H); 1.37 (m, 1H); 1.30 (s, 3H); 1.07 (m, 1H) and 0.92 (s, 3H).

MS: m/e 512 (M+).

EXAMPLE 12

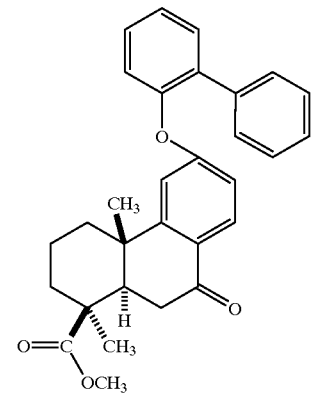

The compound was prepared substantially in accordance with the procedure detailed in Example 8, using 100 mg (0.347 mmol) of the compound of Example 1B, 98 mg (0.423 mmol) of 2-bromobiphenyl, 97 mg (0.702 mmol) of K₂CO₃ and 70 mg (0.88 mmol) of CuO in 1.5 ml of collidine. The crude material was purified using column chromatography (eluent of 30% hexane in CH₂Cl₂).

Yield: 81 mg (53%).

¹H NMR (300 MHz, CDCl₃): δ7.58 (m, 2H); 7.25 (m, 6H); 6.95 (m, 2H); 7.88 (d, J=4Hz, 1H); 6.70 (dd, J=4,8Hz, 1H); 3.64 (s, 3H); 2.78 (m, 2H); 2.15 (m, 3H); 1.95 (m, 2H); 1.55 (m, 2H); 1.35 (m, 1H); 1.25 (s, 3H); 1.05 (m, 1H) and 0.97 (s, 3H).

MS: m/e 440 (M+).

EXAMPLE 13

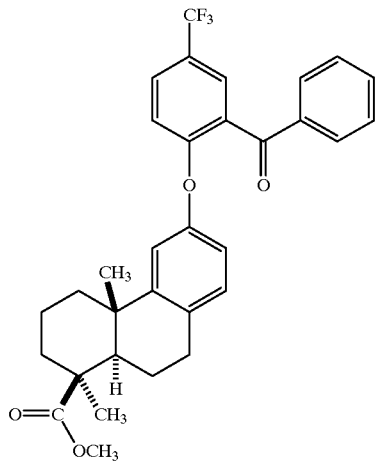

The compound was prepared substantially in accordance with the procedure detailed in Example 8, using 500 mg (1.74 mmol) of the compound of Example 1B, 950 mg (3.54 mmol) of 2-fluoro-5-(trifluoromethyl)benzo-phenone, 500 mg (3.62 mmol) of K₂CO₃, and 350 mg (4.35 mmol) of CuO in 8.0 ml collidine. The crude material was purified using radial chromatography (4000 micron plate, eluent of 25% hexane in CH₂Cl₂).

Yield: 670 mg (72%).

¹H NMR (300 MHz, CDCl₃): δ7.84 (d, J=8HZ, 2H); 7.75 (m, 1H); 7.57 (m, 2H) ; 7.45 (t, J=8Hz, 2H); 6.97 (d, J=8Hz,

1H) ; 6.89 (d, J=8Hz, 1H); 6.80 (d, J=4Hz, 1H); 6.62 (dd, J=4,8Hz, 1H); 3.62 (s, 3H); 2.78 (m, 2H); 2.20 (m, 2H); 1.98 (m, 3H); 1.55 (m, 2H); 1.30 (m, 1H); 1.25 (s, 3H); 1.08 (m, 1H) and 0.96 (s, 3H).

MS: m/e 536 (M+).

EXAMPLE 14

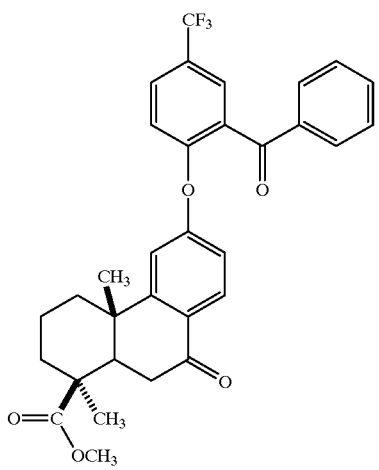

The compound was prepared substantially in accordance with the procedure detailed in Example 6, using 75 mg (0.14 mmol) of the compound of Example 13, 40 mg (0.40 mmol) of chromium trioxide in a 0.85 ml ACOH/0.1 ml H$_2$O mixture.

Yield: 49 mg (64%).

$^1$H NMR (300 MHz, CDCl$_3$): δ7.95 (d, J=6Hz, 1H); 7.77 (m, 3H); 7.58 (m, 1H); 7.42 (t, J=6Hz, 2H); 7.12 (d, J=8Hz, 1H); 6.80 (d, J=4Hz, H); 6.70 (dd, J=4,8Hz, 1H); 3.68 (s, 3H); 3.18 (m, 1H); 2.95 (m, 1H); 2.30 (m, 1H); 2.0 (m, 3H); 1.67 (m, 1H); 1.40 (m, 1H); 1.25 (s, 3H); 1.12 (m, 1H) and 1.03 (s, 3H).

MS: m/e 550 (M+).

EXAMPLE 15

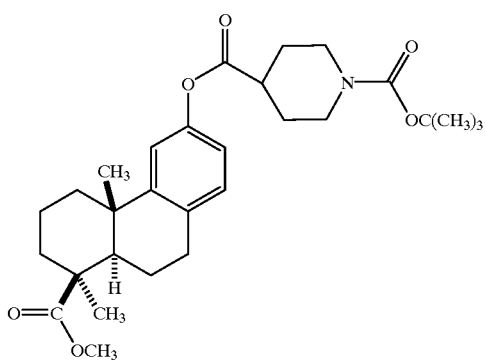

To a solution of 200 mg (0.694 mmol) of the compound of Example 1B in 5.0 ml of CH$_2$Cl$_2$, was added 0.372 ml (2.10 mmol) of diisopropylethylamine and 86 mg (0.70 mmol) of 4-dimethylamino pyridine followed by a mixture containing 480 mg (2.10 mmol) of the compound of Preparation 1, 0.207 ml (2.56 mmol) of pyridine and 0.170 ml (2.33 mmol) of thionyl chloride in 5.0 ml of CH$_2$Cl$_2$. The reaction mixture was stirred at room temperature for 30 minutes, diluted with CH$_2$Cl$_2$, washed sequentially with 1N HCl and a saturated NaHCO$_3$ solution, dried over Na$_2$SO$_4$, filtered and then concentrated in vacuo to provide a tan foam. This foam was purified using radial chromatography (2000 micron plate, gradient eluent of 10% hexane in CH$_2$Cl$_2$ to 25% EtOAc in CH$_2$Cl$_2$).

Yield: 280 mg (81%).

$^1$H NMR (300 MHz, CDCl$_3$): δ7.02 (d, J=8HZ, 1H); 6.90 (d, J=4HZ, 1H); 6.77 (dd, J=4,8HZ, 1H): 4.08 (m, 2H); 3.65 (s, 3H) ; 2.90 (m, 3H) ; 2.75 (m, 3H); 2.20 (m, 3H) ; 1.98 (m, 4H); 1.78 (m, 2H); 1.6 (m, 1H); 1.45 (s, 9H); 1.40 (m, 1H); 1.28 (s, 3H); 1.08 (m, 1H) and 1.0 (s, 3H).

MS: m/e 499 (M+).

EXAMPLE 16

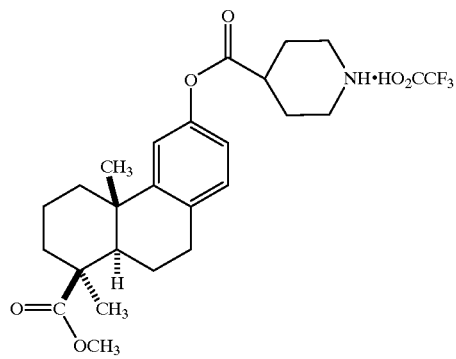

To a solution of 250 mg (0.50 mmol) of the compound in Example 15 in 1.0 ml of CH$_2$Cl$_2$, was added 0.160 ml (1.0 mmol) of triethylsilane and 1.0 ml of trifluoroacetic acid (CF$_3$COOH). The reaction mixture was stirred for 30 minutes at room temperature, diluted with 15 ml of acetonitrile (CH$_3$CN) and then concentrated in vacuo to provide 231 mg of a tan solid. Then, 200 mg of this solid was dissolved in 20 ml of CH$_2$Cl$_2$, washed with a saturated NaHCO$_3$ solution, dried over Na$_2$SO$_4$, filtered and concentrated in vacuo.

Yield: 170 mg (98%).

$^1$H NMR (300 MHZ, CDCl$_3$):δ7.02 (d, J=8Hz, 1H); 6.92 (d, J=4Hz, 1H); 6.78 (dd, J=4,8Hz, 1H); 3.63 (s, 3H); 3.17 (m, 2H); 2.75 (m, 5H); 2.20 (m, 3H); 1.98 (m, 4H); 1.75 (m, 2H); 1.58 (m, 2H); 1.40 (m, 1H); 1.27 (s, 3H); 1.08 (m, 1H) and 1.0 (s, 3H).

MS: m/e 400 (M+).

EXAMPLE 17

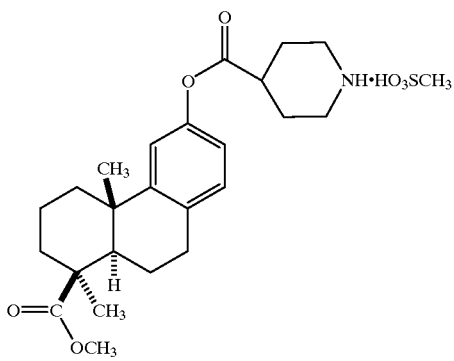

To a solution of 160 mg (0.4 mmol) of the free base of the compound of Example 16 in 4.0 ml of a 3:1 Et$_2$O/hexane mixture, was added 26 µl (0.4 mmol) of methanesulfonic acid.

Yield: 198 mg of a solid (quantitative).

$^1$H NMR (300 MHz, CDCl$_3$):δ8.43 (bs, 1H); 8.20 (bs, 1H); 6.75 (d, J=8Hz, 1H); 6.60 (d, J=4Hz, 1H); 6.45 (dd, J=4,8Hz, 1H); 3.55 (s, 3H); 3.20 (m, 2H); 2.90 (m, 2H); 2.58 (m, 3H); 2.30 (s, 3H); 2.10 (m, 3H); 1.93 (m, 4H); 1.65 (m, 2H); 1.47 (m, 2H); 1.24 (m, 1H); 1.17 (s, 3H); 1.08 (m, 1H) and 0.88 (s, 3H).

EXAMPLE 18

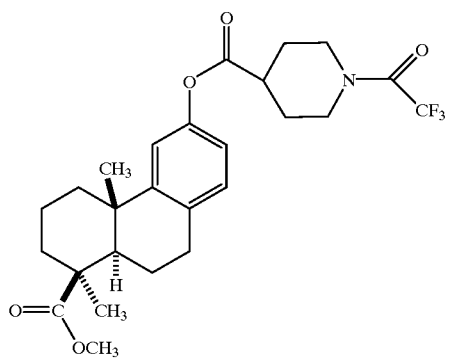

To a solution of 160 mg (0.324 mmol) of the compound in Example 17 in 3.0 ml CH$_2$Cl$_2$, was added 100 µl (0.712 mmol) of Et$_3$N and 50 µl (0.356 mmol) of trifluoroacetic anhydride. The reaction mixture was stirred for 15 minutes at room temperature, diluted with 30 ml of EtOAc, sequentially washed with 10 ml of 0.2N HCl, 10 ml of a saturated NaHCO$_3$ solution and 10 ml brine, dried over NaSO$_4$, filtered and then concentrated in vacuo.

Yield: 130 mg (81%).

$^1$H NMR (300 MHz, CDCl$_3$):δ7.03 (d, J=8Hz, 1H); 6.91 (d, J=4Hz, 1H); 6.78 (dd, J=4,8Hz, 1H); 4.37 (m, 1H); 4.0 (m, 1H); 3.64 (s, 3H); 3.35 (m, 1H); 3.15 (m, 1H); 2.82 (m, 3H); 2.28 (m, 1H); 2.18 (m, 4H); 1.95 (m, 3H); 1.50 (m, 4H); 1.25 (s, 3H); 1.08 (m, 1H) and 1.0 (s, 3H).

EXAMPLE 19

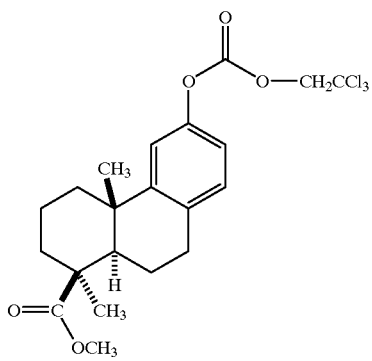

To a solution of 470 mg (1.63 mmol) of the compound of Example 1B in 12.0 ml of a 1:2 Et$_2$O/CH$_2$Cl$_2$ mixture, was added 0.237 ml (1.70 mmol) of Et$_3$N and 0.224 ml (1.63 mmol) of 2,2,2-trichloroethyl chloroformate. The reaction mixture was stirred at room temperature for 20 minutes, diluted with 50 ml of Et$_2$O, sequentially washed with 15 ml of H$_2$O, 15 ml of 0.2N HCl, 15 ml of NaCO$_3$ and 15 ml of brine, dried over Na$_2$SO$_4$, filtered and then concentrated in vacuo to provide an oily residue. This residue was purified using flash chromatography (SiO$_2$, eluent of 30% hexane in CH$_2$Cl$_2$).

Yield: 620 mg (82%).

$^1$H NMR (300MHz, CDCl$_3$):δ7.08 (m, 2H); 6.93 (m, 1H); 4.87 (s, 2H); 3.67 (s, 3H); 2.90 (m, 1H); 2.78 (m, 1H); 2.23 (m, 3H); 2.00 (m, 2H); 1.58 (m, 2H); 1.42 (m, 1H); 1.30 (s, 3H); 1.12 (m, 1H) and 1.03 (s, 3H).

MS: m/e 463 (M+).

EXAMPLE 20

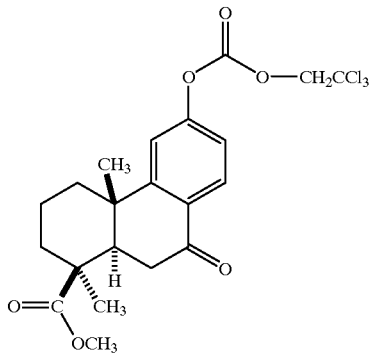

The compound was prepared substantially in accordance with the procedure detailed in Example 6, using 620 mg (1.33 mmol) of the compound of Example 19, 405 mg (4.0 mmol) of chromium trioxide in a 8.1 ml AcOH/0.9 ml H$_2$O.

Yield: 540 mg (85%).

$^1$H NMR (300MHz, CDCl$_3$): δ8.02 (d, J=8Hz, 1H); 6.90 (d, J=4Hz, 1H); 6.80 (dd, J=4,8Hz, 1H); 5.02 (s, 2H); 3.70 (s, 3H); 3.18 (m, 1H); 2.83 (m, 1H); 2.30 (m, 2H); 2.03 (m, 2H); 1.70 (m, 1H); 1.50 (m, 1H); 1.25 (s, 3H); 1.10 (m, 1H) and 1.02 (s, 3H).

EXAMPLE 21

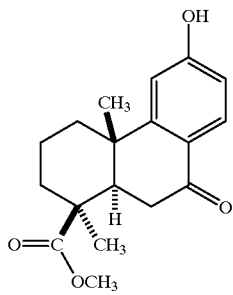

To a solution of 5.3 g (11.1 mmol) of the compound of Example 20 in 90 ml of a 1:2 AcOH/EtOH mixture, was added 10.0 g (153 mmol) of zinc dust. The mixture was reacted for 5 minutes at 80° C. and then cooled to room temperature, filtered and concentrated in vacuo to provide a solid. This solid was slurried in $CH_2Cl_2$ and filtered. The filtrate was dried in vacuo to provide a solid which was diluted with 100 ml of hot $CHCl_3$ and filtered into 700 ml of hexane. The compound was then crystallized from this solution.

Yield: 3.31 g (99%).

$^1$H NMR (300MHz, $CDCl_3$):δ7.82 (d, J=8HZ, 1H): 6.80 (d, J=4HZ, 1H); 6.70 (dd, J=4,8Hz, 1H); 3.68 (s, 3H); 3.15 (m, 1H); 2.82 (m, 1H); 2.26 (m, 2H); 2.03 (m, 2H); 1.67 (m, 1H); 1.50 (m, 1H); 1.20 (s, 3H); 1.17 (m, 1H) and 1.08 (s, 3H).

MS: m/2 302 (M+).

EXAMPLE 22

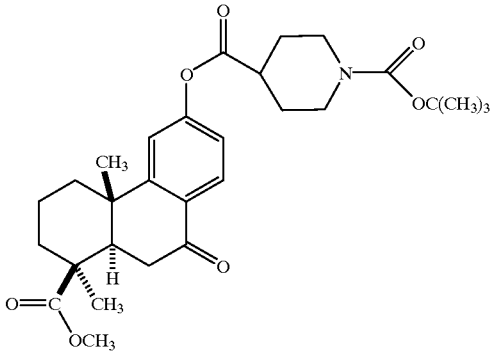

The compound was prepared substantially in accordance with the procedure detailed in Example 15, using 440 mg (1.46 mmol) of the compound of Example 21, 0.645 ml (3.7 mmol) of diisopropylethylamine, 179 mg (1.46 mmol) of 4-dimethylaminopyridine, 845 mg (3.7 mmol) of the compound of Preparation 1, 0.365 ml (4.5 mmol) of pyridine and 0.300 (4.1 mmol) of thionyl chloride in 45 ml of $CH_2Cl_2$.

Yield: 380 mg (51%).

$^1$H NMR (300MHz, $CDCl_3$):δ8.08 (d, J=8Hz, 1H); 7.10 (d, J=4Hz, 1H); 7.0 (dd, J=4,8Hz, 1H); 4.08 (m, 2H); 3.71 (s, 3H); 3.22 (m, 1H); 2.95 (m, 3H); 2.72 (m, 1H); 2.30 (m, 2H); 2.05 (m, 4H); 1.75 (m, 3H) 1.47 (s, 9H); 1.26 (s, 3H); 1.16 (m, 1H) and 1.14 (s, 3H).

MS: m/e 513 (M+).

EXAMPLE 23

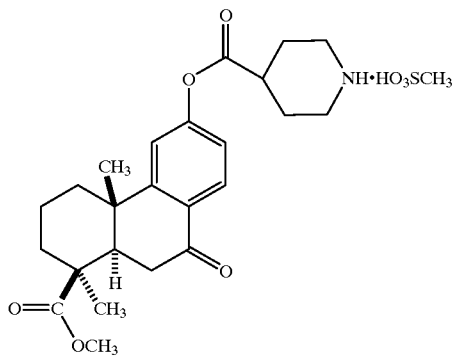

The compound was prepared substantially in accordance with the procedures detailed in Examples 16 and 17, using 160 mg (0.31 mmol) of the compound of Example 22, 0.1 ml (0.63 mmol) of triethylsilane, 2.0 ml of a 1:1 $CF_3COOH/CH_2Cl_2$ mixture and 20 μl (0.31 mmol) of methanesulfonic acid.

Yield: 153 mg (97%).

$^1$H NMR (300MHz, $CDCl_3$) δ8.05 (m, 1H); 7.10 (m, 1H); 7.0 (m, 1H); 3.65 (s, 3H); 3.18 (m, 3H); 2.95 (m, 2H); 2.65 (m, 3H); 2.27 (bs, 3H); 2.05 (m, 5H); 1.75 (m, 3H); 1.50 (m, 1H); 1.23 (s, 3H); 1.18 (m, 1H) and 1.10 (s, 3H).

EXAMPLE 24

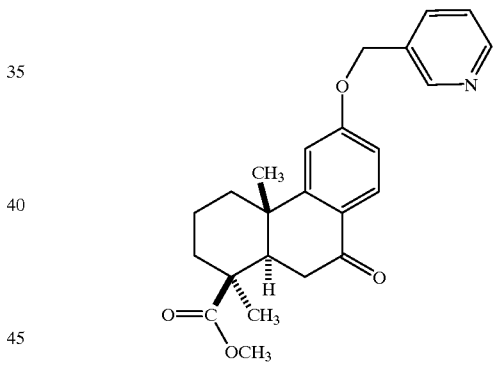

To a solution of 250 mg (0.83 mmol) of the compound from Example 21 in 8.0 ml of tetrahydrofuran (THF), was added 85 μl (0.87 mmol) of 3-pyridylcarbinol, 236 mg (0.9 mmol) of triphenylphosphine and 142 μl (0.9 mmol) of diethyl azodicarboxylate. The reaction mixture was heated to 65° C. and reacted for 10 minutes, cooled to room temperature and concentrated in vacuo to provide an oily residue which was triturated in $Et_2O$ and filtered. The filtrate was washed sequentially with $H_2O$ and a 0.1N $K_2CO_3$ solution, dried over $Na_2SO_4$, filtered and concentrated in vacuo.

Yield: 198 mg of a tan solid (61%).

$^1$H NMR (300MHz, $CDCl_3$):δ8.70 (s, 1H); 8.60 (d, J=4Hz, 1H); 8.05 (d, J=8Hz, 1H); 7.78 (d, J=8Hz, 1H); 7.35 (m, 1H); 6.95 (d, J=4Hz, 1H); 6.90 (dd, J=4.8Hz, 1H); 5.13 (s, 2H); 3.70 (s, 3H); 3.18 (m, 1H); 2.95 (m, 1H); 2.30 (m, 2H); 2.04 (m, 2H); 1.70 (m, 1H); 1.53 (m, 1H); 1.25 (s, 3H); 1.13 (m, 1H) and 1.10 (s, 3H).

MS: m/e 393 (M+).

EXAMPLE 25

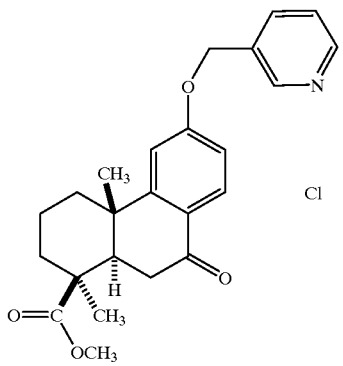

To a solution of 38 mg (0.097 mmol) of the compound from Example 24 in 2.2 ml of a 1:1:0.2 $CH_3CN/Et_2O/$ hexane mixture, was added 0.1 ml of a $HCl/CH_3CN$ solution (1.0 ml of concentrated HCl in 11.0 ml of $CH_3CN$) which resulted in the formation of a precipitate which was isolated by filtration.

Yield: 40 mg (96%).

$^1$H NMR (300MHz, $CDCl_3$): δ8.80 (bs, 1H); 8.65 (s, 1H); 8.55 (d, J=4Hz, 1H); 7.98 (d, J=8HZ, 1H); 7.72 (d, J=8Hz, 1H); 7.30 (m, 1H); 6.90 (d, J=4Hz, 1H); 6.83 (dd, J=4,8Hz, 1H); 5.10 (s, 2H); 3.68 (s, 3H); 3.16 (m, 1H); 2.91 (m, 1H); 2.27 (m, 2H); 2.0 (m, 2H); 1.68 (m, 1H); 1.50 (m, 1H); 1.23 (s, 3H); 1.10 (m, 1H) and 1.03 (s, 3H).

MS: m/e 393 (M+-HCl).

EXAMPLE 26

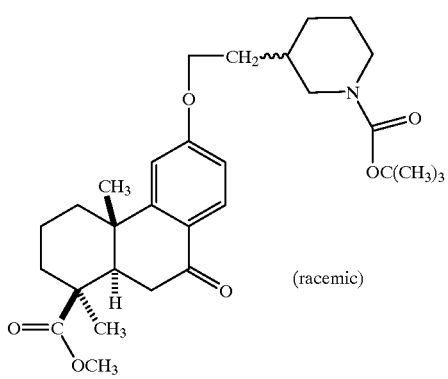

(racemic)

The compounds were prepared substantially in accordance with the procedure detailed in Example 24, using 300 mg (0.992 mmol) of the compound of Example 21, 214 mg (0.992 mmol) of the compound of Preparation 2, 275 mg (1.05 mmol) of triphenylphosphine and 0.165 ml (1.05 mmol) of diethylazodicarboxylate in 9.0 ml of THF. The crude material was purified using radial chromatography (2000 micron plate, eluent of 5% EtOAc in $CH_2Cl_2$).

Yield: 477 mg (96%).

$^1$H NMR (300MHz, $CDCl_3$):δ8.01 (d, J=8Hz, 1H); 6.84 (d, J=4Hz, 1H); 6.78 (dd, J=4,8Hz, 1H); 3.85 (m, 3H); 3.70 (s, 3H); 3.17 (m, 1H); 2.92 (m, 2H); 2.30 (m, 2H); 2.02 (m, 3H); 1.88 (m, 1H); 1.68 (m, 3H); 1.50 (m, 4H); 1.46 (s, 9H); 1.26 (s, 3H); 1.13 (m, 1H) and 1.10 (s, 3H).

MS: m/e 499 (M+).

EXAMPLE 27

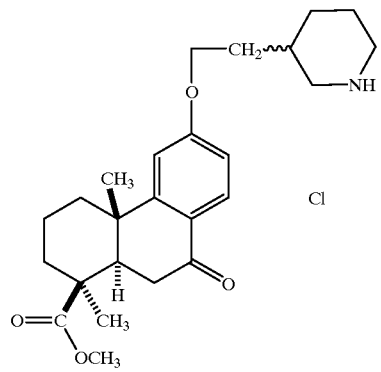

The compounds were prepared substantially in accordance with the procedures detailed in Examples 16 and 25, using 378 mg (0.76 mmol) of the compound of Example 26, 0.20 ml (1.26 mmol) of triethylsilane, 5.0 ml of a 2:3 $CH_2Cl_2/CF_3COOH$ mixture and 0.714 ml of a $HCl/CH_3CN$ solution (1.0 ml of concentrated HCl in 11.0 ml of $CH_3CN$).

Yield: 287 mg (87%).

$^1$H NMR (300MHz, $CDCl_3$):δ9.02 (m, 2H); 7.80 (d, J=8Hz, 1H); 6.95 (s, 1H); 6.87 (d, J=8Hz, 1H); 3.97 (m, 2H); 3.60 (s, 3H) ; 3.22 (m, 1H) ; 3.03 (m, 1H); 3.74 (m, 3H) ; 2.20 (m, 5H); 1.75 (m, 5H); 1.35 (m, 2H); 1.18 (s, 3H); 1.13 (m, 1H) and 1.0 (s, 3H).

MS: m/e 399 (M+-HCl).

EXAMPLE 28

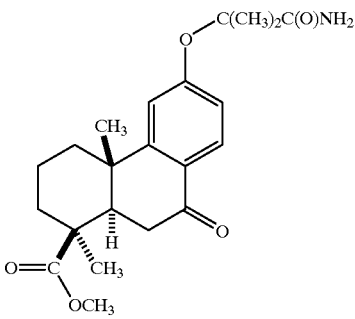

To a solution of 1.2 g (3.97 mmol) of the compound of Example 21 in 50 ml of dioxane, was slowly added 210 mg (4.37 mmol) of a 50% dispersion of sodium hydride (NaH) in mineral oil, with stirring, followed by 663 mg (3.97 mmol) of the compound from Preparation 3. The mixture was heated to 100° C. and reacted for 6 hours, then cooled and combined with 5.0 ml of 1N sodium hydroxide (NaOH), followed by 200 ml of EtOAc. The resultant layers were separated and the organic layer was dried over $Na_2SO_4$, filtered and concentrated in vacuo.

Yield: 500 mg (32%).

$^1$H NMR (300MHz, $CDCl_3$):δ7.98 (d, J=8Hz, 1H); 6.90 (d, J=4Hz, 1H); 6.83 (dd, J=4,8Hz, 1H); 6.40 (bs, 1H); 5.6 (bs, 1H); 3.70 (s, 3H); 3.18 (m, 1H); 2.95 (m, 1H); 2.28 (m, 2H); 2.02 (m, 2H); 1.70 (m, 1H); 1.61 (s, 3H); 1.58 (s, 3H); 1.48 (m, 1H); 1.25 (s, 3H); 1.13 (m, 1H) and 1.10 (s, 3H).

EXAMPLE 29

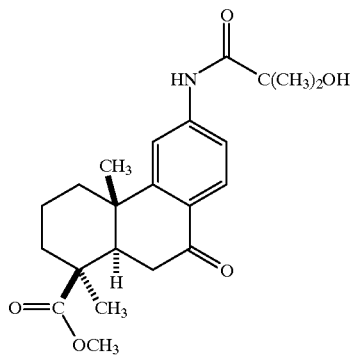

To a solution of 480 mg (1.23 mmol) of the compound of Example 28 in a mixture of 15.0 ml DMF and 2.0 ml of 1,3-dimethyl-3,4,5,6-tetrahydro-2(1H)-pyrimidinone, was added 66 mg (1.36 mmol) of a 50% dispersion of NaH in mineral oil. The reaction mixture was refluxed for 5 minutes and then cooled to room temperature. To the mixture, was added 10 ml of a saturated $NaHCO_3$ solution followed by 100 ml of EtOAc. The resultant layers were separated and the organic layer was sequentially washed with $H_2O$ and 0.2N HCl, dried over $Na_2SO_4$, filtered and concentrated in vacuo.

Yield: 380 mg of a tan solid (79%).

$^1$H NMR (300MHz, $CDCl_3$):δ8.90 (bs, 1H); 8.02 (d, J=8Hz, 1H); 7.92 (d, J=4Hz, 1H); 7.32 (dd, J=4,8Hz, 1H); 3.70 (s, 3H); 3.22 (m, 1H); 2.97 (m, 1H); 2.35 (m, 3H); 2.05 (m, 2H); 1.70 (m, 1H) ; 1.57 (s, 6H); 1.52 (m, 1H) ; 1.25 (s, 3H); 1.15 (m, 1H) and 1.12 (s, 3H).

MS: m/e 387 (M+).

EXAMPLE 30

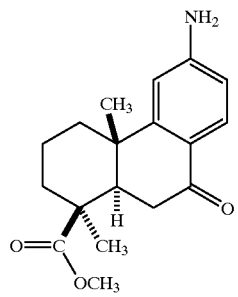

To a solution of 100 mg (0.257 mmol) of the compound of Example 29 in 5.0 ml of dioxane, was added 0.8 ml of 5N HCl.

The resultant mixture was heated to 100° C., reacted for 2 hours, cooled and then diluted with 50 ml of $CH_2Cl_2$. The resultant layers were separated and the organic layer was washed with a saturated $NaHCO_3$ solution dried over $Na_2SO_4$, filtered and concentrated in vacuo to provide a solid. This solid was purified using radial chromatography (1000 micron plate, eluent of 20% EtOAc in $CH_2Cl_2$).

Yield: 46 mg (60%).

$^1$H NMR (300MHz, $CDCl_3$):δ7.90 (d, J=8Hz, 1H); 6.55 (m, 2H); 4.12 (bs, 2H); 3.70 (s, 3H); 3.15 (m, 1H); 2.90 (m, 1H); 2.27 (m, 2H); 2.02 (m, 2H); 1.67 (m, 1H); 1.50 (m, 1H); 1.22 (s, 3H); 1.12 (m, 1H) and 1.08 (s, 3H).

MS: m/e 301 (M+).

EXAMPLE 31

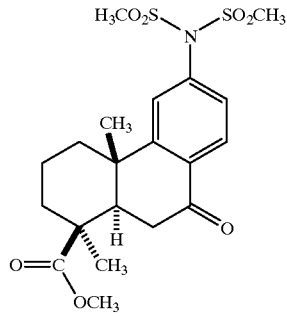

To a solution of 25 mg (0.083 mmol) of the compound of Example 30 in 1.0 ml $CH_2Cl_2$, was slowly added 24 μl (0.172 mmol) of $Et_3N$ and 13 μl (0.168 mmol) of methanesulfonyl chloride. The reaction mixture was diluted with EtOAc and washed sequentially with 0.2N HCl and a saturated $NaHCO_3$ solution, dried over $Na_2SO_4$, filtered and concentrated in vacuo.

Yield: 31 mg of a white solid (82%).

$^1$H NMR (300MHz, $CDCl_3$):δ8.13 (d, J=8Hz, 1H); 7.4 (s, 1H); 7.30 (d, J=8Hz, 1H); 3.73 (s, 3H); 3.40 (s, 6H); 3.25 (m, 1H); 3.03 (m, 1H); 2.35 (m, 2H); 2.05 (m, 2H): 1.75 (m, 1H); 1.58 (m, 1H); 1.27 (s, 3H); 1.16 (m, 1H) and 1.15 (s, 3H).

EXAMPLE 32

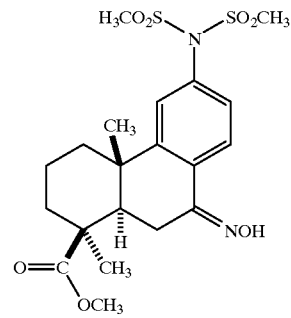

The compound was prepared substantially in accordance with the procedure detailed in Example 7, using 24 mg (0.053 mmol) of the compound of Example 31, 4.6 mg (0.066 mmol) of hydroxylamine hydrochloride and 5.4 mg (0.066 mmol) of NaoAc in 1.0 ml of EtOH. The crude material was purified using radial chromatography (1000 micron plate, eluent of 5% EtOAc in $CH_2Cl_2$).

Yield: 20 mg (80%).

$^1$H NMR (300MHz, $CDCl_3$): δ8.0 (d, J=8Hz, 1H); 7.78 (s, 1H) 7.30 (d, J=4Hz, 1H); 7.18 (dd, J=4,8Hz, 1H); 3.72 (s, 3H); 3.42 (m, 1H); 3.40 (s, 6H); 3.10 (m, 1H); 2.32 (m, 2H): 2.02 (m, 1H); 1.73 (m, 2H); 1.55 (m, 1H); 1.33 (s, 3H); 1.13 (m, 1H) and 1.04 (s, 3H).

MS: m/e 472 (M+).

EXAMPLE 33

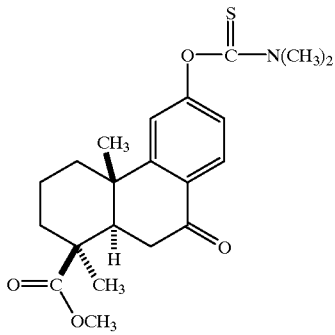

To a solution of 1.5 g (4.96 mmol) of the compound of Example 21 and 278 mg (4.96 mmol) of potassium hydroxide (KOH) in 50 ml of $H_2O$, was added 817 mg (6.6 mmol) of dimethylthiocarbamoyl chloride. The reaction mixture was stirred rapidly for 15 minutes. The reaction mixture was diluted with 100 ml of $Et_2O$ and the organic phase was separated, dried over $Na_2SO_4$, filtered and concentrated in vacuo to provide an oily solid which was triturated in MeOH and then isolated by filtration.

Yield: 1.45 g (75%).

$^1$H NMR (300MHz, $CDCl_3$):δ8.10 (d, J=8Hz, 1H); 7.13 (d, J=4Hz, 1H); 7.0 (dd, J=4,8Hz, 1H); 3.73 (s, 3H); 3.44 (s, 3H); 3.33 (s, 3H); 3.22 (m, 1H); 2.98 (m, 1H); 2.30 (m, 2H); 2.05 (m, 2H); 1.62 (m, 2H); 1.28 (s, 3H); 1.17 (m, 1H) and 1.14 (s, 3H).

MS: m/e 389 (M+).

EXAMPLE 34

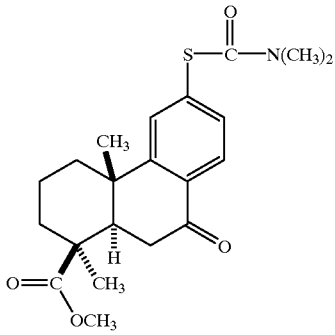

The compound was prepared by melting 300 mg (0.77 mmol) of the compound of Example 33 in a flask under nitrogen ($N_2$). The liquified residue was cooled to provide 300 mg of a glassy solid (quantitative).

$^1$H NMR (300MHz, $CDCl_3$): δ8.02 (d, J=8Hz, 1H); 7.58 (d, J=4Hz, 1H); 7.42 (dd, J=4, 8Hz, 1H); 3.70 (s, 3H); 3.22 (m, 1H); 3.04 (m, 7H); 2.35 (m, 2H); 2.05 (m, 2H); 1.70 (m, 1H); 1.57 (m, 1H); 1.27 (s, 3H); 1.16 (s, 3H) and 1.14 (m, 1H).

MS: m/e 390 (M+).

EXAMPLE 35

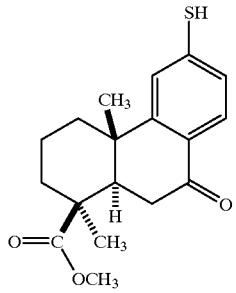

To a solution of 480 mg (1.23 mmol) of the compound of Example 34 in 15.0 ml of MeOH, was added 689 mg (12.3 mmol) of KOH. The reaction mixture was refluxed for 20 minutes, cooled to room temperature, and diluted with 80 ml of $H_2O$ and 100 ml of $Et_2O$. The resulting layers were separated and the aqueous layer was acidified with 4.0 ml of 5N HCl and then combined with 100 ml of $CH_2Cl_2$. The resultant layers were separated and the organic layer was dried over $Na_2SO_4$, filtered and concentrated in vacuo.

Yield: 370 mg of a tan solid (94%).

$^1$H NMR (300MHz, $CDCl_3$):δ7.90 (d, J=8Hz, 1H); 7.24 (d, J=4Hz, 1H); 7.15 (d, J=8Hz, 1H); 3.70 (s, 3H); 3.60 (s, 1H); 3.18 (m, 1H); 2.95 (m, 1H); 2.32 (m, 2H); 2.02 (m, 2H); 1.72 (m, 1H); 1.50 (m, 1H); 1.25 (s, 3H); 1.14 (m, 1H) and 1.10 (s, 3H).

MS: m/e 318 (M+).

EXAMPLE 36

A.

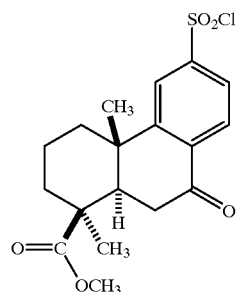

To a 0° C. solution of 320 mg (1.01 mmol) of the compound of Example 35 in 20.0 ml of $CH_3CN$ was added 253 mg (2.5 mmol) of potassium nitrate ($KNO_3$) and 0.201 ml (2.5 mmol) of sulfuryl chloride. The reaction mixture was stirred for 30 minutes at 0° C., diluted with 100 ml of $Et_2O$ and washed with 30 ml of $H_2O$. The organic phase was separated, dried over $Na_2SO_4$, filtered and concentrated in vacuo to provide 280 mg of a crude yellow solid. This solid was purified using radial chromatography (1000 micron plate, eluent of 2% EtOAc in $CH_2Cl_2$).

Yield: 105 mg (27%).

$^1$H NMR (300MHz, $CDCl_3$):δ8.23 (d, J=8Hz, 1H); 8.08 (d, J=4Hz, 1H); 7.93 (dd, J=4,8Hz, 1H); 3.74 (s, 3H); 3.33 (m, 1H); 3.10 (m, 1H); 2.40 (m, 2H); 2.03 (m, 2H); 1.75 (m,

1H); 1.55 (m, 1H); 1.28 (s, 3H); 1.18 (s, 3H) and 1.16 (m, 1H).

MS: m/e 385 (M+).

B.

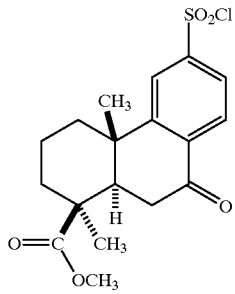

The compound was isolated from the reaction mixture detailed in Example 36A.

Yield: 135 mg.

¹H NMR (300MHz, CDCl₃):δ8.02 (m, 3H); 5.8 (d, J=8Hz, 1H); 3.75 (s, 3H); 2.35 (m, 3H); 1.85 (m, 3H); 1.53 (m, 1H); 1.50 (s, 3H) and 0.96 (s, 3H).

MS: m/e 418 (M+).

EXAMPLE 37

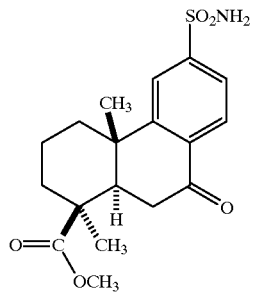

To a solution of 100 mg (0.26 mmol) of the compound of Example 36A in 1.0 ml of THF, was added 60 μl (0.84 mmol) of concentrated NH₄OH. The reaction mixture was diluted with 20.0 ml CH₂Cl₂, washed with 10.0 ml H₂O, dried over Na₂SO₄, filtered and concentrated in vacuo.

Yield: 90 mg (95%).

¹H NMR (300MHz, CDCl₃): δ8.13 (d, J=8Hz, 1H); 8.0 (d, J=4Hz, 1H); 7.80 (dd, J=4,8Hz, 1H); 5.01 (s, 2H); 3.73 (s, 3H); 3.27 (m, 1H); 3.02 (m, 1H); 2.38 (m, 2H); 2.02 (m, 2H); 1.73 (m, 1H); 1.54 (m, 1H); 1.27 (s, 3H); 1.17 (m, 1H) and 1.13 (s, 3H).

EXAMPLE 38

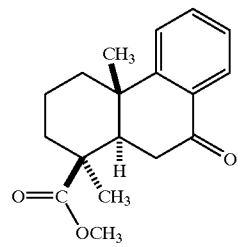

To a solution of 50 mg (0.157 mmol) of the compound of Example 35 in 15.0 ml of EtOH, was added 100 mg of Rainey nickel catalyst. The reaction mixture was shaken under hydrogen gas (60 psi) at room temperature for 3 hours and then filtered and concentrated in vacuo. The crude material was purified using radial chromatography (1000 micron plate, gradient eluent of 1–10% EtOAc in CH₂Cl₂).

Yield: 15 mg (33%).

¹H NMR (300MHz, CDCl₃): δ8.03 (d, J=8Hz, 1H); 7.54 (t, J=8Hz, 1H); 7.40 (d, J=8Hz, 1H); 7.31 (d, J=8Hz, 1H); 3.72 (s, 3H); 3.22 (m, 1H); 3.0 (m, 1H); 2.37 (m, 2H); 2.03 (m, 2H); 1.73 (m, 1H); 1.55 (m, 1H); 1.26 (s, 3H); 1.14 (m, 1H) and 1.12 (s, 3H).

MS: m/e 286 (M+).

EXAMPLE 39

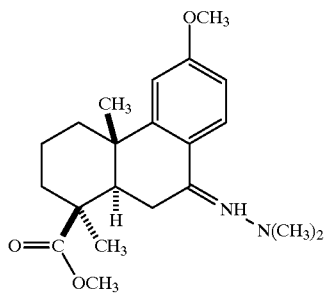

To a solution of 200 mg (0.632 mmol) of the compound of Example 6 in 2.5 ml of EtOH was added 43 μl (0.75 mmol) of ACOH, and 396 μl (5.2 mmol) of 1,1-dimethylhydrazine. The reaction mixture was heated to 80° C. and reacted for 4 hours, concentrated in vacuo, diluted with Et₂O, washed with H₂O, dried over Na₂SO₄, filtered and then concentrated in vacuo to provide an oil. This oil was purified using radial chromatography (2000 micron plate, eluent of 8% EtOAc in CH₂Cl₂)

Yield: 145 mg (64%).

¹H NMR (300MHz, CDCl₃):δ8.13 (d, J=8Hz, 1H); 6.81 (d, J=4Hz, 1H); 6.74 (dd, J=4,8Hz, 1H); 3.81 (s, 3H); 3.71 (s, 3H); 3.61 (m, 1H); 2.78 (m, 1H); 2.60 (s, 6H); 2.28 (m, 2H); 1.72 (m, 2H); 1.47 (m, 1H); 1.32 (s, 3H); 1.12 (m, 1H) and 1.06 (s, 3H).

MS: m/e 358 (M+).

Elemental Analysis for C₂₁H₃₀N₂O₃:

Calcd: C, 70.36; H, 8.44; N, 7.81;

Found: C, 70.30; H, 7.91; N, 8.00.

EXAMPLE 40

To a solution of 98 mg (0.273 mmol) of the compound from Example 39 in 2.0 ml of $Et_2O$, was added 0.273 ml of a solution containing 1.0 ml of concentrated HCl in 11.0 ml of $CH_3CN$. The reaction mixture was diluted with 10.0 ml of $CH_3CN$ and then concentrated in vacuo to provide an oily residue. This residue was triturated with 3.0 ml of $Et_2O$ and then isolated by filtration.

Yield: 105 mg (97%).

$^1$H NMR (300MHz, $d_6$-DMSO):δ8.35 (bs, 1H); 8.10 (d, J=8Hz, 1H); 6.80 (d, J=4Hz, 1H); 6.71 (dd, J=4, 8Hz, 1H); 3.78 (s, 3H); 3.68 (s, 3H); 3.57 (m, 1H); 2.74 (m, 1H); 2.58 (s, 6H); 2.26 (m, 2H); 1.70 (m, 2H); 1.45 (m, 1H); 1.30 (s, 3H); 1.10 (m, 1H) and 1.02 (s, 3H).

MS: m/e 358 (M+-HCl).

Elemental Analysis for $C_{21}H_{31}N_2O_3Cl$:

Calc: C, 63.87; H, 7.91; N, 7.09; Cl, 8.98;

Found: C, 64.17; H, 8.07; N, 7.07; Cl, 9.08.

EXAMPLE 41

To a solution of 2.0 g (6.32 mmol) of the compound from Example 6 in 20.0 ml of EtOH, was added 12.0 ml (100 mmol) of 1-amino-4-methylpiperazine, 2.8 g (50 mmol) of KOH. The mixture was heated to 80° C. for 2 hours, concentrated in vacuc, diluted with 250 ml of $Et_2O$, and washed with 100 ml of $H_2O$. The resultant layers were separated and the organic layer was dried over $Na_2SO_4$, filtered and concentrated in vacuo to provide a thick oil. This oil was purified using radial chromatography (4000 micron plate, gradient eluent of 0–15% MeOH in EtOAc).

Yield: 2.29 g (88%).

$^1$H NMR (300MHz, $CDCl_3$):δ8.13 (d, J=8Hz, 1H); 6.80 (d, J=4Hz, 1H); 6.72 (dd, J=4,8Hz, 1H); 3.80 (s, 3H); 3.70 (s, 3H); 3.66 (m, 1H); 2.95 (m, 2H); 2.80 (m, 2H); 2.70 (m, 1H); 2.60 (m, 4H); 2.35 (s, 3H); 2.26 (m, 2H); 1.95 (m, 1H); 1.70 (m, 2H); 1.45 (m, 1H); 1.30 (s, 3H); 1.10 (m, 1H) and 1.03 (s, 3H).

EXAMPLE 42

The compound was prepared substantially in accordance with the procedure detailed in Example 40, using 2.29 g (5.54 mmol) of the compound of Example 41, and 5.54 ml of a solution consisting of 1.0 ml concentrated HCl and 11.0 ml of $CH_3CN$.

Yield: 2.31 g (93%).

$^1$H NMR (300MHz, $d_6$-DMSO):δ10.5 (bs, 1H); 8.02 (d, J=8Hz, 1H); 6.88 (d, J=4Hz, 1H); 6.80 (dd, J=4,8Hz, 1H); 3.78 (s, 3H); 3.64 (s, 3H); 3.50 (m, 1H); 3.33 (m, 4H); 3.03 (m, 4H) 2.63 (m, 1H); 2.77 (s, 3H); 2.30 (m, 1H); 2.10 (m, 1H); 1.84 (m, 1H); 1.68 (m, 1H); 1.58 (m, 1H); 1.31 (m, 1H); 1.20 (s, 3H); 1.10 (m, 1H) and 0.93 (s, 3H).

MS: m/e 413 (M+-HCl).

Elemental Analysis for $C_{24}H_{36}N_3O_3Cl$:

Calcd: C, 64.05; H, 8.06; N, 9.34; Cl, 7.21;

Found: C, 63.85; H, 7.98; N, 9.50; Cl, 7.67.

EXAMPLE 43

To a solution of 330 mg (1.04 mmol) of the compound from Example 6 in 4.0 ml of EtOH was added 100 mg (1.2 mmol) of methoxyamine hydrochloride and 98 mg (1.2 mmol) of NaOAc. The reaction mixture was stirred at room temperature for 67 hours, heated to 80° C. and reacted for approximately 3 hours and then concentrated in vacuo. The crude material was purified using radial chromatography (2000 micron plate, eluent of 3% EtOAc in $CH_2Cl_2$) to provide an oil which was dissolved in MeOH and recrystallized at 0° C.

Yield: 43 mg (12%).

$^1$H NMR (300MHz, $CDCl_3$): δ7.95 (d, J=8Hz, 1H); 6.83 (d, J=4Hz, 1H); 6.75 (dd, J=4,8Hz, 1H); 4.0 (s, 3H); 3.82 (s, 3H); 3.72 (s, 3H); 3.32 (m, 1H); 2.97 (m, 1H); 2.28 (m, 2H); 1.98 (m, 1H); 1.68 (m, 2H); 1.52 (m, 1H); 1.25 (s, 3H); 1.10 (m, 1H) and 0.98 (s, 3H).

MS: m/e 345 (M+).

EXAMPLE 44

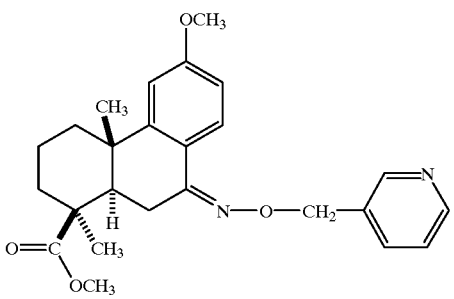

To a solution of 175 mg (0.528 mmol) of the compound from Example 7 in 3.0 ml of dioxane, was added 235 mg (1.70 mmol) of $K_2CO_3$ and 112 mg (0.687 mmol) of 3-picolyl chloride hydrochloride. The reaction mixture was heated to 100° C., reacted for 15 minutes and then concentrated in vacuo to provide a tan residue. This residue was dissolved in 75.0 ml of EtOAc, washed with a saturated $NaHCO_3$ solution, dried over $Na_2SO_4$, filtered and then concentrated in vacuo to provide 180 mg of crude material which was purified using radial chromatography (2000 micron plate, gradient eluent of 5–20% EtOAc in $CH_2Cl_2$).

Yield: 90 mg (40%).

$^1$H NMR (300MHz, $CDCl_3$):δ8.70 (m, 1H); 8.55 (m, 1H); 7.9 (d, J=8Hz, 1H); 7.77 (m, 1H); 7.30 (m, 1H); 6.80 (d, J=4Hz, 1H); 6.72 (dd, J=4,8Hz, 1H); 5.22 (s, 2H); 3.80 (s, 3H); 3.70 (s, 3H); 3.37 (m, 1H); 3.02 (m, 1H); 2.25 (m, 2H); 1.95 (m, 1H); 1.67 (m, 2H); 1.50 (m, 1H); 1.27 (s, 3H); 1.10 (m, 1H) and 0.97 (s, 3H).

EXAMPLE 45

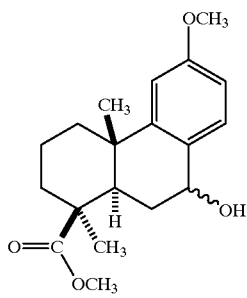

To a solution of 500 mg (1.58 mmol) of the compound from Example 6 in 5.0 ml of MeOH was added 101 mg (1.6 mmol) of sodium cyanoborohydride and a trace (a trace) of methyl orange. A 2N HCl methanolic solution was added dropwise to maintain the red color of the reaction. After approximately 15 minutes, the color stabilized (red) and the reaction was stirred for 45 minutes longer. The reaction mixture was concentrated in vacuo to provide an orange residue. The residue was dissolved in $Et_2O$ and washed with brine, dried over $Na_2SO_4$, filtered and concentrated in vacuo to provide an oil which solidified on standing. The solid was purified using radial chromatography (4000 micron plate, eluent of 5% EtOAc in $CH_2Cl_2$).

Yield: 226 mg (45%).

$^1$H NMR (300MHz, $CDCl_3$):δ7.50 (d, J=8Hz, 1H); 6.77 (m, 2H); 4.68 (m, 1H); 3.80 (s, 3H); 3.62 (s, 3H); 2.55 (m, 1H); 2.22 (m, 2H); 1.90 (m, 3H); 1.58 (m, 2H); 1.35 (m, 1H); 1.27 (s, 3H); 1.03 (m, 1H) and 1.0 (s, 3H).

MS: m/e 318 (M+).

EXAMPLE 46

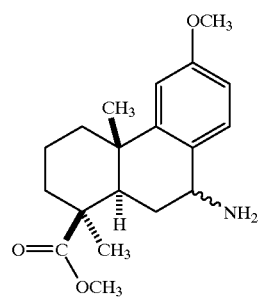

To a solution of 1.0 g (3.16 mmol) of the compound from Example 6 in 15.0 ml of MeOH, was added 1.0 g crushed and activated 4.0 Å molecular sieves, 2.46 g (32 mmol) of ammonium acetate and 201 mg (3.2 mmol) of sodium cyanoborohydride. The reaction was stirred at room temperature for 1 hour and then quenched with 30.0 ml of $H_2O$. The desired compounds were extracted with 100 ml of $Et_2O$, washed with a saturated $NaHCO_3$ solution, dried over $Na_2SO_4$, filtered and then concentrated in vacuo to provide a yellow residue. This residue was purified using flash chromatography ($SiO_2$, gradient eluent of 0–5% EtOAc in $CH_2Cl_2$).

Yield: 290 mg (29%).

$^1$NMR (300MHz, $CDCl_3$):δ7.45 (d, J=8Hz, 1H); 6.78 (m, 2H); 3.85 (m, 1H); 3.78 (s, 3H); 3.67 (s, 3H); 2.40 (m, 1H); 2.22 (m, 2H); 1.95 (m, 2H); 1.78 (m, 1H); 1.58 (m, 3H); 1.40 (m, 1H); 1.27 (s, 3H); 1.10 (m, 1H) and 1.05 (s, 3H).

EXAMPLE 47

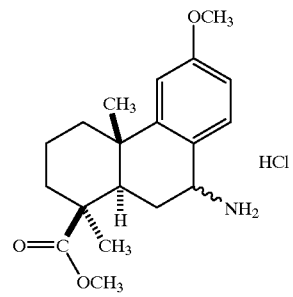

To a solution of 20 mg (0.063 mmol) of the compound from Example 46 in 3.0 ml of a 2:1 $Et_2O$/hexane mixture, was added 63 μl of a solution consisting of 1.0 ml of concentrated HCl in 11.0 ml of $CH_3CN$. The resultant precipitate was filtered, washed with 3.0 ml of a 1:1 $Et_2O$/hexane mixture and dried in vacuo.

Yield: 21 mg (95%).

$^1$H NMR (300MHz, $d_6$-DMSO):δ8.42 (m, 3H); 7.50 (d, J=8Hz, 1H); 6.82 (m, 2H); 4.35 (m, 1H); 3.70 (s, 3H); 3.58 (s, 3H); 2.50 (m, 1H); 2.20 (m, 2H); 1.87 (m, 2H); 1.58 (m, 2H); 1.25 (m, 1H); 1.20 (s, 3H); 1.10 (m, 1H) and 1.0 (s, 3H).

MS: m/e 317 (M+).

EXAMPLE 48

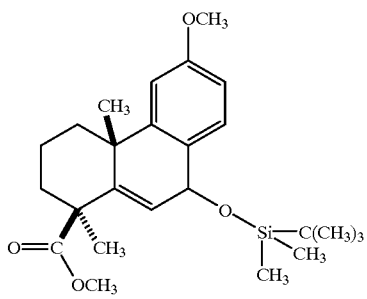

To a solution of 1.0 g (3.16 mmol) of the compound from Example 6 in 15.0 ml of $CH_2Cl_2$, was added 0.44 ml (3.8 mmol) of 2,6-lutidine and 0.80 ml (3.5 mmol) of t-butyldimethylsilyl trifluoromethanesulfonate. The reaction mixture was stirred at room temperature for 1 hour, diluted with $Et_2O$ and washed sequentially with $H_2O$ and a saturated $NaHCO_3$ solution, dried over $Na_2SO_4$, filtered and concentrated in vacuo.

Yield: 1.36 g (quantitative).

$^1$H NMR (300MHz, $CDCl_3$): δ7.42 (d, J=8Hz, 1H); 6.78 (d, J=4Hz, 1H); 6.72 (dd, J=4,8Hz, 1H); 5.55 (d, J=4Hz, 1H); 3.80 (s, 3H); 3.68 (s, 3H); 2.42 (d, J=4Hz, 1H); 2.30 (m, 1H); 2.15 (m, 1H); 1.95 (m, 1H); 1.65 (m, 2H); 1.27 (s, 3H); 1.10 (m, 1H); 1.03 (s, 9H); 0.90 (s, 3H); 0.28 (s, 3H) and 0.18 (s, 3H).

EXAMPLE 49

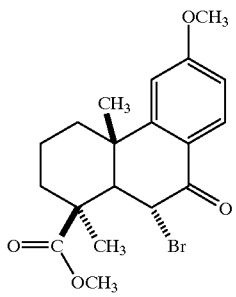

To a solution of 1.36 g (3.16 mmol) of the compound from Example 48 in 10.0 ml of THF, was added 1.6 ml of a 1M bromine in AcOH solution. The reaction mixture was diluted with $Et_2O$, washed with a saturated $NaHCO_3$ solution, dried over $Na_2SO_4$, filtered and then concentrated in vacuo to provide a yellow solid. This solid was dissolved in 10.0 ml of MeOH, cooled to 0° C. and reacted for 18 hours. The resultant white crystals were filtered and dried in vacuo.

Yield: 935 mg (75%).

$^1$H NMR (300MHz, $CDCl_3$):δ7.82 (d, J=8Hz, 1H); 6.88 (dd, J=4,8Hz, 1H); 6.83 (d, J=8Hz, 1H); 5.82 (d, J=6Hz, 1H); 3.86 (s, 3H); 3.73 (s, 3H); 2.52 (d, J=6Hz, 1H); 2.37 (m, 1H); 2.17 (m, 1H); 1.92 (m, 1H); 1.78 (m, 2H); 1.57 (s, 3H); 1.22 (m, 1H) and 0.87 (s, 3H).

EXAMPLE 50

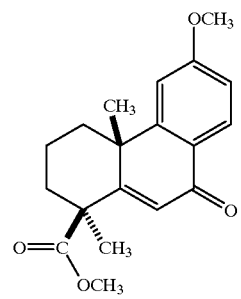

To a solution of 910 mg (2.30 mmol) of the compound from Example 49 in 10.0 ml of MeOH, was added 11.2 ml (5.6 mmol) of a 0.5M sodium methoxide (NaOMe) in MeOH solution. The reaction mixture was heated to 65° C. for 5 hours and then concentrated in vacuo to provide a residue which was dissolved in a 2:1 $Et_2O/H_2O$ mixture. The resulting layers were separated and the organic layer was dried over $Na_2SO_4$, filtered and concentrated in vacuo.

Yield: 705 mg (98%). $^1$H NMR (300 MHz, $CDCl_3$): δ 8.15 (d, J=8 Hz, 1H); 6.93 (m, 2H); 6.57 (s, 1H); 3.87 (s, 3H); 3.63 (s, 3H); 2.52 (m, 1H); 2.30 (m, 1H); 2.13 (m, 1H); 1.70 (m, 1H); 1.50 (m, 1H); 1.47 (s, 3H); 1.31 (s, 3H) and 1.24 (m, 1H). MS: m/e 314 (M+).

Elemental Analysis for $C_{19}H_{22}O_4$: Calc: C, 72.59; H, 7.05; Found: C, 72.72; H, 7.13.

EXAMPLE 51

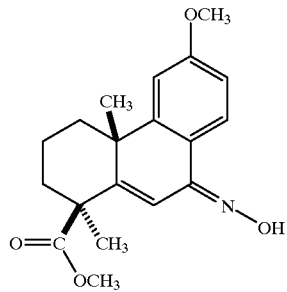

To a solution of 100 mg (0.318 mmol) of the compound from Example 50 in 5.0 ml of EtOH, was added 1.47 g (21.2 mmol) of hydroxylamine hydrochloride and 1.74 g (21.2 mmol) of NaOAc. The reaction mixture was heated to 78° C. and reacted for 18 hours and then concentrated in vacuo to provide a residue which was dissolved in a 2:1 EtOAc/$H_2O$ mixture. The resultant layers were separated and the organic layer was dried over $Na_2SO_4$, filtered and concentrated in vacuo to provide a yellow solid which was purified using radial chromatography (1000 micron plate (eluent of 1% MeOH in $CH_2Cl_2$).

Yield: 87 mg (83%). $^1$H NMR (300 MHz, $CDCl_3$): δ 8.30 (bs, 1H); 7.95 (d, J=8 Hz, 1H); 7.30 (s, 1H); 6.85 (m, 2H); 3.82 (s, 3H); 3.62 (s, 3H): 2.45 (m, 1H); 2.25 (m, 1H); 2.10 (m, 1H); 1.65 (m, 1H); 1.57 (m, 1H); 1.53 (s, 3H); 1.27 (s, 3H) and 1.22 (m, 1H) MS: m/e 329 (M+).

Elemental Analysis for $C_{19}H_{23}NO_4$: Calc: C, 69.28; H, 7.04; N, 4.25; Found: C, 69.29; H, 7.23; N, 4.23.

EXAMPLE 52

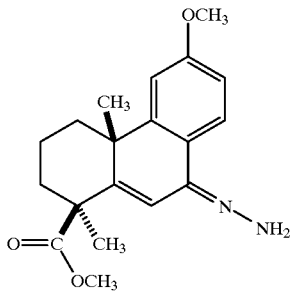

To a solution of 150 mg (0.48 mmol) of the compound from Example 50 in 2.0 ml of EtOH, was added 28 µl (0.48 mmol) of AcOH and 555 µl (11.4 mmol) of hydrazine. The reaction mixture was heated to 80° C. for 7 hours, concentrated in vacuo to provide a residue. This residue was diluted with 100 ml of Et$_2$O, washed with a saturated NaHCO$_3$ solution, dried over Na$_2$SO$_4$, filtered and concentrated in vacuo to provide an oily residue. This residue was dissolved in 5.0 ml of hot hexane and cooled to 0° C. for 16 hours.

Yield: 135 mg (85%). $^1$H NMR (300 MHz, CDCl$_3$): δ 8.0 (d. J=8 Hz, 1H); 6.80 (m, 3H); 5.40 (s, 2H); 3.80 (s, 3H); 3.60 (s, 3H); 2.45 (m, 1H); 2.27 (m, 1H); 2.08 (m, 1H); 1.70 (m, 1H); 1.55 (m, 1H); 1.27 (s, 3H) and 1.22 (m, 1H). MS: m/e 328 (M+).

EXAMPLE 53

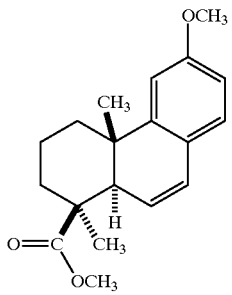

To a cold (0° C.) solution of 595 mg (1.87 mmol) of the compound from Example 45 in 3.5 ml of CH$_3$CN, was added a mixture containing 2.0 ml CF$_3$COOH/0.1 ml CH$_3$CN/0.2 ml H$_2$O. The reaction mixture was warmed to room temperature, stirred for 30 minutes and then diluted with 50.0 ml of EtOAc. The resultant layers were separated and the organic layer was washed sequentially with H$_2$O and a saturated NaHCO$_3$ solution, dried over Na$_2$SO$_4$, filtered and concentrated in vacuo.

Yield: 494 mg (88%). $^1$H NMR (300 MHz, CDCl$_3$): δ 7.0 (d, J=8 Hz, 1H); 6.80 (d, J=4 Hz, 1H); 6.67 (dd, J=4,8 Hz, 1H); 6.40 (m, 2H); 3.80 (s, 3H); 3.70 (s, 3H); 2.35 (m, 2H); 2.20 (m, 1H); 1.95 (m, 1H); 1.65 (m, 2H); 1.30 (s, 3H); 1.13 (m, 1H) and 0.87 (s, 3H)

EXAMPLE 54

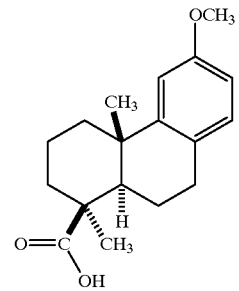

To a solution of 1.0 g (3.31 mmol) of the compound from Example 1A in 10.0 ml of THF, was added 1.0 g (6.4 mmol) of benzeneselenol, 302 mg (6.29 mmol) of a 50% dispersion of NaH in mineral oil and 84 mg (0.32 mmol) of 18-crown-6 ether. The reaction mixture was refluxed for 15 hours, cooled to room temperature and diluted with 100 ml of Et$_2$O and 20 ml of 1N HCl. The resultant layers were separated and the organic layer was dried over Na$_2$SO$_4$, filtered and concentrated in vacuo. The crude material was purified using flash chromatography (SiO$_2$, eluent of 25% EtOAc in hexane) to provide a solid which was recrystallized from Et$_2$O/hexane.

Yield: 731 mg (77%) $^1$H NMR (300 MHz, CD$_3$O): δ 6.9 (d, J=8 Hz, 1H); 6.75 (d, J=4 Hz, 1H); 6.60 (dd, J=4.8 Hz, 1H); 3.70 (s, 3H); 2.70 (m, 2H); 2.20 (m, 3H); 2.20 (m, 2H); 1.53 (m, 2H); 1.33 (m, 1H); 1.27 (s, 3H); 1.10 (s, 3H) and 1.07 (m, 1H). MS: m/e 288 (M+).

EXAMPLE 55

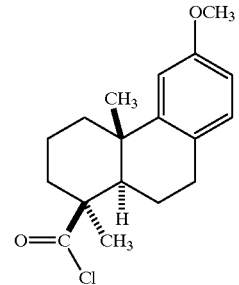

To a solution of 360 mg (1.25 mmol) of the compound from Example 54 in 25.0 ml of toluene, was added 0.545 ml (6.25 mmol) of oxalyl chloride in 25 µl of DMF. The reaction mixture was stirred at room temperature with gas evolution for 30 minutes, heated briefly (2 minutes) to reflux and then concentrated in vacuo.

Yield: 381 mg crystals (99%). $^1$H NMR (300 MHz, CDCl$_3$): δ 6.98 (d, J=8 Hz, 1H); 6.82 (d, J=4 Hz, 1H); 6.68 (dd, J=4,8 Hz, 1H); 3.80 (s, 3H); 2.80 (m, 2H); 2.25 (m, 3H); 2.05 (m, 2H); 1.65 (m, 2H); 1.42 (m, 1H); 1.40 (s, 3H); 1.25 (s, 3H) and 1.20 (m, 1H).

EXAMPLE 56

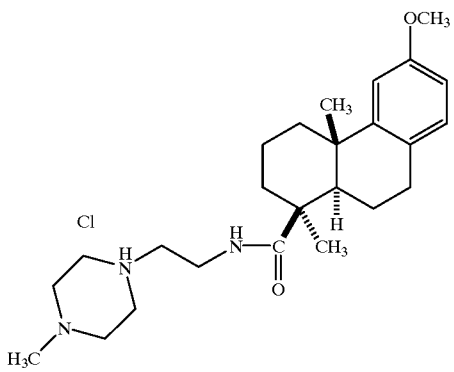

To a solution of 100 mg (0.33 mmol) of the compound from Example 55 in 2.0 ml of $CH_2Cl_2$, were added 43 μl (0.358 mmol) of 2-(2-aminoethyl)pyridine, 50 μl (0.36 mmol) of $Et_3N$ and 5 mg (0.036 mmol) of 4-dimethylaminopyridine in 4.0 ml of $CH_2Cl_2$. The reaction mixture was diluted with $CH_2Cl_2$, washed with $H_2O$, dried over $Na_2SO_4$, filtered and concentrated in vacuo to provide a tan solid. This solid was dissolved in 3.0 ml of $CH_3CN$ and treated with 0.36 ml of a solution of 1.0 ml of concentrated HCl in 11.0 ml of $CH_3CN$.

Yield: 120 mg (78%). $^1H$ NMR (300 MHz, $d_6$-DMSO): δ 8.75 (d, J=6 Hz, 1H); 8.40 (t, J=6 Hz, 1H); 7.80 (m, 2H); 7.40 (m, 1H); 6.85 (d, J=8 Hz, 1H); 6.70 (d, J=4 Hz, 1H); 6.60 (dd, J=4, 8 Hz, 1H); 3.60 (s, 3H); 3.55 (m, 2H); 3.19 (m, 2H); 2.68 (m, 1H); 2.55 (m, 1H); 2.10 (m, 3H); 1.78 (m, 2H); 1.43 (m, 1H); 1.30 (m, 1H); 1.17 (m, 1H); 1.02 (s, 3H); 0.99 (m, 1H) and 0.80 (s, 3H). MS: m/e 392 (M+—HCl).

EXAMPLE 57

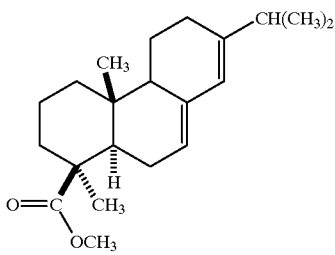

To a solution of NaOme (prepared in situ from 2.6 g of sodium and 400 ml of anhydrous MeOH (0.108 mol), under $N_2$), was added 15.0 g (0.035 mol) of 70% abietic acid. After stirring the mixture for 10 minutes, 14.0 ml (0.22 mol) of iodomethane was added and the mixture was refluxed for 24 hours, cooled and concentrated in vacuo to provide a residue. This residue was dissolved in 500 ml of EtOAc, washed sequentially with 500 ml of a saturated $NaHCO_3$ solution and a saturated sodium chloride solution (NaCl), dried over $Na_2SO_4$, filtered and concentrated in vacuo. The crude material was purified using flash chromatography (eluent of 2% EtOAc in hexanes).

Yield: 10.0 g of a dark yellow oil (90.4%). IR($CHCl_3$): 2952, 1718 and 1251 cm$^{-1}$. $^1H$ NMR (300 MHz, $CDCl_3$): δ 5.78 (s, 1H); 5.38 (brs, 1H); 3.66 (s, 3H); 2.17–2.30 (m, 3H); 1.68–2.16 (m, 8H); 1.50–1.65 (m, 2H); 1.26 (s, 3H); 1.24 (m, 2H); 1.02 (d, J=2.6 Hz, 3H); 1.00 (d, J=2.6 Hz, 3H) and 0.83 (s, 3H). MS(FD): m/e 316(M+).

Elemental Analysis for $C_{21}H_{32}O_2$: Calcd: C, 79.70; H, 10.19; Found: C, 79.49; H, 9.94.

EXAMPLE 58

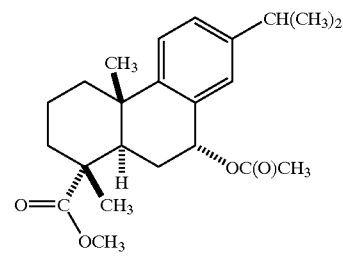

To a mixture of 5.0 g (15.8 mmol) of the compound in Example 57 in 100 ml of acetic anhydride, was added 2.5 g (22.5 mmol) of selenium (IV) oxide, under $N_2$. The reaction mixture was warmed to 70° C., stirred for 16 hours, cooled, filtered and then diluted to 500 ml with $CH_2Cl_2$. The resulting layers were separated and the organic layer was washed with 500 ml of NaCl, dried over $Na_2SO_4$, filtered and then concentrated in vacuo to provide a dark yellow solid. This solid was purified using flash chromatography (eluent of 5% EtOAc in hexanes) to provide two major fractions.

The first fraction was concentrated to provide 537 mg of an oil. This oil was hydrogenated with 135 mg of 5% Pd/C in 25 ml of MeOH (8 hours, room temperature, 6.0 psi). The reaction mixture was filtered and the filtrate concentrated in vacuo. The crude material was purified using flash chromatography (eluent of 2% EtOAc in hexanes) to provide the compound of Example 59 (400 mg of a clear oil (75%) m.p. 50° C.). The second fraction was concentrated in vacuc to provide the compound.

Yield: 2.8 g of a light yellow solid (47%). m.p. 165–167° C. IR (KBr): 2956, 1722 and 1251 cm$^{-1}$. $^1H$ NMR (300 MHz, $CDCl_3$): δ 7.23 (m, 2H); 7.04 (d, J=1.8 Hz, 1H); 5.90 (m, 1H); 3.64 (s, 3H); 2.86 (m, 1H); 2.60 (dd, J=1.5,11.0 Hz, 1H); 2.31 (d, J=12.1 Hz, 1H); 2.08 (s, 3H); 2.07 (m, 1H); 1.60–1.80 (m, 6H); 1.26 (s, 3H); 1.24 (s, 3H); 1.22 (s, 3H) and 1.19 (s, 3H). MS(FD): m/e 372(M+).

Elemental Analysis for $C_{23}H_{32}O_4$: Calcd: C, 74.16; H, 8.66; Found: C, 74.44; H, 8.71.

EXAMPLE 59

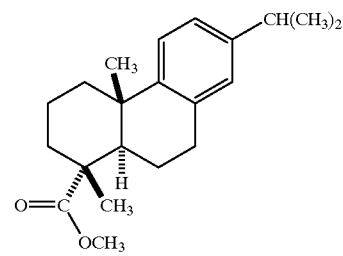

To a mixture of 23.6 g (0.063 mmol) of the compound in Example 58 in 1500 ml of MeOH, was added 5.8 g of 10% Pd/C and 5.8 g (0.030 mmol) of p-toluenesulfonic acid monohydrate. The reaction mixture was reacted for 16 hours at room temperature, 60 psi, filtered and then concentrated in vacuo to provide a residue. This residue was dissolved in 700 ml of EtOAc, washed sequentially with 700 ml of saturated NaHCO$_3$ and NaCl solutions, dried over Na$_2$SO$_4$, filtered and then concentrated in vacuo.

Yield: 19.3 g (97.5%) of an oil. IR (CHCl$_3$), 2955, 1718 and 1254 cm$^{-1}$. $^1$H NMR (300 MHz, CDCl$_3$): δ 7.16 (d, J=8 Hz, 1H); 7.00 (d, J=8 Hz, 1H); 6.88 (s, 1H); 3.66 (s, 3H); 2.80–2.90 (m, 3H); 2.23–2.32 (m, 2H); 1.35–1.90 (m, 7H); 1.28 (s, 3H); 1.24 (s, 3H) and 1.21 (s, 6H). MS(FD): m/e 314(M+).

Elemental Analysis for C$_{21}$H$_{30}$O$_2$: Calcd: C, 80.21; H, 9.62 Found: C, 80.34; H, 9.73

EXAMPLE 60

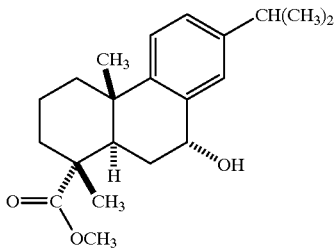

To a suspension of 185 mg (0.50 mmol) of the compound of Example 58 in 10 ml of MeOH, was added 5 ml (0.50 mmol) of 0.1N NaOH. The reaction mixture was refluxed for 2 hours, cooled and partitioned between 50 ml of EtOAc and 50 ml of 0.2N HCl. The resulting layers were separated and the organic layer was washed with 50 ml of a saturated NaCl solution, dried over Na$_2$SO$_4$, filtered and then concentrated in vacuo to provide a yellow oil which was purified using flash chromatography (eluent of 10% EtOAc in hexanes).

Yield: 158 mg of a clear oil (96%). m.p. 105–107° C. IR (KBr): 2957, 3500 and 1719 cm$^{-1}$. $^1$H NMR (300 MHz, CDCl$_3$): δ 7.20 (m, 3H); 4.75 (t, J=4.8 Hz, 1H); 3.69 (s, 3H); 2.88 (m, 1H); 2.50 (dd, J=1.8,13.2 Hz, 1H); 2.30 (brd, J=12.1 Hz, 1H); 2.06–2.17 (m, 1H); 1.98 (d, J=7.0 Hz, 1H); 1.69–1.84 (m, 4H); 1.55 (m, 2H); 1.29 (s, 3H); 1.25 (s, 3H); 1.23 (s, 3H) and 1.17 (s, 3H). MS(FD): m/e 330(M+).

EXAMPLE 61

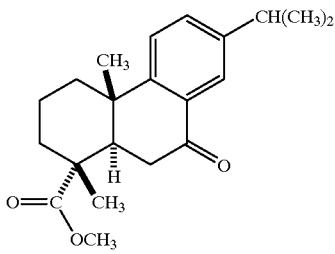

To a solution of 112 mg (0.30 mmol) of the titled compound of Example 60 in 4 ml of glacial AcOH and 1 ml of H$_2$O, was added 10 mg (1.0 mmol) of chromium trioxide. The resultant mixture was stirred at room temperature for 1 hour and then partitioned between 50 ml of EtOAc and 50 ml of a saturated NaCl solution. The resultant layers were separated and the organic layer was dried over Na$_2$SO$_4$, filtered and then concentrated in vacuo to provide a dark oil. This oil was purified using flash chromatography (eluent of 5% EtOAc in hexanes) to provide an oil which solidified on standing.

Yield: 100 mg (90%). IR (CHCl$_3$): 2965, 1722, 1675 and 1253 cm$^{-1}$. $^1$H NMR 300 MHz, CDCl$_3$): δ 7.88 (d, J=1.8 Hz, 1H); 7.42 (dd, J=1.8,8.1 Hz, 1H); 7.30 (d, J=8.1 Hz, 1H); 3.66 (s, 3H); 2.86–298 (m, 1H); 2.66–2.76 (m, 2H); 2.28–2.40 (m, 2H); 1.60–1.90 (m, 5H); 1.35 (s, 3H); 1.26 (s, 6H) and 1.24 (s, 3H). MS(FD): m/e 329(M+).

Elemental Analysis for C$_{21}$H$_{28}$O$_3$: Calcd: C, 76.79; H, 8.59; Found: C, 76.52; H, 8.53.

EXAMPLE 62

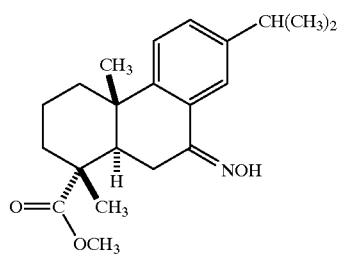

A mixture containing 118 mg (0.36 mmol) of the compound of Example 61, 40 mg (0.58 mmol) of hydroxylamine hydrochloride, 40 mg (0.48 mmol) of NaHCO$_3$, 1 drop of glacial AcOH, 1.0 ml of H$_2$O and 15 ml of MeOH was with a Dean-Stark trap for approximately 5 hours. The reaction mixture was concentrated in vacuo to provide a residue. This residue was partitioned between H$_2$O and CH$_2$Cl$_2$ and the organic layer was dried over Na$_2$SO$_4$, filtered and concentrated in vacuo. The crude material was purified using flash chromatography.

Yield: 120 mg (97%). IR(CHCl$_3$): 3582, 2962, 1721 and 1261 cm$^{-1}$. $^1$H NMR (300 MHz, CDCl$_3$ ): δ 7.71 (s, 1H); 7.43 (s, 1H); 7.21 (s, 2H); 3.66 (s, 3H); 2.85–2.95 (m,1H); 2.67 (m, 2H); 2.26–237 (m, 2H); 1.75 (m, 5H); 1.38 (s, 3H); 1.26 (s, 3H); 1.24 (s, 3H); 1.13 (s, 3H); MS(FD) m/e 343(M+).

EXAMPLE 63

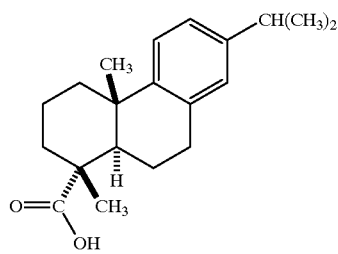

A mixture of 500 mg (1.59 mmol) of the compound of Example 59, 1.0 g (17.8 mmol) of KOH and 20 ml of n-butyl alcohol was refluxed for 16 hours, under N$_2$. After cooling, the mixture was acidified with 5N HCl and concentrated in vacuo to provide a residue. This residue was suspended in 50 ml of H$_2$O and filtered. The resulting solid was dissolved in 50 ml of MeOH, filtered and the filtrate was concentrated in vacuo.

Yield: 330 mg of a foam (69%). m.p. 143–145° C. IR (KBr): 2958, 1695 and 1279 cm$^{-1}$. $^1$H NMR (300 MHz, CDCl$_3$): δ 7.25 (d, J=3 Hz, 1H); 7.17 (d, J=8 Hz, 1H); 7.00 (dd, J=3.9 Hz, 1H); 6.89 (brs, 1H); 2.80–3.00 (m, 3H); 2.20–2.40 (m, 2H); 1.65–1.96 (m, 5H); 1.43–1.60 (m, 2H); 1.29 (s, 3H); 1.24 (s, 3H); 1.22 (S, 3H); 1.21 (S, 3H); MS(FD) m/e 301(m+).

Elemental Analysis for $C_{20}H_{28}O_2 \cdot 0.5H_2O$: Calcd: C, 79.01; H, 9.47; Found: C, 79.19; H, 9.52.

EXAMPLE 64

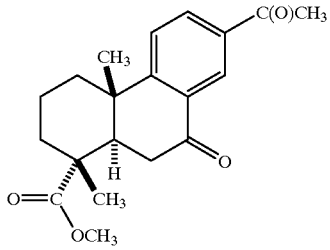

To a cold (0° C.) solution of 8.0 g (25.0 mmol) of the compound of Example 59 in 50 ml of acetic anhydride and 38 ml of AcOH, was added 11.0 g (0.11 mmol) of chromium trioxide slowly, under $N_2$. The reaction mixture was partitioned between EtOAc and brine and the organic layer was dried over $Na_2SO_4$, filtered and concentrated to provide a yellow oil which was purified using flash chromatography ($SiO_2$, eluent of 10% EtOAc in hexanes) to provide a solid which was filtered with the aid of hexanes.

Yield: 2.5 g (30.5%). m.p. 144–145° C. IR (KBr): 2951, 1725 and 1680 cm$^{-1}$. $^1$H NMR (300 MHz, CDCl$_3$): δ 8.55 (d, J=2 Hz, 1H); 8.17 (dd, J=2.8 Hz, 1H); 7.50 (d, J=8 Hz, 1H); 3.66 (s, 3H); 2.75 (m, 2H); 2.64 (s, 3H); 2.37–2.50 (m, 2H); 1.60–1.90 (m, 5H); 1.37 (s, 3H) and 1.29 (s, 3H). MS(FD): m/e 328 (M+).

Elemental Analysis for $C_{20}H_{24}O_4$: Calcd: C, 73.15; H, 7.37; Found: C, 72.86; H, 7.42.

EXAMPLE 65

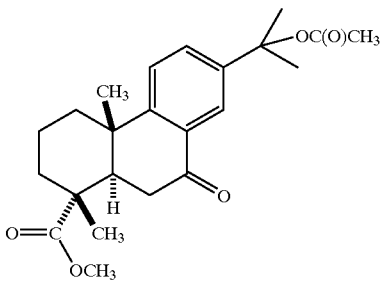

The compound was isolated from the reaction mixture described in Example 64.

Yield: 4.2 g of a white solid (43.5%). m.p. 130–133° C. IR (KBr): 2934. 1734, 1720 and 1680 cm$^{-1}$. $^1$H NMR (300 MHz, CDCl$_3$): δ 7.98 (d, J=2 Hz, 1H); 7.54 (dd, J=2.8 Hz, 1H); 7.33 (d, J=8 Hz, 1H); 3.66 (s, 3H); 2.75 (m, 2H); 2.30–2.42 (m, 2H); 2.2 (m, 1H); 2.04 (s, 3H); 2.00–2.10 (m, 1H); 1.70–1.90 (m, 3H); 1.76 (s, 6H); 1.35 (s, 3H) and 1.26 (s, 3H). MS(FD): m/e 386 (M+).

Elemental Analysis for $C_{23}H_{30}O_5$: Calcd: C, 71.48; H, 7.82; Found: C, 71.75; H, 8.03.

EXAMPLE 66

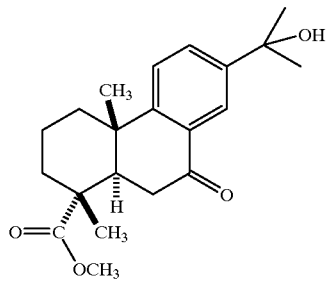

To a solution of 4.14 g (10.7 mmol) of the compound of Example 65 in 40 ml of MeOH, was added 13.4 ml (13.4 mmol) of 1N NaOH. The reaction mixture was refluxed for 2.5 hours, cooled and then partitioned between 200 ml of 0.2N HCl and 200 ml of EtOAc. The resultant layers were separated and the organic layer was washed with 200 ml of brine, dried over $Na_2SO_4$, filtered and then concentrated in vacuo to provide a dark yellow oil. This oil was purified using flash chromatography ($SiO_2$, eluent of 15% EtOAc in hexanes).

Yield: 2.9 g of a white foam (80%). m.p. 57–60° C. IR(KBr): 3444, 2936, 1727 and 1682 cm$^{-1}$. $^1$H NMR (300 MHz, CDCl$_3$): δ 8.06 (d, J=2.2 Hz, 1H); 7.74 (dd, J=2.2,8.5 Hz, 1H); 7.36 (d, J=8.5 Hz, 1H); 3.66 (s, 3H); 2.70 (m, 2H); 2.40 (m, 2H); 1.60–1.90 (m, 6H); 1.60 (s, 3H); 1.55 (s, 3H); 1.35 (s,3H) and 1.27 (s, 3H). MS(FD): m/e 344(M+).

Elemental Analysis for $C_{21}H_{28}O_4$: Calcd: C, 73.23; H, 8.19; Found: C, 73.50; H, 8.46.

EXAMPLE 67

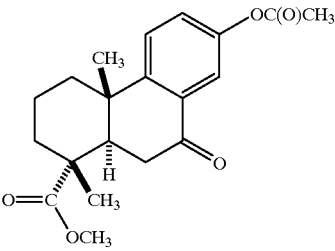

A mixture of 500 mg (1.52 mmol) of the compound of Example 64, 620 mg (1.80 mmol) of 50% m-chloroperbenzoic acid, 5.0 mg (0.03 mmol) of p-toluene sulfonic acid monohydrate and 5 ml of 1,2-dichloroethane was refluxed for 4 hours and then stirred overnight at room temperature. The mixture was diluted with 25 ml of EtOAc and washed sequentially with 25 ml of 10% potassium iodide, 10% sodium thiosulfate, saturated NaHCO$_3$ and brine, dried over Na$_2$SO$_4$, filtered and then concentrated in vacuo. The crude material was purified by radial chromatography (eluent of 25% Et$_2$O in hexanes).

Yield: 30 mg (6%). IR(CHCl$_3$): 3020, 1723 and 1684 cm$^{-1}$. $^1$H NMR (300 MHz, CDCl$_3$): δ 7.69 (d, J=3 Hz, 1H), 7.39 (d, J=9 Hz, 1H); 7.24 (d, J=3 Hz, 1H); 3.67 (s, 3H); 2.84 (m, 2H); 2.25–2.42 (m, 2H); 2.31 (s, 3H); 1.60–1.90 (m, 5H); 1.35 (s, 3H) and 1.28 (s, 3H). MS(FD): m/e 344(M+).

Elemental Analysis for $C_{20}H_{24}O_5$: Calcd: C, 69.75; H, 7.02; Found: C, 69.77; H, 6.92.

EXAMPLE 68

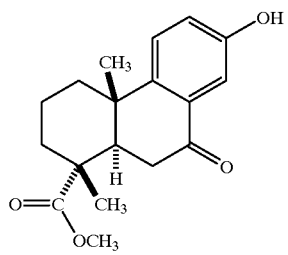

The compound was prepared substantially in accordance with the procedure detailed in Matsumoto et al., Bull. Chem. Soc. Jpn., vol. 61, pages 723–727 (1988), using the compound of Example 64.

Yield: 42%. IR(CHCl$_3$): 3389, 2948, 1725, 1670, 1606 cm$^{-1}$. $^1$H NMR (300 MHz, CDCl$_3$): δ 7.45 (d, J=3 Hz, 1H); 7.27 (d, J=9 Hz, 1H); 7.07 (dd, J=3,9 Hz, 1H); 5.20 (s, 1H); 3.66 (s, 3H); 2.65–2.80 (m, 2H); 2.27–2.42 (m, 2H); 1.60–1.90 (m, 5H); 1.34 (s, 3H) and 1.25 (s, 3H). MS(FD): m/e 302(M+).

Elemental Analysis for C$_{18}$H$_{22}$O$_4$: Calcd: C, 71.50; H, 7.33; Found: C, 71.22; H, 7.19.

EXAMPLE 69

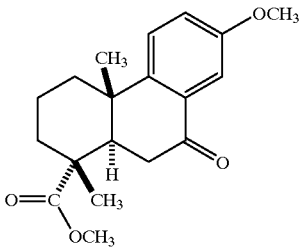

The compound was prepared substantially in accordance with the procedure detailed in Matsumoto et al., Bull. Chem. Soc. Jpn., vol. 61, 723–727 (1988), using the compound of Example 68.

Yield: 86%. IR (CHCl$_3$): 2941, 1722, 1677 and 1252 cm$^{-1}$. $^1$H NMR (300 MHz, CDCl$_3$): δ 7.48 (d, J=3 Hz, 1H); 7.29 (d, J=9 Hz, 1H); 7.11 (dd, J=3,9 Hz, 1H); 3.84 (s, 3H); 3.66 (s, 3H); 2.70 (m, 2H); 2.30–2.43 (m, 2H); 1.60–1.90 (m, 5H); 1.34 (s, 3H) and 1.25 (s, 3H). MS(FD): m/e 316(M+).

Elemental Analysis for C$_{19}$H$_{24}$O$_4$: Calcd: C, 72.13; H, 7.65; Found: C, 72.16; H, 7.35.

EXAMPLE 70

A.

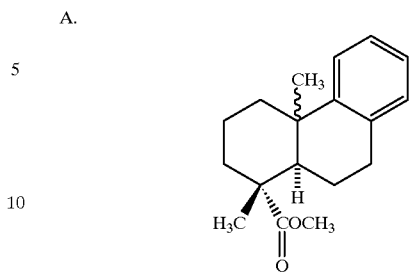

A mixture of 475 mg (1.5 mmol) of the compound of Example 60B, 425 mg (3.19 mmol) of anhydrous aluminum chloride in 15 ml of toluene was stirred at room temperature for 2 hours, under N$_2$. The reaction mixture was partitioned between toluene and 1N HCl. The resultant layers were separated and the organic layer was washed with brine, dried over Na$_2$SO$_4$, filtered and concentrated in vacuo to provide an oil. This oil was purified using flash chromatography (SiO$_2$, eluent of 2% EtOAc in hexanes) to provide an oil which was crystallized from MeOH.

$^1$H NMR (300 MHz, CDCl$_3$): δ 7.00–7.30 (m, 4H); 3.30 (s, 1.5H); 3.28 (s, 1.5H); 2.90 (m, 2H); 2.30 (m, 2H); 2.00 (m, 1H); 1.40–1.80 (m, 6H); 1.30 (s, 1.5H); 1.22 (s, 3H) and 1.10 (s,

B.

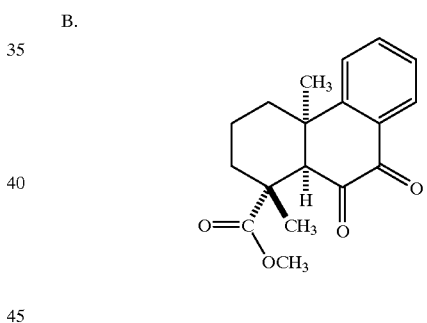

A solution of 285 mg (2.8 mmol) of chromium trioxide in 4 ml of glacial AcOH and 1 ml of H$_2$O was added drop-wise to a solution of 275 mg (1 mmol) of the compound of Example 70A in 5 ml of glacial AcOH. The reaction mixture was stirred at room temperature for 2 hours and then partitioned between EtOAc and brine (twice). The combined organic layers were dried over Na$_2$SO$_4$, filtered and then concentrated in vacuo to provide a yellow oil. This oil was purified using flash chromatography (SiO$_2$, eluent of 5% EtOAc in hexanes) to provide a bright yellow solid.

Yield: 50 mg (17%). m.p. 121–123° C. IR(CHCl$_3$) : 3019, 2954, 1727, 1688 and 1248 cm$^{-1}$. $^1$H NMR (300 MHz, CDCl$_3$ ): δ 8.14 (d, J=8 Hz, 1H); 7.70 (7, J=7 Hz, 1H); 7.47 (m, 2H); 3.73 (S, 3H); 3.39 (s, 1H); 2.64 (d, J=12 Hz, 1H); 2.01–2.11 (m, 1H); 1.40–1.80 (m, 4H); 1.29 (s, 3H) and 0.69 (s, 3H). MS(FD): m/e 300(M+).

Elemental Analysis for C$_{18}$H$_{20}$O$_4$: Calcd: C, 71.98; H, 6.71; Found: C, 72.10; H, 6.66.

C.

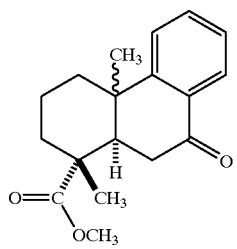

The compound was isolated from the reaction mixture described in Example 70B.

Yield: 136 mg of an oil (47.5%). $^1$H NMR (300 MHz, CDCl$_3$): δ 8.01 (m, 1H); 7.55 (m, 1H); 7.30 (m, 2H); 3.30 (s, 1.5H); 3.28 (s, 1.5H); 3.10 (dd, J=4.12 Hz, 0.5H); 2.70 (m, 1.5H); 2.40 (m, 2H); 1.40–1.90 (m, 5H); 1.30 (s, 1.5H); 1.28 (s, 1.5H); 1.23 (s, 1.5H); 0.65 (s, 1.5H).

EXAMPLE 71

A.

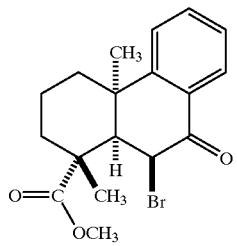

A solution of 0.9 ml (17 mmol) of bromine in 30 ml of anhydrous Et$_2$O was added to a solution of 3.8 g (13.3 mmol) of the compound of Example 70C in 200 ml of anhydrous Et$_2$O, dropwise. The reaction mixture was stirred at room temperature for 1 hour and then washed sequentially with H$_2$O, a saturated NaHCO$_3$ solution and 19% sodium thiosulfate, dried over Na$_2$SO$_4$, filtered and concentrated in vacuo to provide a residue which was purified using flash chromatography (eluent of 3:2 CH$_2$Cl$_2$/hexanes).

Yield: 1.2 g of yellowish oil (25%). $^1$H NMR (300 MHz, CDCl$_3$): δ 8.00 (dd, J=2,5 Hz, 1H); 7.60 (dt, J=2,5 Hz, 1H); 7.40 (m, 2H); 4.60 (s, 1H); 3.78 (s, 3H); 3.25 (s, 1H) 2.50 (d, J=7 Hz, 1H); 1.60–1.90 (m, 5H); 1.60 (s 3H); 0.57 (s, 3H).

B.

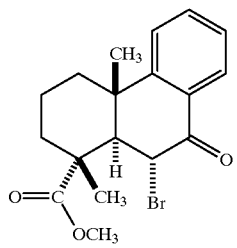

The compound was isolated from the reaction mixture described in Example 71A.

Yield: 1.2 g of an oil (25%). $^1$H NMR (300 MHz, CDCl$_3$): δ 8.01 (d, J=6 Hz, 1H); 7.60 (m, 1H); 7.40 (m, 2H); 5.00 (d, J=9 Hz, 1H); 3.65 (s, 3H); 3.23 (d, J=9 Hz, 1H); 2.60 (m, 1H); 2.38 (d, J=7 Hz, 1H); 1.80 (m, 4H); 1.52 (s, 3H) and 1.25 (s, 3H).

EXAMPLE 72

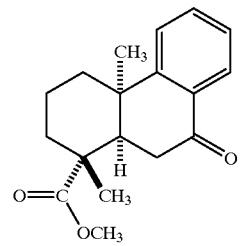

A mixture of 1.2 g (3.3 mmol) of the compound of Example 71A, 450 mg (6.9 mmol) of zinc dust, 225 mg (2.7 mmol) of NaOAc and 50 ml of glacial AcOH was refluxed for 1 hour, under N$_2$. After cooling, the reaction mixture was filtered and the filtrate was partitioned between Et$_2$O and brine. The resultant layers were separated and the organic layer was dried over Na$_2$SO$_4$, filtered and then concentrated in vacuo. The crude material was purified using flash chromatography (SiO$_2$, eluent of 10% Et$_2$O in hexanes).

Yield: 897 mg of a pale yellow oil (93%). IR(CHCl$_3$): 3018, 1721, 1675 and 1257 cm$^{-1}$. $^1$H NMR (300 MHz, CDCl$_3$): δ 8.03 (m, 1H); 7.55 (m, 1H); 7.30 (m, 2H); 3.69 (s, 3H); 3.13 (dd, J=7,19 Hz, 1H); 2.76 (dd, J=3,7 Hz, 1H); 2.50 (d, J=3 Hz, 1H); 2.45 (7, J=3 Hz, 1H); 1.88 (m, 1H); 1.58 (m, 4H); 1.33 (s, 3H) and 0.69 (s, 3H). MS(FD): m/e 286(M+).

Elemental Analysis for C$_{18}$H$_{22}$O$_3$: Calcd: C, 75.50; H, 7.74; Found: C, 75.75; H, 7.89.

EXAMPLE 73

A.

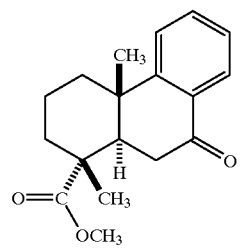

The compound was prepared substantially in accordance with the procedure detailed in Example 72, using 960 mg (2.6 mnmol) of the compound of Example 71B, 4.0 g (61.2 mmol) of zinc dust, 2.0 g (24.4 mmol) of NaOAc and 50 ml of glacial AcOH. The crude material was purified using column chromatography.

Yield: 500 mg of an oil (67.2%). IR(CHCl$_3$): 3028, 1722, 1679, 1258 cm$^{-1}$. $^1$H NMR (300 MHz, CDCl$_3$): δ 8.01 (d, J=8 Hz, 1H); 7.54 (7, 6 Hz, 1H); 7.29 (m, 2H); 3.67 (s, 3H); 2.74 (dd, J=3,7 Hz, 2H); 2.30–2.45 (m, 2H); 1.60–1.90 (m, 5H); 1.36 (s, 3H) and 1.28 (s, 3H). MS(FD): m/e 286(M+).

B.

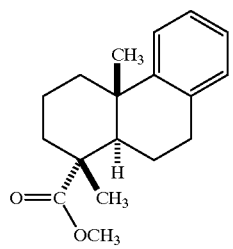

The compound was isolated from the reaction mixture described in Example 73A

Yield: 150 mg (21%).

EXAMPLE 74

A.

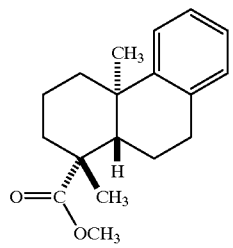

A solution of 1.54 g (5.66 mmol) of the compound of Example 70A and 1.5 g of 10% Pd/C in 150 ml of triethyleneglycol dimethyl ether was refluxed for 3 hours, under $N_2$. After cooling, the mixture was filtered and the filtrate was partitioned between EtOAc and brine (three times). The resultant layers were separated and the combined organic layers were dried over $Na_2SO_4$, filtered and the concentrated in vacuo to provide 1.5 g of a residue. A fraction of this residue (300 mg) was purified by chromatotron (eluent of 2% $CH_2Cl_2$ in hexanes initially, followed by the addition to the mobile phase of 50 ml of $CH_2Cl_2$ after 200 ml elution, and finally 4 ml of EtOAc after 300 ml had eluted).

Yield: 29 mg $^1$H NMR (300 MHz, $CDCl_3$): δ 7.00–7.30 (m, 4H); 3.63 (s, 3H); 2.83 (m, 2H); 2.50 (m, 3H); 2.00 (m, 2H); 1.30–1.70 (m, 3H); 1.25 (s, 3H); 1.10 (m, 1H); 1.02 (s, 3H).

B.

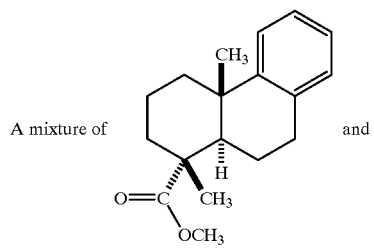

B.

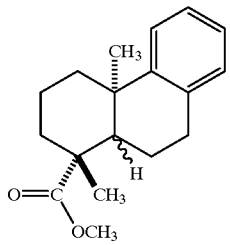

The compounds were isolated from the reaction mixture described in Example 74A.

Yield: 216 mg.

C.

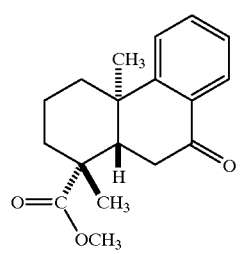

The compound was prepared substantially in accordance with the procedure detailed in Example 70B, using 70 mg (0.26 mmol) of the compound of Example 74A.

Yield: 30 mg of an off-white solid (40.3%). m.p. 143–145° C. IR($CHCl_3$): 2951, 1718 and 1687 cm$^{-1}$. $^1$H NMR (300 MHz, $CDCl_3$): δ 8.05 (d, J=7 Hz, 1H); 7.54 (m, 1H); 7.42 (d, J=7 Hz, 1H); 7.31 (d, J=7 Hz, 1H); 3.66 (s, 3H); 3.23 (dd, J=14,18 Hz, 1H); 3.00 (dd, J=3,18 Hz, 1H); 2.30–2.45 (m, 2H); 2.00–2.20 (m, 2H); 1.65–1.80 (m, 1H); 1.63 (m, 1H); 1.27 (s, 3H); 1.13 (s, 3H) and 1.12 (m, 1H). MS(FD): m/e 286(M+).

Elemental Analysis for $C_{18}H_{22}O_3$: Calcd: C, 75.50; H, 7.74; Found: C, 75.78; H, 7.63.

EXAMPLE 75

A.

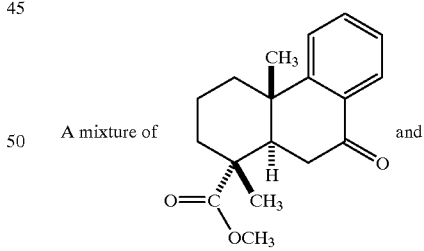

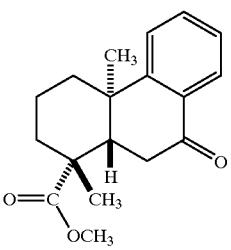

The compounds were prepared substantially in accordance with the procedure detailed in Example 70B, using a solution of 325 mg (1.2 mmol) of the unpurified residue from Example 74A in 5 ml of glacial AcOH The crude material was purified using flash chromatography (SiO$_2$, eluent of 15% Et$_2$O in hexanes).

Yield: 62 mg of an oil.

B.

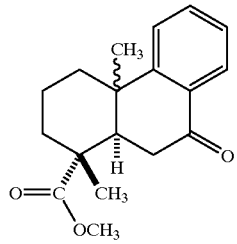

The compound was isolated from the reaction mixture described in Example 75A.

Yield: 78 mg of an oil.

Note: The reaction mixture also provided 16 mg of the compound of Example 74C and 75 mg of the compound of Example 70A.

EXAMPLE 76

A.

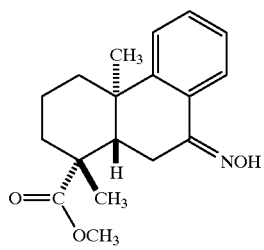

The compound was prepared substantially in accordance with the procedure detailed in Example 62, using a solution containing 140 mg (0.49 mmol) of the compounds of Example 75A in 10 ml of MeOH. The crude material was purified using flash chromatography (SiO$_2$, eluent of 20% Et$_2$O in hexanes).

Yield: 38 mg of a solid (26%). m.p. 139–141° C. IR(CHCl$_3$): 3584, 3020 and 1720 cm$^{-1}$. $^1$H NMR (300 MHz, CDCl$_3$): δ 7.92 (d, J=7.7 Hz, 1H); 7.56 (s, 1H); 7.30 (m, 2H); 7.20 (m, 1H); 3.72 (s, 3H); 3.44 (dd, J=4.0,18.4 Hz, 1H); 3.12 (dd, J=14.0,18.7 Hz, 1H); 2.35 (m, 2H); 2.03 (m, 1H); 1.50–1.80 (m, 3H); 1.32 (s, 3H); 1.10 (m, 1H) and 1.02 (s, 3H). MS(FD): m/e 301(M+).

Elemental Analysis for C$_{18}$H$_{23}$NO$_3$: Calcd: C, 71.74; H, 7.69; N, 4.65; Found: C, 71.97; H, 7.77; N, 4.39.

B.

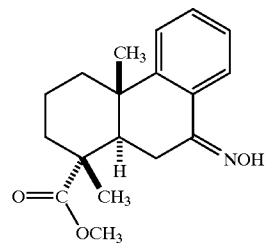

The compound was isolated from the reaction mixture described in Example 76A.

Yield: 38 mg of a resin (26%). IR(CHCl$_3$): 3583, 3027, 2935, 1721 and 1263 cm$^{-1}$. $^1$H NMR (300 MHz, CDCl$_3$): δ 7.85 (d, J=8.1 Hz, 1H); 7.43 (s, 1H); 7.10–7.20 (m, 3H); 3.66 (s, 3H); 2.67 (d, J=8.8 Hz, 2H); 2.28–2.37 (m, 2H); 1.76 (m, 4H); 1.39 (s, 3H); 1.26 (m, 1H) and 1.14 (s, 3H). MS(FD): m/e 301(M+).

EXAMPLE 77

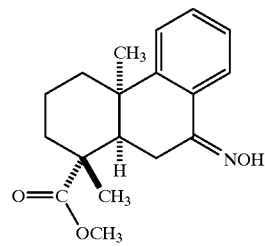

The compound was prepared substantially in accordance with the procedure detailed in Example 62, using the compound of Example 72.

Yield: 98%. IR(CHCl$_3$): 3583, 2952 and 1720 cm$^{-1}$. $^1$H NMR (300 MHz, CDCl$_3$): δ 7.86 (d, J=8.8 Hz, 1H); 7.20–7.38 (m, 4H); 3.70 (s, 3H); 3.10 (dd, J=8.1,19.8 Hz, 1H); 2.53–2.64 (m, 2H); 2.47 (d, 11.4 Hz, 1H); 1.70–1.90 (m, 1H); 1.40–1.60 (m, 4H); 1.19 (S, 3H) and 0.56 (s, 3H). MS(FD): m/e 302 (M+).

Elemental Analysis for C$_{18}$H$_{23}$NO$_3$: Calcd: C, 71.73; H, 7.69; N, 4.65; Found: C, 71.79; H, 7.78, N, 4.44.

EXAMPLE 78

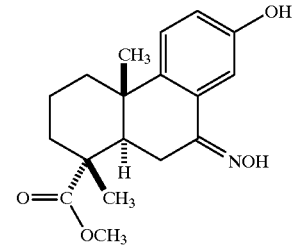

The compound was prepared substantially in accordance with the procedure detailed in Example 62, using the compound of Example 68.

IR(KBr): 3393, 2932, 1727 and 1702 cm$^{-1}$. $^1$H NMR (300 MHz, CDCl$_3$): δ 8.00 (brs, 1H); 7.29 (d, J=3 Hz, 1H); 7.16 (d, J=9 Hz, 1H); 6.85 (dd, J=3,9 Hz, 1H); 5.25 (brs, 1H);

3.68 (s, 3H); 2.65 (m, 2H); 2.20–2.40 (m, 2H); 1.55–2.04 (m, 5H); 1.40 (s, 3H) and 1.10 (s, 3H). MS(FD): m/e 318 (M+).

Elemental Analysis for $C_{18}H_{23}O_4$: Calcd: C, 68.12; H, 7.30; N, 4.41; Found: C, 67.95; H, 7.46; N, 4.12.

EXAMPLE 79

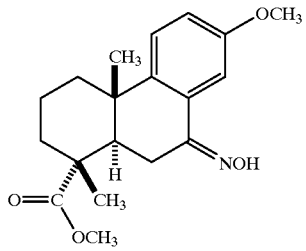

The compound was prepared substantially in accordance with the procedure detailed in Example 62, using the compound of Example 69.

Yield: 93%. IR(KBr): 3421, 2936, 1727 cm$^{-1}$. $^1$H NMR (300 MHz, CDCl$_3$): δ 7.37 (d, J=3 Hz, 1H); 7.29 (s, 1H); 6.92 (d, J=9 Hz, 1H); 6.91 (dd, J=3,9 Hz, 1H); 3.81 (s, 3H); 3.66 (s, 3H); 2.65 (m, 2H); 2.25–2.65 (m, 2H); 1.60–1.80 (m, 5H); 1.38 (s, 3H) and 1.11 (s, 3H). MS(FD): m/e 331(M+).

Elemental Analysis for $C_{19}H_{25}NO_4$: Calcd: C, 68.86; H, 7.60; N, 4.23' Found: C, 69.10; H, 7.83; N, 4.23.

EXAMPLE 80

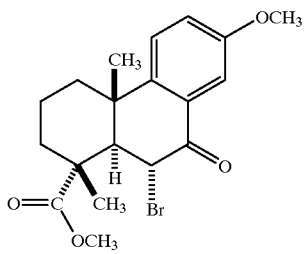

The compound was prepared substantially in accordance with the procedure detailed in Example 71A, using the compound of Example 69.

Yield: 74% m.p. 146–148° C. IR(KBr): 2900, 1725 and 1679 cm$^{-1}$. $^1$H NMR (300MHz, CDCl$_3$): δ 7.46 (d, J=3 Hz, 1H); 7.28 (d, J=9 Hz, 1H); 7.14 (dd, J=3,9 Hz, 1H); 4.98 (d, J=13 Hz, 1H); 3.85 (s, 3H); 3.65 (s, 3H); 3.20 (d, J=13Hz, 1H); 2.35 (m, 1H); 1.70–1.90 (m, 5H); 1.50 (s, 3H); 1.26 (s, 3H). MS(FD): m/e 397 (M+).

Elemental Analysis for $C_{19}H_{23}BrO_4$: Calcd: C, 57.73; H, 5.86; Found: C, 57.78; H, 6.06.

EXAMPLE 81

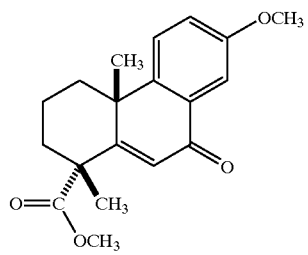

To a solution of 200 mg (0.506 mmol) of the compound of Example 80 in 5 ml of anhydrous MeOH, was slowly added a solution of NaOMe (prepared in situ by dissolving 34 mg of Na in 1 ml of anhydrous MeOH). The reaction mixture was refluxed for 2 hours, cooled and diluted with 30 ml of brine, under N$_2$. The resulting layers were separated and the organic layer was dried over Na$_2$SO$_4$, filtered and concentrated to provide an oily resin which was purified using flash chromatography (gradient eluent of 0–2% EtOAc in CH$_2$Cl$_2$).

Yield: 140 mg of a yellowish oil (88%). IR(CHCl$_3$) 3009, 2952, 1728 and 1610 cm$^{-1}$. $^1$H NMR (300 MHz, CDCl$_3$): δ 7.57 (d, J=3 Hz, 1H); 7.43 (d, J=9 Hz, 1H); 7.15 (dd, J=3,9 Hz, 1H); 6.15 (s, 1H); 3.88 (s, 3H); 3.73 (s, 3H); 2.48 (d, J=13 Hz, 1H); 2.18–2.29 (m, 1H); 1.71–2.07 (m, 4H); 1.56 (s, 3H) and 1.52 (s, 3H). MS(FD): m/e 314 (M+).

Elemental Analysis for $C_{19}H_{22}O_4 \cdot 0.25H_2O$: Calcd: C, 71.54; H, 7.05; Found: C, 71.71; H, 7.14.

EXAMPLE 82

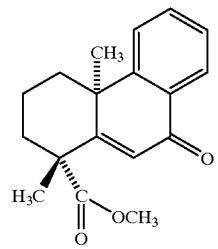

The compound was prepared substantially in accordance with the procedure detailed in Example 81, using the compound of Example 71A.

IR(CHCl$_3$): 2952, 1728 and 1653 cm$^{-1}$. $^1$H NMR (300 MHz, CDCl$_3$): δ 8.19 (d, J=8 Hz, 1H); 7.57 (m, 2H); 7.41 (s, J=8 Hz, 1H); 6.62 (s, 1H); 3.65 (s, 3H); 2.54 (d, J=14 Hz, 1H); 2.40 (d, J=13 Hz, 1H); 1.90–2.20 (m, 1H); 1.85 (m, 1H); 1.58 (m, 1H); 1.51 (s, 3H) and 1.34 (s, 3H); 1.25 (m, 1H). MS(FD): m/e 284 (M+).

Elemental Analysis for $C_{18}H_{20}O_3 \cdot 5H_2O$: Calcd: C, 73.74; H, 7.16; Found: C, 73.80; H, 7.15.

EXAMPLE 83

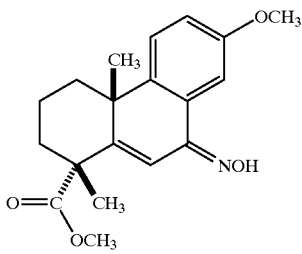

The compound was prepared substantially in accordance with the procedure detailed in Example 62, using the compound of Example 81.

Yield: 50%. IR(KBr): 3411, 2950 and 1729 cm$^{-1}$. $^1$H NMR (300 MHz, CDCl$_3$): δ 7.42 (d, J=3 Hz, 1H); 7.34 (s, 1H); 7.31 (d, J=9 Hz, 1H); 6.96 (dd, J=3, 9 Hz, 1H); 6.80 (s, 1H); 3.84 (s, 3H); 3.71 (s, 3H); 2.40 (d, J=13 Hz, 1H); 2.13–2.24 (m, 1H); 1.72–2.01 (m, 4H); 1.63 (s, 3H) and 1.40 (s, 3H). MS(FD): m/e 329 (M+)

EXAMPLE 84

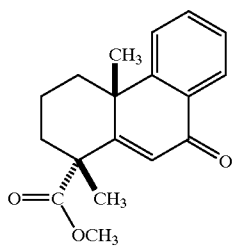

The compound was prepared substantially in accordance with the procedure detailed in Example 81, using the compound of Example 71B.

Yield: 47%. IR(CHCl$_3$): 2954, 1728 and 1653 cm$^{-1}$. $^1$H NMR (300 MHz, CDCl$_3$): δ 812 (d, J=7.7 Hz, 1H); 7.55 (m, 2H); 7.39 (s, J=7.7 Hz, 1H); 6.18 (s, 1H); 3.73 (s, 3H); 2.55 (m, 1H); 2.23 (m, 1H); 1.80–2.10 (m, 3H); 1.60 (m, 1H) and 1.55 (s, 6H). MS(FD): m/e 284 (M+).

Elemental Analysis for C$_{18}$H$_{20}$O$_3$: Calcd: C, 76.03; H, 7.09; Found: C, 75.77; H, 7.20.

EXAMPLE 85

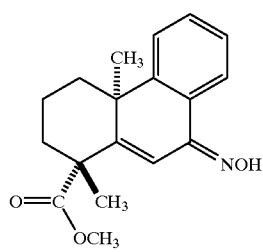

The compound was prepared substantially in accordance with the procedure detailed in Example 62, using the compound of Example 82.

Yield: 58.5%. m.p. 175–180° C. IR(KBr): 3426, 2932 and 1702 cm$^{-1}$. $^1$H NMR (300 MHz, CDCl$_3$): δ 8.02 (d, J=7.3 Hz, 1H); 7.80 (s, 1H); 7.39 (m, 2H); 7.32 (s, 1H); 7.23 (d, J=8.1 Hz, 1H); 3.65 (s, 3H); 2.47 (d, J=13.2 Hz, 1H); 2.32 (d, J=14.3 Hz, 1H); 1.95–2.18 (m, 2H); 1.70 (m, 1H); 1.54 (s, 3H); 1.28 (s, 3H) and 1.23 (m, 1H). MS(FD)m/e 299 (M+).

EXAMPLE 86

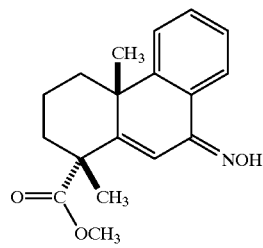

The compound was prepared substantially in accordance with the procedure detailed in Example 62, using the compound of Example 84.

Yield: 62. m.p. 131–134° C. IR(KBr): 3266, 2955 and 1722 cm$^{-1}$. $^1$H NMR (300 MHz, CDCl$_3$): δ 7.92 (d, J=7.7 Hz, 1H); 7.79 (s, 1H); 7.40 (m, 2H); 7.27 (m, 1H); 6.83 (s, 1H); 3.71 (s, 3H); 2.44 (d, J=12.8 Hz, 1H); 2.14–2.24 (m, 1H); 1.74–1.98 (m, 4H); 1.64 (s, 3H) and 1.42 (s, 3H). MS(FD): m/e 299 (M+).

EXAMPLE 87

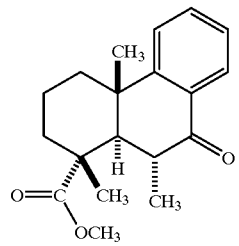

To a stirring solution of 70 mg (0.245 mmol) of the compound of Example 73A in 20 ml of anhydrous THF, was added 32 mg (0.80 mmol) of 60% NaH on mineral oil, under N$_2$. The resultant mixture was stirred 15 minutes followed by the addition of 0.15 ml (2.25 mmol) of iodomethane, via syringe. The reaction mixture was stirred for 3 hours, quenched by the dropwise addition of H$_2$O and then partitioned between Et$_2$O and H$_2$O. The resultant layers were separated and the organic layer was dried over Na$_2$SO$_4$, filtered and concentrated in vacuo to provide a residue which was purified by radial chromatography (eluent of 10% Et$_2$O in hexanes).

Yield: 16 mg of a clear oil (22%). IR(CHCl$_3$): 3692, 3022, 2950, 1724 and 1678 cm$^{-1}$. $^1$H NMR (300 MHz, CDCl$_3$): δ 7.95 (d, J=7.7 Hz, 1H); 7.54 (s, J=8.8 Hz, 1H); 7.25 (m, 2H); 3.63 (s, 3H); 2.80 (m, 2H); 2.39 (d, J=7.7 Hz, 1H); 1.70–2.05 (m, 5H); 1.43 (s, 3H); 1.28 (s, 3H) and 1.13 (d, J=6.2 Hz, 3H) MS(FD): m/e 300 (M+).

Elemental Analysis for $C_{19}H_{24}O_3$: Calcd: C, 75.97; H, 8.05; Found: C, 75.80; H, 7.96.

EXAMPLE 88

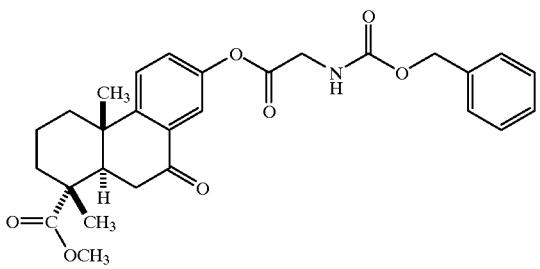

A mixture of 50 mg (0.165 mmol) of the compound of Example 68, 35 mg (0.165 mmol) of carbobenzyloxyglycine, 35 mg (0.170 mmol) of 1,3-dicyclohexylcarbodiimide (DCC), 2 mg (0.0165 mmol) of 4-dimethylaminopyridine in 25 ml of anhydrous $Et_2O$ was stirred for 16 hours resulting in the formation of a solid. This solid was removed by filtration and the filtrate was washed sequentially with $H_2O$, a 5% AcOH solution and brine. The combined organic layers were dried over $Na_2SO_4$, filtered and then concentrated in vacuo to provide a resin which was purified using flash chromatography ($SiO_2$, eluent of 20% $Et_2O$ in hexanes).

Yield: 54 mg of a light yellow solid (66%). IR(KBr): 3330, 2934, 1779, 1725, 1685 cm$^{-1}$. $^1$H NMR (300 MHz, CDCl$_3$): δ 7.70 (s, 1H); 7.36 (m, 8H); 6.20 (s, 2H); 4.26 (d, J=6 Hz, 2H); 3.67 (s, 3H); 2.73 (dd, J=3,6 Hz, 2H); 2.40 (m, 2H); 1.50–2.00 (m, 5H); 1.35 (s, 3H); 1.28 and (s, 3H). MS(FD): m/e 494 (M+).

EXAMPLE 89

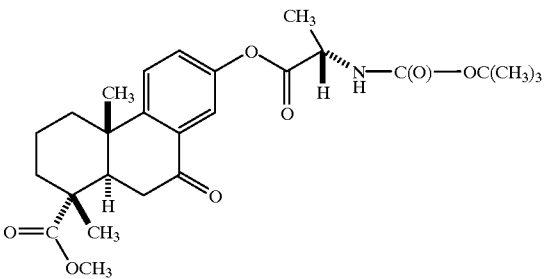

The compound was prepared substantially in accordance with the procedure detailed in Example 88, using the compound of Example 68 and N-t-butoxycarbonyl-L-alanine.

Yield: 96%. IR(CHCl$_3$): 3444, 2938, 1763, 1714 cm$^{-1}$. $^1$H NMR (300 MHz, CDCl$_3$ ): δ 7.69 (d, J=2.6 Hz, 1H); 7.41 (d, J=8.5 Hz, 1H); 7.30 (d, J=2.6 Hz, 1H); 5.10 (brm, 1H); 4.55 (brm, 1H); 3.65 (s, 3H); 2.73 (dd, J=3.3, 6.6 Hz, 2H); 2.32–2.42 (m, 2H); 1.70–2.20 (m, 5H); 1.55 (d, J=7.0Hz, 3H); 1.47 (s, 6H); 1.43 (s, 3H); 1.35 (s, 3H) and 1.28 (s, 3H), MS(FD) m/e 474 (M+).

EXAMPLE 90

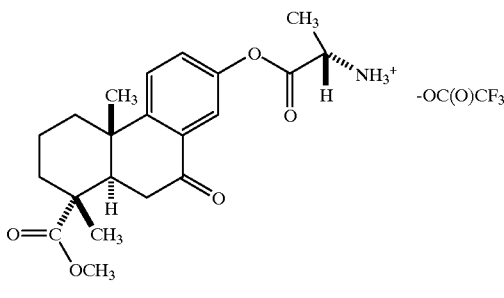

A mixture of 100 mg (0.21 mmol) of the compound of Example 89 in 2 ml of $CH_2Cl_2$ was added to 2 ml of a 1:1 $CH_2Cl_2/CF_3COOH$ mixture. After stirring for 1 hour, the reaction mixture was concentrated in vacuo. The resultant residue was concentrated repetitively in $Et_2O$ until a foam was obtained.

Yield: 85 mg (83%). IR(CHCl$_3$): 2941, 1715, 1711 and 1682 cm$^{-1}$. $^1$H NMR (300 MHz, CDCl$_3$): δ 7.65 (m, 2H); 7.41 (d, J=8.1 Hz, 1H); 4.30 (m, 1H); 3.62 (s, 3H); 2.63 (m, 2H); 2.25–2.40 (m, 2H); 1.60–1.90 (m, 5H); 1.34 (s, 3H) and 1.24 (s, 3H); 1.22 (d, J=7.0Hz, 3H). MS(FD): m/e 374, free base (M+)

EXAMPLE 91

A.

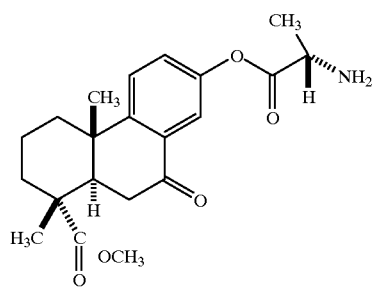

To a solution of 550 mg (1.0 mmol) of the compound of Example 89 in 10 ml of $CH_2Cl_2$, was added 3 ml (39 mmol) of $CF_3COOH$. After stirring for 1 hour, the reaction mixture was concentrated in vacuo to provide a foam. This foam was dissolved in 20 ml of $CH_2Cl_2$ followed by the addition of 0.17 ml (1.2 mmol) of $Et_3N$. The resultant layers were separated and the organic layer was washed with $H_2O$, dried over $Na_2SO_4$, filtered and concentrated in vacuo to provide a foam.

B.

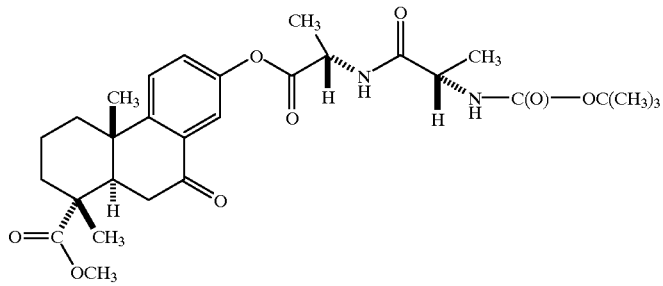

The compound was prepared substantially in accordance with the procedure detailed in Example 88, using the compound of Example 91A and 230 mg (1.2 mmol) of N-t-butyloxycarbonyl-L-alanine Yield: 255 mg (47%). IR(KBr): 3334, 2938, 1770, 1725 and 1687 cm$^{-1}$. $^1$H NMR (300 MHz, CDCl$_3$): δ 7.69 (d, J=3 Hz, 1H); 7.41 (d, J=9 Hz, 1H); 7.29 (d, J=3 Hz, 1H); 6.70 (m, 1H); 5.00 (m, 1H); 4.80 (m, 1H); 4.20 (m, 1H); 3.67 (s, 3H); 2.73 (m, 2H); 2.36 (m, 2H); 1.60–1.90 (m, 5H); 1.58 (d, J=7 Hz, 3H); 1.45 (s, 9H); 1.38 (d, J=7 Hz, 3H); 1.35 (s, 3H) and 1.27 (s, 3H) MS(FD): m/e 544 (M+).

Elemental Analysis for $C_{29}H_{40}N_2O_8 \cdot 0.75H_2O$: Calcd: C, 62.40; H, 7.43; N, 5.02; Found: C, 62.30; H, 7.24; N, 4.77.

EXAMPLE 92

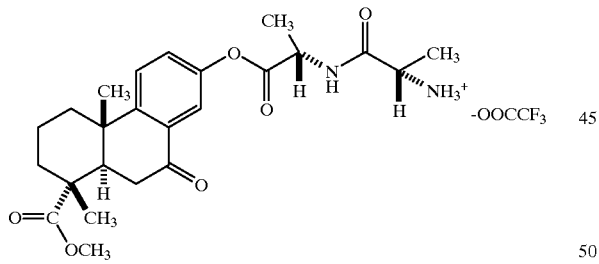

The compound was prepared substantially in accordance with the procedure detailed in Example 90, using the compound of Example 91B.

Yield: 95%. IR(KBr): 2950, 1770 and 1681 cm$^{-1}$. $^1$H NMR (300 MHz, CDCl$_3$): δ 8.17 (brs, 3H); 7.60 (s, 1H); 7.40 (d, J=2.6 Hz, 1H); 7.27 (m, 1H); 4.65 (brs, 1H); 4.40 (brs, 1H); 3.70 (d, J=2 Hz, 1H); 3.62 (s, 3H); 2.70 (m, 7H); 2.35 (m, 2H); 1.50–1.85 (m, 6H); 1.32 (s, 3H) and 1.23 (s, 3H). MS(FD): m/e 445 free base (M+).

EXAMPLE 93

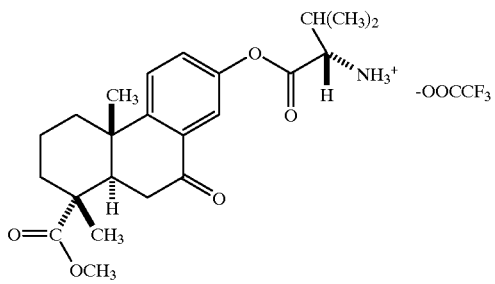

The compound was prepared substantially in accordance with the procedure detailed in Example 88, using the compound of Example 68 and N-t-butoxycarbonyl-L-valine.

Yield: 47%. IR(KBr) 3377, 2969, 1766, 1724 and 1688 cm$^{-1}$. $^1$H NMR (300 MHz, CDCl$_3$): δ 7.68 (d, J=2.6 Hz, 1H); 7.41 (d, J=8.8 Hz, 1H); 7.29 (d, J=2.6 Hz, 1H); 5.06 (brm, 1H); 4.45 (brm, 1H); 3.65 (s, 3H); 2.74 (dd, J=3.3,7.0 Hz, 2H); 2.30–2.43 (m, 1H); 1.70–1.90 (m, 6H); 1.48 (s, 9H); 1.35 (s, 3H); 1.28 (s, 3H); 1.09 (d, J=6.6 Hz, 3H); 1.02 (d, J=7.0 Hz, 3H). MS(FD): m/e 502 (M+).

Elemental Analysis for $C_{28}H_{39}NO_7$: Calcd: C, 67.04; H, 7.84; N, 2.79; Found: C, 66.82; H, 7.73; N, 2.58.

EXAMPLE 94

The compound was prepared substantially in accordance with the procedure detailed in Example 90, using the compound of Example 93.

Yield: 99% yield. IR(KBr): 3068, 2943, 1758, 1722 and 1668 cm$^{-1}$. $^1$H NMR (300 MHz, CDCl$_3$): δ 7.68 (m, 1H); 7.40 (m, 2H); 4.08 (d, J=4.8 Hz, 1H); 3.65 (s, 3H); 2.70 (m, 2H); 2.30–2.40 (m, 2H); 1.70–1.90 (m, 6H); 1.34 (s, 3H); 1.26 (s, 3H); 1.16 (d, J=2.9 Hz, 3H) and 1.14 (d, J=2.9 Hz, 3H). MS(FD): m/e free base 402 (M+).

Elemental Analysis for $C_{25}H_{32}NO_7$: Calcd: C, 58.25; H, 6.26; N, 2.72; Found: C, 57.98; H, 6.32; N, 2.64.

EXAMPLE 95

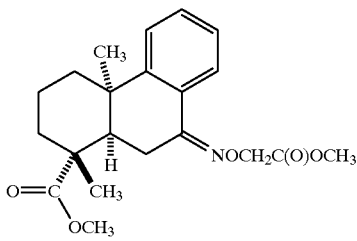

To a solution of 295 mg (0.98 mmol) of the compound of Example 77 in 5 ml of anhydrous DMF, was added 60 mg (1.50 mmol) of 60% NaH on mineral oil, under $N_2$, followed by the addition of 0.18 ml (1.90 mmol) of methyl bromoacetate was added by syringe. The reaction mixture was stirred for 1 hour and then cautiously quenched by the dropwise addition of brine under $N_2$. The reaction mixture was partitioned between brine and $Et_2O$, the resulting layers were separated and the organic layer was dried over $Na_2SO_4$, filtered and the concentrated in vacuo to provide an oil which was purified using flash chromatography ($SiO_2$, eluent of 20% $Et_2O$ in hexanes).

Yield: 175 mg of a clear oil (48%). IR(CHCl$_3$): 2953, 1737 and 1725 cm$^{-1}$. $^1$H NMR (300 MHz, CDCl$_3$): δ 7.87 (d, J=8 Hz, 1H); 7.29 (m, 2H); 7.19 (s, J=8 Hz, 1H); 4.75 (s, 2H); 3.76 (s, 3H); 3.69 (s, 3H); 3.17 (dd, J=8,20 Hz, 1H); 2.35–2.57 (m, 3H); 1.73–1.85 (m, 1H); 1.44–1.61 (m, 4H); 1.20 (s, 3H) and 0.56 (s, 3H). MS(FD): m/e 373 (M+).

Elemental Analysis for $C_{21}H_{27}NO_5$: Calcd: C, 67.54; H, 7.29; N, 3.75; Found: C, 67.84; H, 7.58; N, 3.89.

EXAMPLE 96

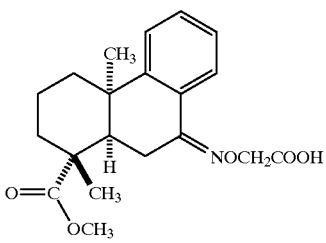

A mixture of 56.7 mg (0.152 mmol) of the compound of Example 95, 0.2 ml (0.2 mmol) of 1N NaOH and 5 ml of MeOH was stirred at room temperature for 4 days and then diluted to 30 ml with brine and extracted with EtOAc. The layers were separated and the aqueous layer was acidified with 5N HCl and extracted with EtOAc. The combined organic layers were dried over $Na_2SO_4$, filtered and then concentrated in vacuo.

Yield: 45.7 mg of an amorphous tan resin (84%). IR(CHCl$_3$): 3030, 2951 and 1720 cm$^{-1}$. $^1$H NMR (300 MHz, CDCl$_3$): δ 12.75 (brs, 1H); 7.76 (d, J=8 Hz, 1H); 7.40 (m, 2H); 7.21 (m, 1H); 4.66 (s, 2H); 3.62 (s, 3H); 3.05 (dd, J=8,20 Hz, 1H); 2.47 (m, 3H); 1.60–1.80 (m, 1H); 1.20–1.59 (m, 4H); 1.10 (s, 3H) and 0.42 (s, 3H). MS(FD): m/e 359 (M+).

Elemental Analysis for $C_{20}H_{25}NO_5 \cdot 0.25H_2O$: Calcd: C, 66.05; H, 7.01; N, 3.85; Found: C, 65.91; H, 7.35; N, 3.61.

EXAMPLE 97

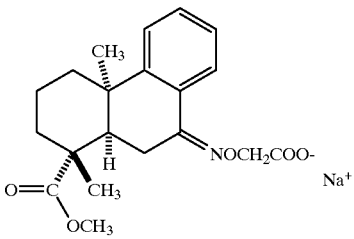

A mixture of 111.8 mg (0.31 mmol) of the compound of Example 96, 0.31 ml (0.31 mmol) of 1N NaOH and 10 ml of anhydrous CH3CN was sonicated for 30 minutes and then concentrated in vacuo to provide a residue. This residue was repetitively concentrated from fresh $Et_2O$ to provide an amorphous solid.

Yield: 116 mg (98%). IR(KBr): 3429, 2948, 1725 and 1611 cm$^{-1}$. $^1$H NMR (300 MHz, CDCl$_3$): δ 7.75 (d, J=7.4 Hz, 1H); 7.32 (m, 2H); 7.20 (m, 1H); 4.20 (s, 2H); 3.63 (s, 3H); 3.00 (dd, J=7.7,19.1 Hz, 1H); 2.35–2.50 (m, 3H); 1.60–1.80 (m, 1H); 1.40–1.60 (m, 4H); 1.10 (s, 3H) and 0.43 (s, 3H). MS(FD): m/e 285 (M+-$C_2H_2O_3$Na).

EXAMPLE 98

A.

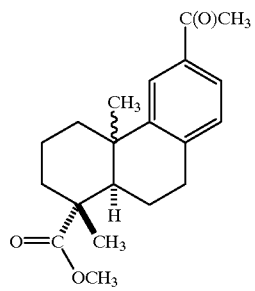

A mixture of 4.0 g (14.7 mmol) of the compound of Example 70A and 1.2 ml (16.9 mmol) of acetyl chloride in 60 ml of carbon disulfide to a suspension of 2.6 mg (19.5 mmol) of anhydrous aluminum chloride in 100 ml of carbon disulfide, via dropping funnel. The reaction mixture was refluxed for 1 hour and then the carbon disulfide was removed by downward distillation. The resultant residue was cautiously quenched by the addition of 100 ml of 0.2N HCl. The desired compound was extracted using 100 ml of $CH_2Cl_2$, dried over $Na_2SO_4$, filtered and then concentrated in vacuo to provide a dark red oil which was purified using flash chromatography ($SiO_2$, eluent of 20% $Et_2O$ in hexanes).

Yield: 1.7 g of an oil (87% based on recovered starting material). $^1$H NMR (300 MHz, CDCl$_3$): δ 7.90 (d, J=4 Hz, 1H); 7.75 (d, J=4 Hz, 0.5H); 7.63 (d, J=4 Hz, 0.5H); 7.37 (d, J=6 Hz, 0.5H); 7.10 (d, J=6 Hz, 0.5H); 3.70 (s, 1.5H); 3.68 (s, 1.5H); 2.92 (m, 2H); 2.60 (s, 3H); 2.00–2.50 (m, 3H); 1.40–1.98 (m, 6H); 1.29 (s, 1.5H); 1.26 (s, 1.5H); 1.24 (s, 1.5H) and 1.10 (s, 1.5H).

B.

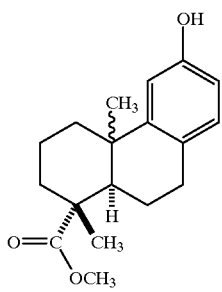

A mixture of 1.7 g (5.4 mmol) of the compound of Example 98A, 1.9 g (5.5 mmol) of 50% 3-chloroperoxybenzoic acid, 18 mg (0.095 mmol) of p-toluene sulfonic acid monohydrate in 25 ml of 1,2-dimethyoxyethane was refluxed for 3 hours, under $N_2$. After cooling, the reaction mixture was diluted with $Et_2O$ and washed sequentially with 10% potassium iodide, 10% sodium thiosulfate, a saturated $NaHCO_3$ solution and brine, dried over $Na_2SO_4$, filtered and then concentrated to provide a resin. This resin was dissolved in 25 ml of MeOH and 10 ml of $H_2O$ containing 1.6 g (19.0 mmol) of $NaHCO_3$. The resultant mixture was refluxed for 1.5 hours, cooled, filtered and concentrated in vacuo to provide a residue. This residue was partitioned between $H_2O$ and $Et_2O$. The resulting layers were separated and the organic layer was washed sequentially with 1N HCl and brine, dried over $Na_2SO_4$, filtered and concentrated in vacuo Yield: 1.55 g (99%). $^1$H NMR (300 MHz, $CDCl_3$) δ 6.85 (m, 1H); 6.70 (d, J=6 Hz, 1H); 6.55 (dd, J=6 Hz, 1H); 3.63 (s, 3H); 2.80 (m, 2H); 1.90–2.30 (m, 3H); 1.40–1.88 (m, 6H); 1.25 (s, 1.5H); 1.20 (s, 1.5H); 1.17 (s, 1.5H) and 1.02 (s, 1.5H).

C.

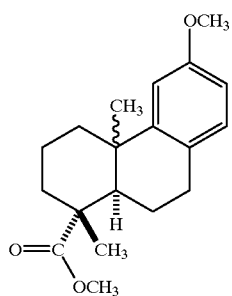

To a suspension of 1.55 g (5.4 mmol) of the compound of Example 98B and 275 mg (6.87 mmol) of 60% NaH on mineral oil in 50 ml of anhydrous DMF, was added 0.5 ml (7.50 mmol) of idodomethane, under $N_2$. The reaction mixture was stirred for 1 hour and then cautiously quenched by the dropwise addition of brine. The reaction mixture was partitioned between $Et_2O$ and brine. The resultant layers were separated and the organic layer was dried over $Na_2SO_4$, filtered and concentrated in vacuo to provide a residue which was purified using flash chromatography ($SiO_2$, eluent of 20% $Et_2O$ in hexanes).

Yield: 1.3 g of a clear light yellow oil (88.5% based on recovered starting material). $^1$H NMR (300 MHz, $CDCl_3$): δ 7.00 (d, J=6 Hz, 1H); 6.82 (m, 1H); 6.70 (m, 1H); 3.80 (s, 3H); 3.70 (s, 3H); 2.80 (m, 2H); 2.00–2.40 (m, 3H); 1.40–1.90 (m, 6H); 1.25 (s, 1.5H); 1.20 (s, 3H); 1.10 (s, 1.5H).

Note: The reaction mixture also contained 200 mg of the compound of Example 98A.

D.

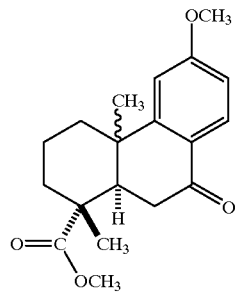

The compound was prepared substantially in accordance with the procedure detailed in Example 70B, using 1.3 g (4.3 mmol) of the compound of Example 98C. The crude material was purified using flash chromatography ($SiO_2$, eluent of 20% $Et_2O$ in hexanes).

Yield: 820 mg of an oil (60.5%). $^1$H NMR (300 MHz, $CDCl_3$): δ 8.00 (m, 1H); 6.80 (m, 2H); 3.87 (s, 1.5H); 3.85 (s, 1.5H); 3.63 (s, 1.5H); 3.61 (s, 1.5H); 3.01 (dd, J=5, 12 Hz, 0.5H); 2.70 (m, 1.5H); 2.40 (m, 2H); 1.40–1.95 (m, 5H); 1.32 (s, 1.5H); 1.30 (s, 1.5H); 1.22 (s, 1.5H); 0.65 (s, 1.5H).

E.

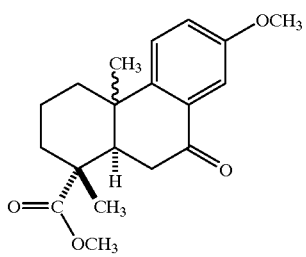

The compound was isolated from the reaction mixture described in Example 98D.

Yield: 35.4 mg of an oil.

F.

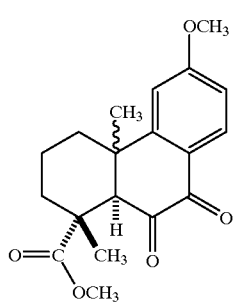

The compound was isolated from the reaction mixture described in Example 98D.

Yield: 150 mg of an oil (10.6%). $^1$H NMR (300 MHz, $CDCl_3$): δ 8.17 (d, J=6 Hz, 1H); 6.95 (m, 1H); 6.80 (m, 1H); 3.90 (s, 3H); 3.70 (s, 3H); 3.36 (s, 0.5H); 2.50 (m, 1.5H); 1.80–2.10 (m, 1H); 1.42–1.80 (m, 4H); 1.40 (s, 1.5H); 1.20 (s, 1.5H); 1.17 (s, 1.5H); 0.65 (s, 1.5H).

G.

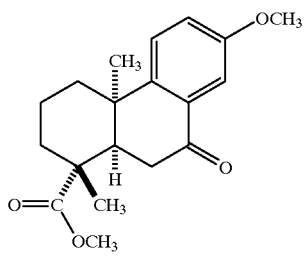

The compound was obtained by separating the compounds (52 mg) of Example 98E by radial chromatography (eluent of 15% Et$_2$O in hexanes).

Yield: 20.5 mg (1.1%) (overall yield). $^1$H NMR (300 MHz, CDCl$_3$): δ 7.52 (d, J=2 Hz, 1H); 7.21 (d, J=6 Hz, 1H); 7.10 (dd, J=2.6 Hz, 1H); 3.87 (s, 3H); 3.63 (s, 3H); 3.05 (dd, J=4,12 Hz, 1H); 2.72 (m, 1H); 2.20–2.50 (m, 2H); 1.80 (m, 2H); 1.40–1.60 (m, 3H); 1.30 (s, 3H) and 0.70 (s, 3H). MS(FD): m/e 316 (M+).

H.

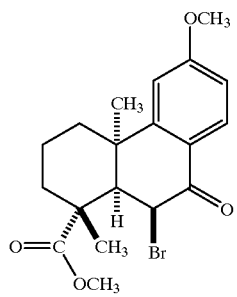

The compound was prepared substantially in accordance with the procedure detailed in Example 71A, using 975 mg (3.08 mmol) of the compound of Example 98D. The crude material was purified using flash chromatography (SiO$_2$, eluent of 15% of Et$_2$O in hexanes).

Yield: 532.6 mg (44%). $^1$H NMR (300 MHz, CDCl$_3$) : δ 8.03 (d, J=6 Hz, 1H); 6.81 (m, 2H); 4.50 (s, 1H); 3.90 (s, 3H); 3.75 (s, 3H); 3.21 (s, 1H); 2.40 (m, 1H); 1.60–2.00 (m, 5H); 1.58 (s, 3H) and 0.60 (s, 3H).

I.

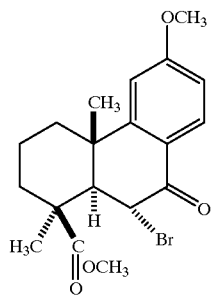

The compound was isolated from the reaction mixture described in Example 98H.

Yield: 465.1 mg of an oil (38%). $^1$H NMR (300 MHz, CDCl$_3$). δ 8.00 (d, J=6 Hz, 1H); 6.85 (m, 2H); 4.97 (d, J=9 Hz, 1H); 3.90 (s, 3H); 3.62 (s, 3H); 3.22 (d, J=9 Hz, 1H); 2.30 (m, 1H); 1.80 (m, 5H); 1.48 (s, 3H) and 1.28 (s, 3H).

J.

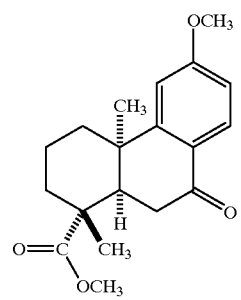

The compound was prepared substantially in accordance with the procedure of Example 72, using 532.0 mg (1.35 mmol) of the compound of Example 98H.

Yield: 280 mg of a pale yellow solid (66%) m.p. 117–119° C. IR(CHCl$_3$): 2942, 1721, 1667 and 1596 cm$^{-1}$. $^1$H NMR (300 MHz, CDCl$_3$): δ 8.04 (d, J=9 Hz, 1H); 6.83 (s, 1H) 6.80 (d, J=3 Hz, 1H).; 3.90 (s, 3H); 3.67 (s, 3H). 3.02 (dd, J=7,19 Hz, 1H); 2.72 (dd, J=2,7 Hz, 1H); 2.40 (m, 2H); 1.80–1.90 (m, 1H); 1.45–1.65 (m, 4H); 1.31 (s, 3H) and 0.70 (s, 3H). MS(FD): m/e 316' (M+).

Elemental Analysis for C$_{19}$H$_{24}$O$_4$: Calcd: C, 72.13; H, 7.65; Found: C, 72.43; H, 7.67.

K.

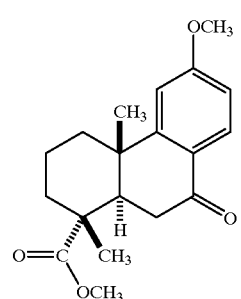

The compound was prepared substantially in accordance with the procedure detailed in Example 72 , using 465 mg (1.17 mmol) of the compound of Example 98I.

Yield: 328 mg of a clear oil (89%). IR(CHCl$_3$): 2942, 1721, 1667 and 1596 cm$^{-1}$. $^1$H NMR (300 MHz, CDCl$_3$ ): δ 8.04 (d, J=9.2 Hz, 1H); 6.85 (s, 1H); 6.81 (d, J=2.6 Hz , 1H); 3.90 (s, 3H); 3 .66 (s, 3H); 2.70 (m, 2H); 2.30 (m, 2H); 1.60–1.90 (m, 5H); 1.35 (s, 3H) and 1.26 (s, 3H). MS(FD): m/e 316 (M+).

EXAMPLE 99

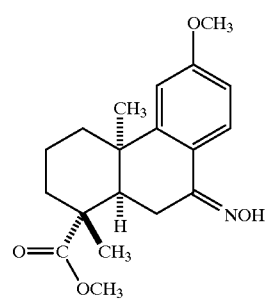

The compound was prepared substantially in accordance with the procedure detailed in Example 62, using 465 mg (1.17 mmol) of the compound of Example 98J.

Yield: 79%. IR(CHCl₃): 3500, 2951 and 1719 cm⁻¹. ¹H NMR (300 MHz, CDCl₃): δ 0.81 (d, J=7 Hz, 1H); 6.82 (d, J=2 Hz, 1H); 6.78 (dd, J=2,7 Hz, 1H); 3.83 (s, 3H); 3.70 (s, 3H); 3.07 (dd, J=6.12 Hz, 1H); 2.60 (m, 2H); 2.40 (m, 1H); 1.80 (m, 1H); 1.40–1.60 (m, 4H); 1.20 (s, 3H) and 0.60 (s, 3H). MS(FD): m/e 331 (M+).

Elemental Analysis for $C_{19}H_{25}NO_4$: Calcd: C, 68.86; H, 7.60; N, 4.23; Found: C, 68.56; H, 7.44; N, 4.25.

EXAMPLE 100

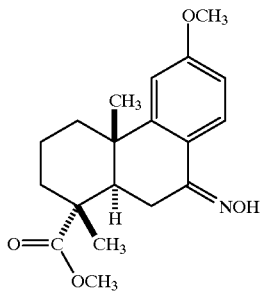

The compound was prepared substantially in accordance with the procedure detailed in Example 62, using the compound of Example 98K.

Yield: 61%. m.p. 162–165° C. IR(CHCl₃): 3018, 2951, 1720 and 1600 cm⁻¹. ¹H NMR (300 MHz, CDCl₃): δ 7.81 (d, J=6 Hz, 1H); 6.82 (m, 3H); 3.90 (s, 3H); 3.70 (s, 3H); 2.62 (d, J=6 Hz, 2H); 2.20–2.43 (m, 2H); 1.60–1.90 (m, 5H); 1.40 (s, 3H) and 1.10 (s, 3H). MS(FD): m/e 331 (M+).

Elemental Analysis for $C_{19}H_{25}NO_4$: Calcd: C, 68.86; H, 7.60; N, 4.23; Found: C, 68.79; H, 7.42; N, 4.33.

EXAMPLE 101

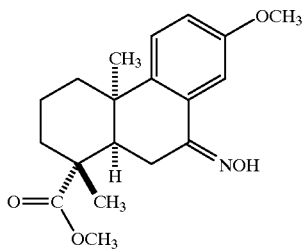

The compound was prepared substantially in accordance with the procedure detailed in Example 62, using the compound of Example 98G.

Yield: 90%. ¹H NMR (300 MHz, CDCl₃): δ 7.40 (d, J=2 Hz, 1H); 7.20 (d, J=6 Hz, 1H); 6.93 (dd, J=2,6 Hz, 1H); 3.82 (s, 3H); 3.70 (s, 3H); 3.10 (dd, J=5,13 Hz, 1H); 2.50–2.63 (m, 2H); 2.1 (d, J=8 Hz, 1H); 2.30 (m, 1H); 1.20–1.40 (m, 4H); 1.20 (s, 3H) and 0.60 (s, 3H). MS(FD): m/e 331 (M+).

EXAMPLE 102

A.

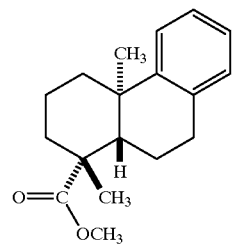

The compound of Example 70A (14.0 g) was subjected to flash chromatography (SiO₂, eluent of hexanes) to provide 12.5 g of an oil. This oil was redissolved in hexanes and allowed to stand for 16 hours in a refrigerator which resulted in the formation of a solid. This solid was isolated by filtration (3.9 g, 14.3 mmol) and 1.0 g was dissolved in 100 ml of triethylene glycol dimethyl ether containing 1.0 g of 10% Pd/C and refluxed for 6 hours, under N₂. After cooling, the mixture was filtered over celite, and the filtrate was partitioned between EtOAc and H₂O. The resultant layers were separated and the organic layer was dried over Na₂SO₄, filtered and concentrated in vacuo to provide a liquid. This liquid was diluted with H₂O which resulted in the formation of a solid. This solid was isolated by filtration, dissolved in hexanes and allowed to crystallize at room temperature.

Yield: 297 mg (1.09 mmol).

B.

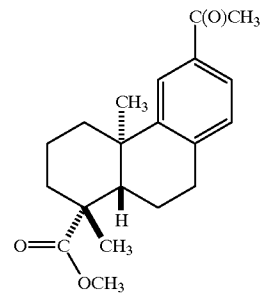

The compound was prepared substantially in accordance with the procedure detailed in Example 98A, using the compound of Example 102A.

Yield: 330 mg (98%).

C.

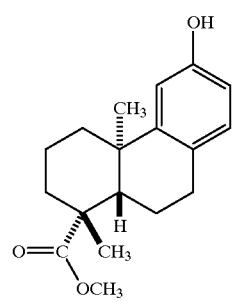

The compound was prepared substantially in accordance with the procedure detailed in Example 98B, using the compound of Example 102B.

Yield: 300 mg (99%).

D.

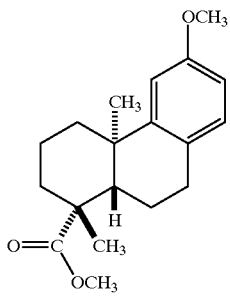

The compound was prepared substantially in accordance with the procedure detailed in Example 98C, using the compound of Example 102C.

Yield: 239 mg (76%).

E.

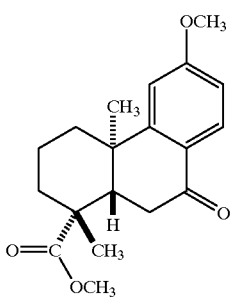

The compound was prepared substantially in accordance with the procedure detailed in Example 70B, using the compound of Example 102D.

Yield: 153 mg of a white solid (61%). m.p. 107–108° C. IR(KBr): 2943, 1724, 1681 and 1591 cm$^{-1}$. $^1$H NMR (300 MHz, CDCl$_3$): δ 8.06 (d, J=8.5 Hz, 1H); 6.88 (d, J=2.2 Hz, 1H); 6.83 (dd, J-2.2,8.5 Hz, 1H); 3.84 (s, 3H); 3.70 (s, 3H); 3.19 (m, 1H); 2.95 (dd, J=3.3,18.0 Hz, 1H); 2.33 (brd, J=11.0 Hz, 2H); 2.05 (m, 2H); 1.70 (m, 1H); 2.57 (m, 1H); 1.25 (s, 3H); 1.12 (m, 1H) and 1.10 (s, 3H). MS(FD): m/e 316 (M+).

Elemental Analysis for C$_{19}$H$_{24}$O$_4$: Calcd: C, 72.13; H, 7.65; Found: C, 72.13; H, 7.45.

EXAMPLE 103

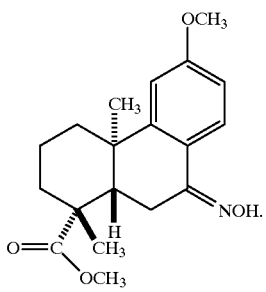

The compound was prepared substantially in accordance with the procedure detailed in Example 62, using the compound of Example 102E. The crude material was purified by recrystallization form Et$_2$O/hexanes.

Yield: 84%. m.p. 172–174° C. IR(KBr): 3286, 2959, 1721 and 1603 cm$^{-1}$. $^1$H NMR (300 MHz, CDCl$_3$): δ 7.93 (d, J=6 Hz, 1H); 6.84 (d, J=2 Hz, 1H); 6.78 (dd, J=2.6 Hz, 1H); 3.80 (s, 3H); 3.65 (s, 3H); 3.43 (dd, J=3.12 Hz, 1H); 3.10 (m, 1H); 2.30 (d, J=8 Hz, 2H); 2.00 (m, 1H); 1.70 (m, 2H); 1.50 (m, 1H); 1.30 (s, 3H); 1.10 (m, 1H) and 1.00 (s, 3H). MS(FD): m/e 331 (M+).

Elemental Analysis for C$_{19}$H$_{25}$NO$_4$: Calcd: C, 68.86; H, 7.60; N, 4.23; Found: C, 69.09; H, 7.55; N, 4.38.

As noted above, the compounds of the present invention are useful for inhibiting an envelope virus that undergoes hemagglutinin-mediated fusion with a host cell. An embodiment of the present invention is a method of treating or preventing a viral infection where the virus is an envelope virus that undergoes hemagglutinin-mediated fusion with a host cell which comprises administering to a virus infected cell, a cell susceptible of infection or a mammal in need thereof an effective amount of a compound of formula I or a pharmaceutically acceptable salt thereof. Another embodiment of the present invention is a method of treating or preventing the symptoms associated with a viral infection comprising administering to a mammal in need thereof an effective amount of a compound of formula I or a pharmaceutically acceptable salt thereof. A further embodiment of the present invention is a method of inhibiting viral replication comprising administering to a virus-infected cell, a cell susceptible to infection or a mammal in need thereof, anr effective amount of a compound of formula I or a pharmaceutically acceptable salt thereof.

The term "effective amount" as used herein, means an amount of a compound of the present invention which is capable of inhibiting the hemagglutinin-mediated viral fusion with the host cell. The viral inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg. The compounds can be administered by a variety of routes including oral, rectal, transdermal, subcutaneous, intravenous, intramuscular and intranasal.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following experiments were carried out to demonstrate the ability of the compounds of the present invention to inhibit influenza.

In vitro CPE/XTT Assay

MDCK cells were dispersed in a microtiter plate (96 wells) at 10,000 cells per well with Medium 199 containing Earl's balanced salt solution (EBSS), 1% fetal bovine serum (FBS), penicillin (100 units/ml) and streptomycin (100 μg/ml). After standing overnight at 37° C. in a carbon dioxide ($CO_2$) incubator, the MDCK cells were infected with ~0.1 moi (mutiplicity of infection) of influenza virus (i.e. A/Kawasaki/89 or B/Hong Kong and B/Great Lakes) at 0.03 moi. After allowing the virus to adsorb to the cells for 1–2 hours, medium containing serial dilutions of drug or medium alone was added to the wells. The resultant mixtures were incubated for 2–3 days (until extensive cpe was apparent in medium alone wells). The antiviral effect of a test compound was assessed by performing the following XTT assay.

A fresh solution (0.4 mg/ml) of XTT [2,3-bis(methoxy-4-nitro-5-sulfophenyl)-2H-tetraazolium-5-carboxanilide, inner salt, sodium salt] in warm medium without FBS was prepared. For each 5 ml of the XTT solution, 25 μl of 5 mM PMS (phenazine methosulfate) in phosphate buffer saline was added. After withdrawing the cultured supernatant, 100 μl of the freshly prepared XTT/PMS mixture was added to each of the microtiter wells. The wells were then incubated at 37° C. (under $CO_2$) for 3–4 hours or until color change is prominent. The absorbance at 450 nm (ref. 650 nm) was read in a spectrophotometer. The concentration of test compound required to cause 50% cytotoxic effect ($TC_{50}$) relative to a control with no drug and no virus present and which inhibits the development of virus cytopathic effect (cpe) by 50% ($IC_{50}$) or 90% ($IC_{90}$) was determined from the linear portion of each dose response curve.

Using this CPE/XTT assay, the $IC_{50}$ of the compounds of formula I was determined to be in the range of 0.01–32.0 μg/ml for influenza A/Kawasaki/89 and in the range of 0.7–97.0 μg/ml for influenza B/Great Lakes.

Plaque Reduction Assay

Susceptible MDCK cells were grown in 6 well tissue culture treated cluster plates at $1 \times 10^6$ cells/well in Minimum 199 with 1 percent fetal bovine serum, penicillin (100 units/ml) and streptomycin (100 μg/ml). After overnight incubation at 37° C., the growth medium was removed and 0.2 ml/well of an appropriate dilution of virus was added. After adsorption for 1–2 hour at room temperature, the infected cell sheet was overlaid with equal parts of 1.5% sterile agarose solution and a twofold concentration of medium 199 (with 2% fetal bovine serum, 100 units/ml of penicillin and 100 μg/ml streptomycin) containing varying concentrations of compounds.

The compounds were dissolved in DMSO at a concentration of 20 mg/ml and an aliquot was diluted to the desired concentration in DMSO and then added to the agar medium mixture. The plates were incubated in a $CO_2$ incubator at 37° C. until the DMSO control wells contained plaques of optimal size. Then, a solution containing 10 percent formalin and 2 percent sodium acetate was added to each well to inactivate the virus and fix the cell sheet to the plastic surface The fixed cell sheets were stained with 0.5 percent crystal violet and the plaques were counted. Results from duplicate wells at each concentration were averaged and compared with DMSO control wells. The inhibition of plaque formation by 50 or 90 percent ($IC_{50}$ or $IC_{90}$) was calculated from the linear region of the inhibition concentration curve using the method of Reed and Muench, Am. J. Hyg., vol. 27, pages 493–497 (1958).

Using the plaque reduction assay, the $IC_{50}$ of the compounds of formula I was determined to be in the range of 0.006–100.0 μg/ml for influenza a/kawasaki and in the range of 1.47–100.0 μg/ml for influenza b/great lakes.

What is claimed is:

1. A method of inhibiting an envelope virus selected from the group consisting of influenza, bovine diarrheal, hepatitis C and tick borne encephalitis virus that undergoes hemagglutinin-mediated fusion with a host cell which comprises administering to a virus-infected cell, a cell susceptible of infection or a mammal in need thereof, an effective amount of a compound of formula I

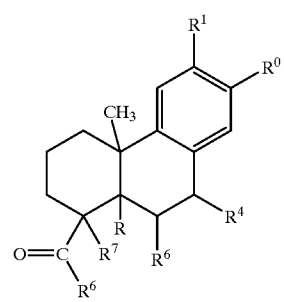

wherein:
R is hydrogen or R and $R^6$ combine to form a bond;
$R^0$ and $R^1$ are independently hydrogen, hydroxy, $C_1$–$C_6$ alkyl, $C_1$–$C_6$ alkoxy, hydroxy($C_1$–$C_6$ alkyl), sulfhydryl, sulfamyl, —$SO_2$—Cl, —S—C(O)—N($CH_3$)$_2$, amino, $C_1$–$C_4$ alkylamino, di($C_1$–$C_4$ alkyl)amino, $C_1$–$C_4$ alkylsulfonylalmino, di (C$_1$–C$_4$ alkylsulfonyl)amino —X$^0$—O—C(O)—C$_1$–C$_4$ alkyl, —O—(X$^1$)$_i$—X$^2$, —C(O)—X$^3$, —N—C(O)—R$^2$ or —O—R$^3$;

X$^0$ is a bond or divalent(C$_1$–C$_6$ alkyl);

X$^1$ is an amino acid;

X$^2$ is hydrogen or an amino protecting group;

i is 1, 2 or 3;

X$^3$ is C$_1$–C$_6$ alkyl, C$_1$–C$_6$ alkoxy, halo(C$_1$–C$_6$ alkyl), hydroxy(C$_1$–C$_6$ alkyl) or phenyl;

R$^2$ is C$_1$–C$_4$ alkyl, C$_1$–C$_4$ alkoxy, halo(C$_1$–C$_4$ alkyl), hydroxy(C$_1$–C$_4$ alkyl), phenyl, p-methoxy-phenyl, p-fluoro-phenyl, naphthyl, pyridyl, piperidinyl, thiazolyl, oxazolyl, thienyl, furyl, tetrahydrofuryl or cyclohexyl;

R$^3$ is C$_1$–C$_6$ alkenyl, —CH$_2$—R$^{3a}$, —C(O)—R$^{3b}$, —C(S)—R$^{3c}$, —C(CH$_3$)$_2$C(O)NH$_2$, phenyl or a group of the formula:

or

;

R$^{3a}$ is phenyl, p-fluorophenyl, pyridyl, pyrrolidinyl, piperidinyl, piperazinyl, morpholinyl, N—(C$_1$–C$_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

R$^{3b}$ is pyrrolidinyl, piperidinyl, piperazinyl, morpholinyl, N—(C$_1$–C$_4$ alkoxycarbonyl)piperidinyl, N-(trifluoromethyl)piperidinyl, benzyloxy, pyridylmethyloxy, C$_1$–C$_6$ alkoxy, halo(C$_1$–C$_4$ alkoxy), amino, C$_1$–C$_4$-alkylamino or di(C$_1$–C$_4$ alkyl)amino;

R$^{3c}$ is amino, C$_1$–C$_4$ alkylamino Or di(C$_1$–C$_4$ alkyl) amino;

R$^{3d}$ is oygen, hydroximo, hydrazino or =CHZ;

Z is hydrogen, C$_1$–C$_4$ alkyl, halogen, di(C$_1$–C$_4$ alkyl) amino, C$_1$–C$_4$ alkoxycarbonyl, carbamoyl (C$_1$–C$_4$ alkyl), N—(C$_1$–C$_4$ alkyl)carbamoyl or N,N-di(C$_1$–C$_4$ alkyl)carbamoyl:

R$^{3e}$ is hydrogen, nitro or trifluoromethyl;

X is a bond or —(CH$_2$)—,

R$^4$ is hydrogen, hydroxy, amino, C$_1$–C$_4$ alkylamino, di(C$_1$–C$_4$ alkyl)amino, C$_1$–C$_4$ alkoxy, =O, —O—S(CH$_3$)$_2$C(CH$_3$)$_3$, C$_2$–C$_6$ alkanoyloxy, N—(C$_2$–C$_6$ alkanoyl)amino, =N—R$^5$ or R$^4$ and R$^6$ combine to form a bond;

R$^5$ is hydroxy, amino, C$_1$–C$_4$ alkylamino, di(C$_1$–C$_4$ alkyl) amino, C$_1$–C$_4$ alkoxy, pyridylmethoxy, benzyloxy, piperazinyl, N-(methyl)piperazinyl or —O—CH$_2$—C(O)—R$^{5a}$;

R$^{5a}$ is hydroxy or C$_1$–C$_4$ alkoxy;

R$^6$ is hydrogen, halo, C$_1$–C$_4$ alkyl or =O;

R$^7$ is hydrogen or C$_1$–C$_4$ alkyl;

R$^8$ is hydroxy, halo, C$_1$–C$_6$ alkoxy, pyrrolidinyl, peridinyl, piperazinyl, 4-methyl-piperazinyl, morpholinyl or —N(R$^9$)—R$^{10}$;

R$^9$ is hydrogen or methyl;

R$^{10}$ is -(divalent C$_1$–C$_6$ alkyl)-R$^{10a}$;

R$^{10a}$ is pyridyl, with the proviso that R cannot combine with both R$^4$ and R to form a bond;

or a pharmaceutically acceptable salt thereof.

2. A method of treating or preventing a viral infection where the virus is an envelope virus selected from the group consisting of influenza, bovine diarrhea, heptitis C and tick borne encephalitis virus that undergoes hemagglutinin-mediated fusion with a host cell which comprises administering to a virus-infected cell, a cell susceptible of infection or a mammal in need thereof, an effective amount of a compound of formula I

I wherein:

R is hydrogen or R and R$^6$ combine to form a bond;

R$^0$ and R$^1$ are independently hydrogen, hydroxy, C$_1$–C$_6$ alkyl, C$_1$–C$_6$ alkoxy, hydroxy(C$_1$–C$_6$ alkyl), sulfhydryl, sulfamyl, —SO$_2$—Cl, —S—C(O)—N(CH$_3$)$_2$, amino, C$_1$–C$_4$ alkylamino, di(C$_1$–C$_4$ alkyl)amino, C$_1$–C$_4$ alkylsulfonylamino, di(C$_1$–C$_4$ alkylsulfonyl)amino —X$^0$—O—C(O)—C$_1$–C$_4$ alkyl, —O—(X$^1$)$_i$—X$^2$, —C(O)—X$^3$, —N—C(O)—R$^2$ or —O—R$^3$;

X$^0$ is a bond or divalent(C$_1$–C$_6$ alkyl);

X$^1$ is an amino acid;

X$^2$ is hydrogen or an amino protecting group;

i is 1, 2 or 3,

X$^3$ is C$_1$–C$_6$ alkyl C$_1$–C$_6$ alkoxy, halo(C$_1$–C$_6$ alkyl), hydroxy(C$_1$–C$_6$ alkyl) or phenyl;

R$^2$ is C$_1$–C$_4$ alkyl, C$_1$–C$_4$ alkoxy, halo(C$_1$–C$_4$ alkyl), hydroxy(C$_1$–C$_4$ alkyl), phenyl, p-methoxy-phenyl, p-fluoro-phenyl, naphthyl, pyridyl, pipridinyl, thiazolyl, oxazolyl, thienyl, furyl, tetrahydrofuryl or cyclohexyl;

R$^3$ is C$_1$–C$_6$ alkenyl, —CH$_2$—R$^{3a}$, —C(O)—R$^{3b}$, —C(S)—R$^{3c}$, —C(CH$_3$)$_2$C(O)NH$_2$, phenyl or a group of the formula:

87

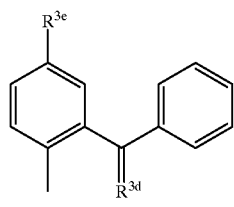

or

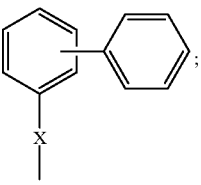

$R^{3a}$ is phenyl, p-fluorophenyl, pyridyl, pyrrolidinyl, piperidinyl, piperazinyl, morpholinyl, N-($C_1$-$C_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

$R^{3b}$ is pyrrolidinyl, piperidinyl, piperazinyl, morpholinyl, N-($C_1$-$C_4$ alkoxycarbonyl)piperidinyl, N-(trifluoromethyl)piperidinyl, benzyloxy pyridylinethyloxy, $C_1$-$C_6$ alkoxy, halo($C_1$-$C_4$ alkoxy), anino, $C_1$-$C_4$ alkylamino or di($C_1$-$C_4$ alkyl)amino;

$R^{3c}$ is amino, $C_1$-$C_4$ alkylamino or di($C_1$-$C_4$ alkyl)amino;

$R^{3d}$ is oxygen, hydroximino, hydrazino or =CHZ;

Z is hydrogen, $C_1$-$C_4$ alkyl, halogen, di($C_1$-$C_4$ alkyl) amino, $C_1$-$C_4$ alkoxycarbonyl, carbamoyl ($C_1$-$C_4$ alkyl), N—($C_1$-$C_4$ alkyl)carbamoyl or N,N-di($C_1$-$C_4$ alkyl) carbamoyl;

$R^{3e}$ is hydrogen, nitro or trifluoromethyl;

X is a bond or —($CH_2$)—;

$R^4$ is hydrogen, hydroxy, amino, $C_1$-$C_4$ alkylamino, di($C_1$-$C_4$ alkyl)amino, $C_1$-$C_4$ alkoxy, =O, —O—S ($CH_3$)$_2$C($CH_3$)$_3$, $C_2$-$C_6$ alkanoyloxy, N-($C_2$-$C_6$ alkanoyl)amino, =N—$R^5$ or $R^4$ and $R^6$ combine to form a bond;

$R^5$ is hydroxy, amino, $C_1$-$C_4$ alkylamino, di($C_1$-$C_4$ alkyl) amino, $C_1$-$C_4$ alkoxy, pyridylmethoxy, benzyloxy, piperazinyl, N-(methyl)piperazinyl or —O—$CH_2$—C(O)—$R^{5a}$;

$R^5$a is hydroxy or $C_1$-$C_4$ alkoxy;

$R^6$ is hydrogen, halo, $C_1$-$C_4$ alkyl or =O;

$R^7$ is hydrogen or $C_1$-$C_4$ alkyl;

$R^8$ is hydroxy, halo, $C_1$-$C_6$ alkoxy, pyrrolidinyl, piperidinyl, piperazinyl, 4-methyl-piperazinyl, morpholinyl or —N($R^9$)—$R^{10}$;

$R^9$ is hydrogen or methyl;

$R^{10}$ is -(divalent $C_1$-$C_6$ alkyl)-$R^{10a}$;

$R^{10a}$ is pyridyl, with the proviso that $R^6$ cannot combine with both $R^4$ and R to form a bond;

or a pharmaceutically acceptable salt thereof.

3. The method of claim 1 wherein said compound is a compound of formula I where $R^0$ is hydrogen, hydroxy, $C_1$-$C_6$ alkyl, $C_1$-$C_6$ alkoxy, hydroxy($C_1$-$C_6$ alkyl), —$X^0$—O—C(O)—$C_1$-$C_4$ alkyl, —O—($X^1$)$_i$—$X^2$, —C(O)—$X^3$ or —O—$R^3$;

88

$R^1$ is hydrogen, hydroxy, $C_1$-$C_6$ alkoxy, sulfhydryl, sulfamyl, —$SO_2$—Cl, amino, di($C_1$-$C_4$ alkylsulfonyl) amino, —C(O)—$X^3$, —N—C(O)—$R^2$ or —O—$R^3$;

$X^0$ is a bond or divalent($C_1$-$C_6$ alkyl);

$X^1$ is an amino acid;

$X^2$ is hydrogen or an amino protecting group;

i is 1 or 2;

$X^3$ is $C_1$-$C_6$ alkyl;

$R^{10a}$ is pyridyl;

or a pharmaceutically acceptable salt thereof.

4. The method of claim 3 wherein said compound is a compound of formula I where $R^0$ is hydrogen, hydroxy, $C_1$-$C_6$ alkoxy, —O—($X^1$)$_i$—$X^2$, —$X^0$—O—C(O)—$C_1$-$C_4$ alkyl or —O—$R^3$;

$R^1$ is hydrogen, hydroxy, $C_1$-$C_6$ alkoxy or —O—$R^3$;

$X^0$ is a bond;

$X^1$ is an amino acid;

$X^2$ is hydrogen or an amino protecting group;

i is 1 or 2;

$R^3$ is $C_1$-$C_6$ alkenyl, —$CH_2$—$R^{3a}$ or —C(O)—$R^{3b}$;

$R^{3a}$ is p-fluorophenyl or pyridyl;

$R^{3b}$ is piperidinyl;

$R^4$ is hydrogen, hydroxy, =O or =N—$R^5$;

$R^5$ is hydroxy, dimethylamino or N-(methyl) piperazinyl;

$R^6$ is hydrogen, bromo or =O;

$R^7$ is methyl; and $R^8$ is methoxy;

or a pharmaceutically acceptable salt thereof.

5. The method of claim 4 wherein said compound is a compound of formula I where

R is hydrogen;

$R^0$ is hydrogen, hydroxy, $C_1$-$C_4$ alkoxy, —O—($X^1$)$_i$—$X^2$, —O—C(O)methyl or —O—$R^3$;

$R^1$ is hydrogen, hydroxy, $C_1$-$C_4$ alkoxy or —O—$R^3$;

$X^1$ I is glycine, alanine or valine;

$R^2$ is hydroxy($C_1$-$C_4$ alkyl);

$R^3$ is $C_1$-$C_6$ alkenyl, —$CH_2$—$R^{3a}$, —C(O)—$R^{3b}$, —C(S)—$R^{3c}$, —C($CH_3$)$_2$C(O)$NH_2$ or a group of the formula:

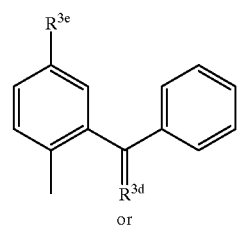

or

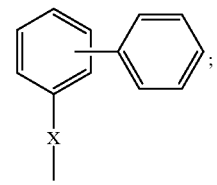

$R^{3a}$ is phenyl, p-fluorophenyl, pyridyl, piperidinyl, piperazinyl or morpholinyl;

$R^{3b}$ is piperidinyl, piperazinyl, morpholinyl, N—($C_1$-$C_4$ alkoxycarbonyl)piperidinyl, N-(trifluoromethyl) piperidinyl, halo($C_1$-$C_4$ alkoxy) or di($C_1$-$C_4$ alkyl) amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is hydrogen, hydroxy, amino, =O, $C_2$–$C_6$ alkanoyloxy, =N—$R^5$, —OSi($CH_3$)$_2$ or $R^4$ and $R^6$ combine to form a bond;

$R^5$ is hydroxy, amino, di($C_1$–$C_4$ alkyl)amino, $C_1$–$C_4$ alkoxy, pyridylmethoxy, N-(methyl)piperazinyl or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, methoxy, 4-methylpiperazinyl or —N($R^9$)—$R^{10}$;

$R^9$ is hydrogen;

$R^{10}$ is —$CH_2$—$R^{10a}$; and $X^2$ is hydrogen, t-butoxycarbonyl or benzyloxycarbonyl;

$R^4$ is =O or =N—$R^5$;

$R^5$ is hydroxy;

$R^6$ is hydrogen;

or a pharmaceutically acceptable salt thereof.

6. The method of claim 2 wherein said compound is a compound of formula I where $R^0$ is hydrogen, hydroxy, $C_1$–$C_6$ alkyl, $C_1$–$C_6$ alkoxy, hydroxy($C_1$–$C_6$ alkyl), —$X^0$—O—C(O)—$C_1$–$C_4$ alkyl, —O—($X^1$)$_i$—$X^2$, —C(O)—$X^3$ or —O—$R^3$;

$R^1$ is hydrogen, hydroxy, $C_1$–$C_6$ alkoxy, sulfhydryl, sulfamyl, —$SO_2$—Cl, amino, di($C_1$–$C_4$ alkylsulfonyl)amino, —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group, i is 1 or 2;

$X^3$ is $C_1$–$C_6$ alkyl;

$R^2$ is hydroxy($C_1$–$C_4$ alkyl);

$R^3$ is $C_1$–$C_6$ alkenyl, —$CH_2$—$R^{3a}$, —C(O)—$R^{3b}$, —C(S)—$R^{3c}$, —C($CH_3$)$_2$C(O)$NH_2$ or a group of the formula:

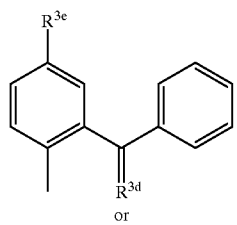

or

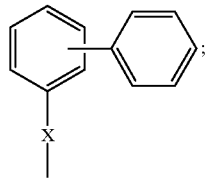

$R^{3a}$ is phenyl, p-fluorophenyl, pyridyl, piperidinyl, piperazinyl or morpholinyl;

$R^{3b}$ is piperidinyl, piperazinyl, morpholinyl, N-($C_1$–$C_4$ alkoxycarbonyl)piperidinyl, N-(trifluoromethyl)piperidinyl, halo($C_1$–$C_4$ alkoxy) or di($C_1$–$C_4$ alkyl)amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is hydrogen, hydroxy, amino, =O, $C_2$–$C_6$ alkanoyloxy, =N—$R^5$, —OSi($CH_3$)$_2$ or $R^4$ and $R^6$ combine to form a bond;

$R^5$ is hydroxy, amino, di($C_1$–$C_4$ alkyl)amino, $C_1$–$C_4$ alkoxy, pyridylmethoxy, N-(methyl)piperazinyl or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, methoxy, 4-methylpiperazinyl or —N($R^9$)—$R^{10}$;

$R^9$ is hydrogen;

$R^{10}$ is —$CH_2$—$R^{10a}$; and $R^{10a}$ is pyridyl.

7. The method of claim 6 wherein said compound is a compound of formula I where $R^0$ is hydrogen, hydroxy, $C_1$–$C_6$ alkoxy, —O—($X^1$)$_i$—$X^2$, —$X^0$—O—C(O)—$C_1$–$C_4$ alkyl or —O—$R^3$;

$R^1$ is hydrogen, hydroxy, $C_1$–$C_6$ alkoxy or —O—$R^3$;

$X^0$ is a bond;

$X^1$ is an amino acid;

$X^2$ is hydrogen or an amino protecting group;

i is 1 or 2;

$R^3$ is $C_1$–$C_6$ alkenyl, —$CH_2$—$R^{3a}$ or —C(O)—$R^{3b}$;

$R^{3a}$ is p-fluorophenyl or pyridyl;

$R^{3b}$ is piperidinyl;

$R^4$ is hydrogen, hydroxy, =O or =N—$R^5$;

$R^5$ is hydroxy, dimethylamino or N-(methyl)piperazinyl;

$R^6$ is hydrogen, bromo or =O;

$R^7$ is methyl; and $R^8$ is methoxy;

or a pharmaceutically acceptable salt thereof.

8. The method of claim 7 wherein said compound is a compound of formula I where

R is hydrogen;

$R^0$ is hydrogen, hydroxy, $C_1$–$C_4$ alkoxy, —O—($X^1$)$_i$—$X^2$, —O—C(O)methyl or —O—$R^3$;

$R^1$ is hydrogen, hydroxy, $C_1$–$C_4$ alkoxy or —O—$R^3$;

$X^1$ is glycine, alanine or valine;

$X^2$ is hydrogen, t-butoxycarbonyl or benzyloxycarbonyl;

$R^4$ is =O or =N—$R^5$;

$R^5$ is hydroxy;

$R^6$ is hydrogen;

or a pharmaceutically acceptable salt thereof.

* * * * *